US012662707B2

(12) United States Patent
Olive et al.

(10) Patent No.: US 12,662,707 B2
(45) Date of Patent: Jun. 23, 2026

(54) MYC AMPLIFICATION DRIVES RESISTANCE TO PAN-RAS INHIBITORS IN PANCREATIC CANCER

(71) Applicants: The Trustees of Columbia University in the City of New York, New York, NY (US); The University of North Carolina at Chapel Hill, Chapel Hill, NC (US); Revolution Medicines, Inc., Redwood City, CA (US)

(72) Inventors: Kenneth Paul Olive, New York, NY (US); Urszula Wasko, New York, NY (US); Channing Der, Chapel Hill, NC (US); Mallika Singh, Redwood City, CA (US); Jingjing Jiang, Redwood City, CA (US)

(73) Assignees: The Trustees of Columbia University in the City of New York, New York, NY (US); The University of North Carolina at Chapel Hill, Chapel Hill, NC (US); Revolution Medicines, Inc., Redwood City, CA (US)

( * ) Notice: Subject to any disclaimer, the term of this patent is extended or adjusted under 35 U.S.C. 154(b) by 0 days.

(21) Appl. No.: 19/035,409

(22) Filed: Jan. 23, 2025

(65) Prior Publication Data

US 2025/0250640 A1 Aug. 7, 2025

Related U.S. Application Data

(60) Provisional application No. 63/624,528, filed on Jan. 24, 2024.

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/156* (2013.01)

(58) Field of Classification Search
None
See application file for complete search history.

(56) References Cited

FOREIGN PATENT DOCUMENTS

| | | | | |
|---|---|---|---|---|
| WO | 2021186324 | A1 | 9/2021 | |
| WO | 2022246459 | A1 | 11/2022 | |
| WO | 2023122781 | A2 | 6/2023 | |
| WO | 2023194310 | A1 | 10/2023 | |
| WO | WO-2023230577 | A1 * | 11/2023 | ............. A61P 35/00 |
| WO | 2024176131 | A1 | 8/2024 | |
| WO | 2024229406 | A1 | 11/2024 | |

OTHER PUBLICATIONS

Zhao et al. Nature. 599: 679-683 and Supplementary materials, 23 pages total (Year: 2021).*
Edwards et al. Cancer Research. Dec. 2023. 83: 4112-4129 (Year: 2023).*
Punekar et al. "The current state of the art and future trends in RAS-targeted cancer therapies", Nature Reviews Clinical Oncology (2022) vol. 19, pp. 637-655.
Lee et al. "c-MYC Copy-Number Gain is an Independent Prognostic Factor in Patients with Colorectal Cancer", PLoS One (2015) 10(10):e0139727, 12 pages.
Seo et al. "Clinicopathologic and prognostic significance of c-MYC copy number gain in lung adenocarcinomas", British Journal of Cancer (2014) 110, pp. 2688-2699.
Third Party Observation dated Mar. 10, 2025, issued in PCT International Application No. PCT/US2025/012673.
Hagenbeek et al., "An allosteric pan-TEAD inhibitor blocks oncogenic YAP/TAZ signaling and overcomes Kras G12C inhibitor resistance," Nature Cancer, vol. 4, Jun. 5, 2023, pp. 812-828.
Mira et al., "YAP and TAZ orchestrate adaptive resistance to KRAS inhibitors," Nature Cancer, vol. 4, Jun. 2023, pp. 784-786.
Edwards et al., "TEAD Inhibition Overcomes YAP1/TAZ-Driven Primary and Acquired Resistance to KRAS G12C Inhibitors," Cancer Research, 2023, vol. 83, No. 24, pp. 4112-4129.
Johnson et al., "All Roads Lead to Rome: YAP/TAZ Activity Influences Efficacy of KRAS G12C Inhibitors," Cancer Research, vol. 83, No. 24, 2023, pp. 4005-4007.
Chapeau et al., "Direct and selective pharmacological disruption of the YAP-TEAD interface by IAG933 inhibits Hippo-dependent and RAS-MAPK-altered cancers," Nature Cancer, vol. 5, Apr. 2, 2024, pp. 1102-1120.
Kapoor et al., "Yap1 activation enables bypass of oncogenic Kras addiction in pancreatic cancer," Cell, vol. 158, No. 1, 7 Jul. 3, 2014, pp. 185-197.

* cited by examiner

*Primary Examiner* — Carla J Myers
(74) *Attorney, Agent, or Firm* — Amster, Rothstein & Ebenstein LLP

(57) ABSTRACT

Methods of treating a tumor in a subject comprising administering to the subject an amount of a $RAS^{MULTI}$ inhibitor and an amount of a TEAD inhibitor, effective to treat a tumor, and methods of treating a tumor resistant to a $RAS^{MULTI}$ inhibitor therapy comprising administering to a tumor so-identified an amount of a $RAS^{MULTI}$ inhibitor and an amount of a TEAD inhibitor, effective to treat a tumor resistant to a $RAS^{MULTI}$ inhibitor therapy.

16 Claims, 33 Drawing Sheets

MYC AMPLIFICATION DRIVES RESISTANCE TO PAN-RAS INHIBITORS IN PANCREATIC CANCER

CROSS-REFERENCE TO RELATED APPLICATIONS

This application claims benefit of U.S. Provisional Application No. 63/624,528, filed Jan. 24, 2024, the contents of which are hereby incorporated by reference.

STATEMENT OF GOVERNMENT SUPPORT

This invention was made with government support under CA257911, and CA232113 awarded by the National Institutes of Health. The government has certain rights in the invention.

BACKGROUND OF THE INVENTION

Throughout this application, various publications are referenced, including referenced in parenthesis. The disclosures of all publications mentioned in this application in their entireties are hereby incorporated by reference into this application in order to provide additional description of the art to which this invention pertains and of the features in the art which can be employed with this invention.

The entire contents of WO2023/194310 and WO2022/246459 and WO2022/060836 and WO2022/217042 are hereby incorporated by reference.

Broad-spectrum RAS inhibition holds the potential to benefit roughly a quarter of human cancer patients whose tumors are driven by RAS mutations. RMC-7977 is a highly selective inhibitor of the active GTP-bound forms of KRAS, HRAS, and NRAS, with affinity for both mutant and wild type (WT) variants (an example of a pan-RAS inhibitor or "$RAS^{MULTI}$(ON)").

Resistance to RMC-7977 is possible, and its underlying mechanisms, and how to overcome it, are not known.

SUMMARY OF THE INVENTION

A method of treating a tumor resistant to a $RAS^{MULTI}$ inhibitor therapy comprising (i) identifying or having identified the tumor resistant to a $RAS^{MULTI}$ inhibitor therapy as having (a) a MYC copy number higher than a predetermined reference value and/or (b) a JUN copy number higher than a predetermined reference value; and (ii) administering to a tumor so-identified in (i) an amount of a $RAS^{MULTI}$ inhibitor and an amount of a TEAD inhibitor, effective to treat a tumor resistant to a $RAS^{MULTI}$ inhibitor therapy.

A method of treating a tumor in a subject comprising administering to the subject an amount of a $RAS^{MULTI}$ inhibitor and an amount of a TEAD inhibitor, effective to treat a tumor.

A method of treating a tumor resistant to a $RAS^{MULTI}$ inhibitor therapy comprising administering to a tumor so-identified an amount of a $RAS^{MULTI}$ inhibitor and an amount of a TEAD inhibitor, effective to treat a tumor resistant to a $RAS^{MULTI}$ inhibitor therapy.

A method of treating a tumor in a subject, which tumor comprises MYC translocation error or a MYC amplification error, comprising administering to the subject an amount of a $RAS^{MULTI}$ inhibitor and an amount of a TEAD inhibitor effective to treat a tumor comprising a MYC translocation error or a MYC amplification error.

A method of treating a tumor having an elevated MYC copy number in a subject comprising administering to the tumor an amount of a $RAS^{MULTI}$ inhibitor and an amount of a TEAD inhibitor, effective to treat a tumor having an elevated MYC copy number.

DETAILED DESCRIPTION OF THE INVENTION

Figures 1A, 1B, 1C, 1D, 1E, 1F, 1G, 1H, 1I:
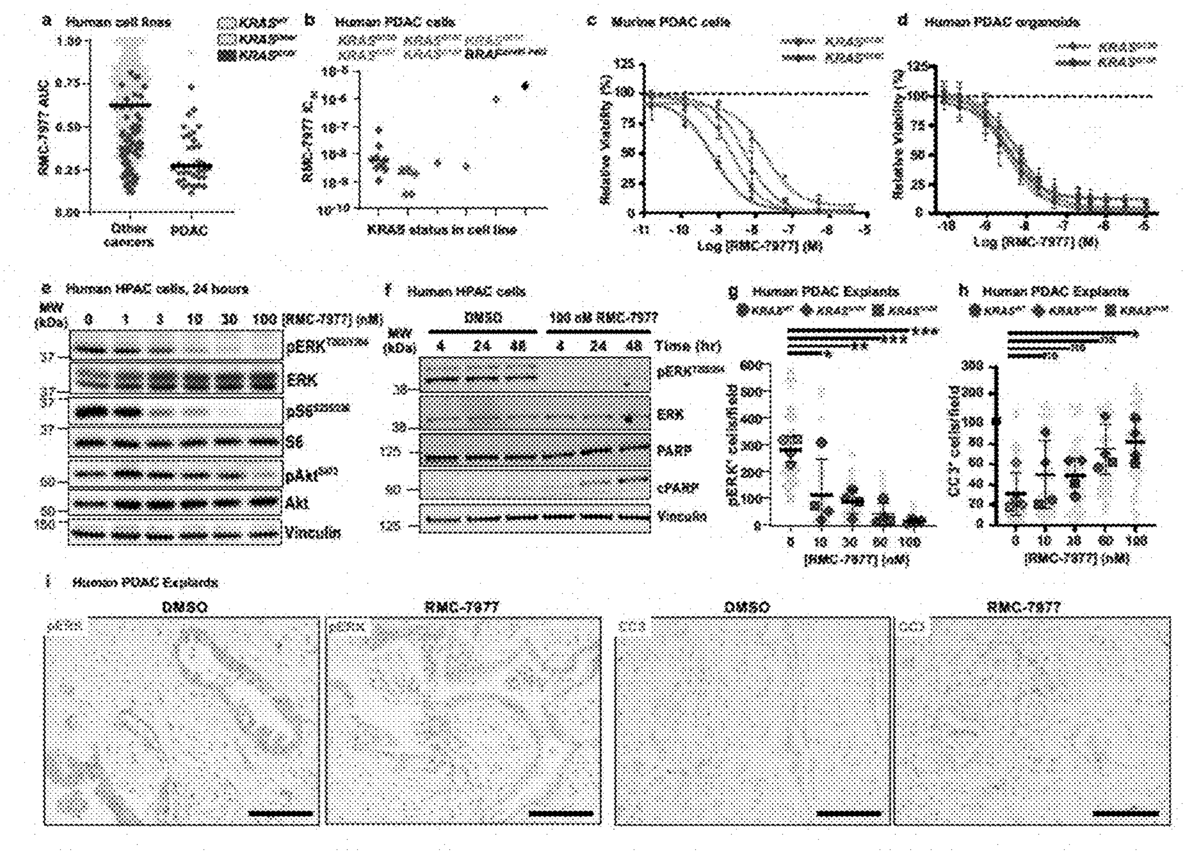
FIGS. 1A-1I. RMC-7977 demonstrates potent anti-tumor activity in in vitro and ex vivo models of PDAC. (a) PRISM multiplex cell line screening testing changes in viability of 796 cancer cell lines in response to RMC-7977 treatment. Cell line viability was plotted as Area Under Curve (AUC) values. KRAS status indicated by color of the symbol. Horizontal lines indicate median. (b) Viability levels shown as IC50 values of human PDAC cell lines with KRASG12X (HPAF-II, HuP-T4, MIA PaCa-2 and PSN-1), KRASQ61H (Hs 766T), and BRAFΔV487-P492 (BxPC-3) mutations treated with indicated concentrations of RMC-7977 for 5 days. (c) Viability levels of murine PDAC lines with KRASG12X (4662-G12D, 4662-G12C, 6419c5, 2838c3) mutations treated with indicated concentrations of RMC-7977 for 72 hours. (d) Viability levels of human PDAC organoids with KRASG12D (PF0108_T1, PF0402_T1, PF0405_T1, PF0562_T1, PF0575_T1) and KRASG12R (PF0332_T1) mutations treated with indicated concentrations of RMC-7977 for 6 days. Data points in (b, c, d) represent the mean of technical 2-3 replicates normalized to DMSO control. Error bars indicate s.d. KRAS mutations are indicated by curve colors. (e) Western blots of HPAC cells treated with DMSO or range of RMC-7977 concentrations (1-100 nM) for 24 hours. Protein levels phospho-ERKT202/204, total ERK, phospho-pS6S235/236, total S6, phospho-AktS473 and total Akt were analyzed. Vinculin was used as loading control. (f) Western blots of HPAC cells treated with DMSO or RMC-7977 (100 nM) for indicated time points. Protein levels phospho-ERKT202/204, total ERK, total PARP and cleaved PARP were analyzed. Vinculin was used as loading control. (g-i) Ex vivo human PDAC explants treated with DMSO or a range of RMC-7977 concentrations (10-100 nM) for 24 hr (n=4). (g,h) Quantification of IHC images of explants stained for (g) phospho-ERKT202/204 and (h) CC3. Analysis based on 5-15 fields of view (light shade), averaged per explant slice (dark shade) compared by one-way ANOVA test with Tukey correction (*, $p<0.05$; , $p<0.01$; *, $p<0.001$). Error bars indicate s.d. KRAS mutations are indicated by symbol shapes. (i) Representative IHC images of phosho-ERKT202/204 and CC3 staining of explants treated with DMSO or RMC-7977 (100 nM). Scale bars=50 m.

A method of treating a tumor resistant to a $RAS^{MULTI}$ inhibitor therapy comprising (i) identifying or having identified the tumor resistant to a $RAS^{MULTI}$ inhibitor therapy as having (a) a MYC copy number higher than a predetermined reference value and/or (b) a JUN copy number higher than a predetermined reference value; and (ii) administering to a tumor so-identified in (i) an amount of a $RAS^{MULTI}$ inhibitor and an amount of a TEAD inhibitor, effective to treat a tumor resistant to a $RAS^{MULTI}$ inhibitor therapy.

A method of treating a tumor in a subject comprising administering to the subject an amount of a $RAS^{MULTI}$ inhibitor and an amount of a TEAD inhibitor, effective to treat a tumor.

A method of treating a tumor resistant to a $RAS^{MULTI}$ inhibitor therapy comprising administering to a tumor so-identified an amount of a $RAS^{MULTI}$ inhibitor and an amount of a TEAD inhibitor, effective to treat a tumor resistant to a $RAS^{MULTI}$ inhibitor therapy.

In embodiments, the tumor has a MYC copy number higher than a predetermined reference value. In embodiments, the $RAS^{MULTI}$ inhibitor is a small molecule mutation-agnostic RAS inhibitor or small molecule $RAS^{MULTI}$ inhibitor which binds to GTP-bound RAS.

In embodiments, the tumor has a JUN copy number higher than a predetermined reference value.

In embodiments, the method further comprises identifying, or having identified, the tumor as having a MYC copy number higher than a predetermined reference value.

Techniques to measure copy number variants are known in the art, including commercially available services. A physician or other medical-related personnel can have the CNV analyzed/identified by a commercial service, for example. The physician or other medical-related personnel or institution can perform the analysis to identify the tumor has having a high copy number inhouse also. Microarray-based CNV analysis and next-generation sequencing (NGS) CNV analysis are common techniques. SMASH is another known method. The NGS data can be analyzed via, for example, read-pair, split-read, read-depth or assembly analysis. Copy numbers are compared to predetermined or defined standards to determine if the copy number is increased relative to a normal tissue or to, for example, a cancer or tumor of the same type being analyzed wherein the cancer is not resistant to $RAS^{MULTI}$ inhibitor treatment. In embodiments, the CNV can be measured relative to an earlier-obtained sample from said tumor, either prior to or early in $RAS^{MULTI}$ inhibitor treatment.

In embodiments, the resistance is acquired resistance. In embodiments, the resistance is primary resistance. Resistance to cancer therapies has been a commonly observed phenomenon in clinical practice and is known in the art. See, e.g., Lei et al. (MedComm 2023 May 22; 4(3):e265. doi: 10.1002 mco2.265).

In embodiments, the tumor is a tumor of a pancreatic tissue. In embodiments, the tumor is a Pancreatic ductal adenocarcinoma (PDAC).

In embodiments, the tumor is a RAS-mutated cancer. In embodiments, the RAS-mutated cancer is a colon, intestinal, lung, biliary, ovarian, or endometrial cancer.

In embodiments, the subject is not treated with a mutation-specific RAS inhibitor or a non-$RAS^{MULTI}$ inhibitor. Mutation-specific RAS inhibitors, e.g., for G12C or G12D mutation, are known in the art.

In embodiments, the predetermined reference value is determined as an average MYC copy number relative to that of a normal diploid genome of the same tissue type as the tumor.

In embodiments, the tumor is a PDAC and the predetermined reference value is an average MYC copy number in PDAC tumor cells not resistant to pan-RAS inhibitor therapy.

A predetermined reference value is a value decided or obtained, usually beforehand, as a control. The concept of a control is well-established in the field, and can be determined, in a non-limiting example, empirically from, e.g., non-afflicted subjects (versus afflicted subjects, including afflicted subjects having different grades of the relevant affliction), or a non-afflicted sample, e.g., a tumor that is not resistant to $RAS^{MULTI}$ inhibitors and may be normalized as desired (in non-limiting examples, for volume, mass, age, location, gender) to negate the effect of one or more variables.

In embodiments, the TEAD inhibitor is a pan-TEAD inhibitor.

In embodiments, the subject has previously been treated with a $RAS^{MULTI}$ inhibitor but not a TEAD inhibitor.

In embodiments, the subject has not previously been treated with a $RAS^{MULTI}$ inhibitor.

A method of treating a tumor in a subject, which tumor comprises MYC translocation error or a MYC amplification error, comprising administering to the subject an amount of a $RAS^{MULTI}$ inhibitor and an amount of a TEAD inhibitor effective to treat a tumor comprising a MYC translocation error or a MYC amplification error.

In embodiments, the methods further comprise identifying, or having identified, the tumor as comprising a MYC translocation error or a MYC amplification error prior to administering the amount of a $RAS^{MULTI}$ inhibitor and a TEAD inhibitor.

In embodiments, the tumor comprises a MYC translocation error and is a B-cell lymphoma.

In embodiments, the tumor comprises a MYC amplification error and is an ovarian, breast, colorectal, pancreatic, gastric, or uterine cancer.

In embodiments, the tumor is a PDAC.

In embodiments, the subject is not treated with a mutation-specific RAS inhibitor.

In embodiments, the TEAD inhibitor is a pan-TEAD inhibitor.

In embodiments, the subject has previously been treated with a $RAS^{MULTI}$ inhibitor but not a TEAD inhibitor.

In embodiments, the subject has not previously been treated with a $RAS^{MULTI}$ inhibitor.

In embodiments, the subject has not been, and/or is not being, treated with an inhibitor of a MYC, MYCL, or MYCN protein.

In embodiments, the subject has not been, and/or is not being, treated with an inhibitor of MYC transcription or expression.

In embodiments, the MYC is c-MYC, l-MYC, or n-MYC.

A method of treating a tumor having an elevated MYC copy number in a subject comprising administering to the tumor an amount of a $RAS^{MULTI}$ inhibitor and an amount of a TEAD inhibitor, effective to treat a tumor having an elevated MYC copy number.

In embodiments, the method further comprises identifying, or having identified, the tumor as having an elevated MYC copy number.

In embodiments, the elevated MYC copy number is a copy number higher than a predetermined reference value.

In embodiments, the $RAS^{MULTI}$ inhibitor is RMC-7977 or an analog thereof.

In embodiments, the analog is RMC-6236 or RMC-6291.

In embodiments, the RMC-7977 has the structure:

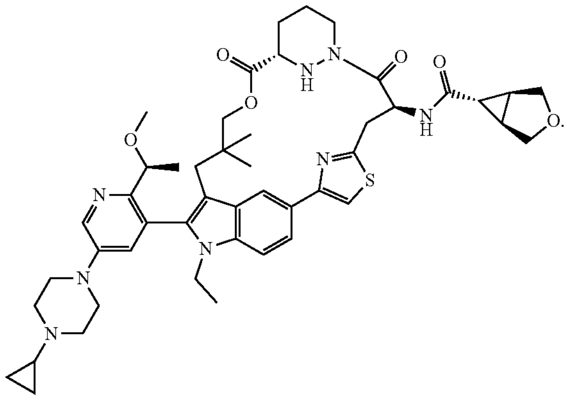 [SMILES: CCn1c(-c2cc(N3CCN(C4CC4)CC3)cnc2[C@H](C)OC)c2c3cc(ccc31)-c1csc(n1)C[C@H](NC(=O)[C@H]1[C@@H]3COC[C@@H]31)C(=O)N1CCC[C@H](N1)C(=O)OCC(C)(C)C2]

In embodiments, the analog has the structure:

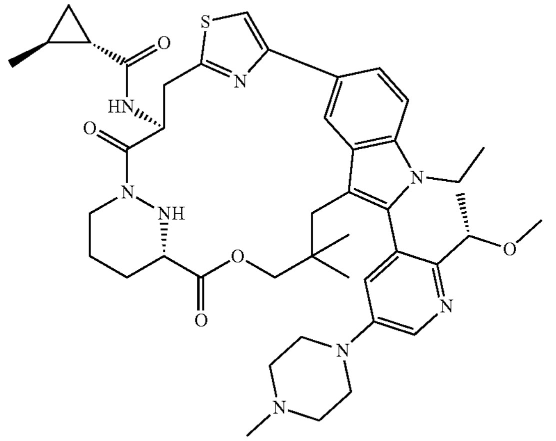

or is (1S,2S)—N-((63S,4S,Z)-11-ethyl-12-(2-((S)-1-methoxyethyl)-5-(4-methylpiperazin-1-yl)pyridin-3-yl)-10,10-dimethyl-5,7-dioxo-61,62,63,64,65,66-hexahydro-11H-8-oxa-2(4,2)-thiazola-1(5,3)-indola-6(1,3)-pyridazinacycloundecaphane-4-yl)-2-methylcyclopropane-1-carboxamide. In embodiments, the analog is RMC-6236.

In embodiments, the analog has the structure:

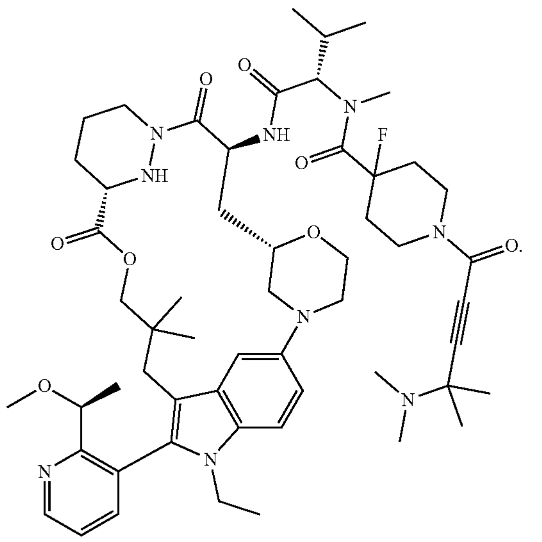 [SMILES: CCn1c(-c2cccnc2[C@H](C)OC)c2c3cc(ccc31)N1CCO[C@@H](C[C@H](NC(=O)[C@H](C(C)C)N(C)C(=O)C3(F)CCN(C(=O)C#CC(C)(C)N(C)C)CC3)C(=O)N3CCC[C@H](N3)C(=O)OCC(C)(C)C2)C1]

In embodiments, the analog is RMC-6291.

In embodiments, the RAS is encoded by a gene which is KRAS, NRAS, or HRAS.

In embodiments, the RAS is human.

A method of treating a tumor in a subject, which tumor comprises MYC translocation error or a MYC amplification error, comprising administering to the subject an amount of a RAS inhibitor and an amount of a TEAD inhibitor effective to treat a tumor comprising a MYC translocation error or a MYC amplification error.

In embodiments the RAS inhibitor is a $RAS^{MULTI}$ inhibitor.

In embodiments the RAS inhibitor is not a $RAS^{MULTI}$ inhibitor. In embodiments the RAS inhibitor which is not a $RAS^{MULTI}$ inhibitor is

RMC-9805

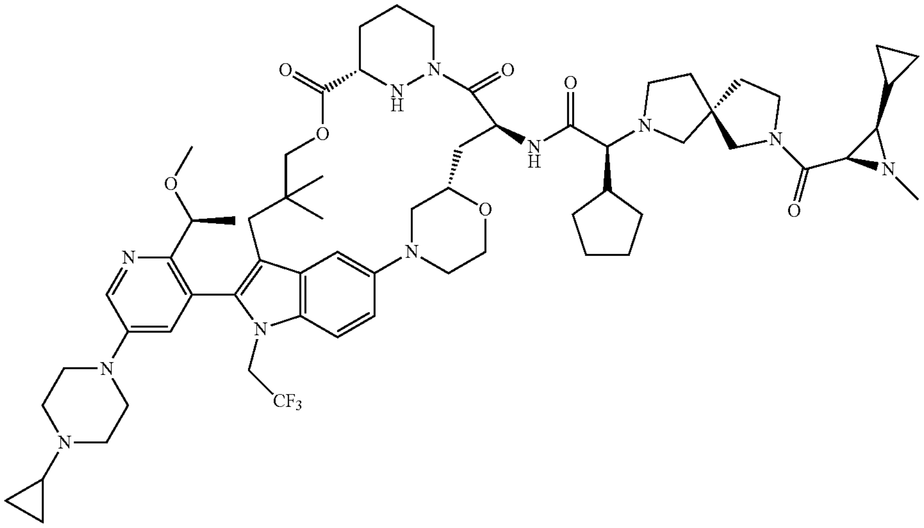

, or

-continued

RMC-4998

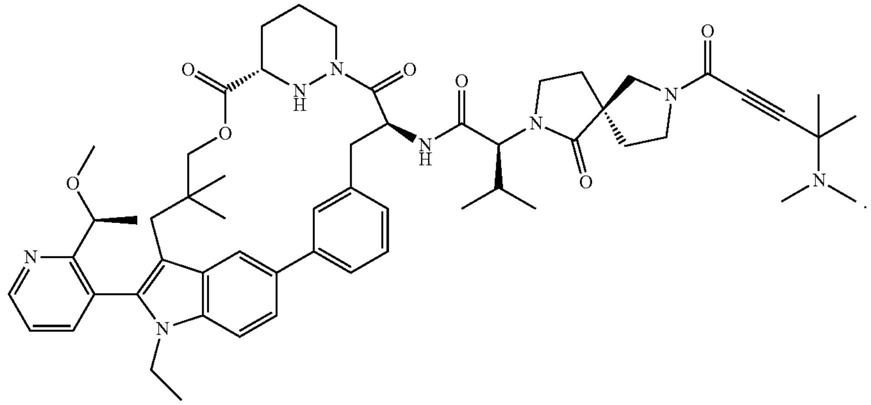

In embodiments of the methods, the TEAD inhibitor is TEAD K-975; N-(1-((3-(trifluoromethyl)phenyl)amino)-2,3-dihydro-1H-inden-5-yl)acrylamide: N-(1-(4-(trifluoromethyl)phenyl)-1H-indol-5-yl)acrylamide; N-(3-(methoxymethyl)-1-(4-(trifluoromethyl)phenyl)-1H-indol-5-yl) acrylamide; N-(3-methyl-1-(3-(trifluoromethyl)benzyl)-1H-indol-5-yl)acrylamide; N-(3-(((trans)-4-(trifluoromethyl) cyclohexyl)oxy)-2,3-dihydro-1H-inden-5-yl)acrylamide; N-(3-((3,4-difluorophenyl)amino)-2,3-dihydro-1H-inden-5-yl)acrylamide; N-(3-(4-(trifluoromethyl)phenoxy)-2,3-dihydro-1H-inden-5-yl)acrylamide, or is IAG933 having the structure:

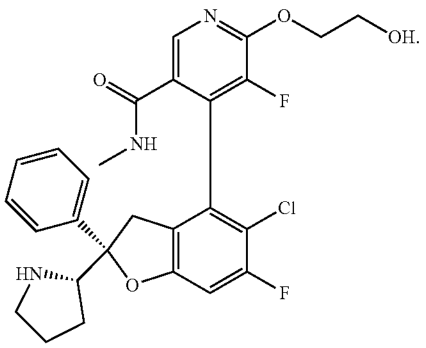 [SMILES: CNC(=O)c1cnc(OCCO)c(F)c1-c1c(Cl)c(F)cc2c1C[C@](c1ccccc1)([C@@H]1CCCN1)O2]

In embodiments, the TEAD inhibitor is selected from those described in WO 2020/243415, those described in WO 2020/243423, or those described in U.S. Pat. No. 11,274,082, the contents of each which are herein incorporated by reference in their entirety.

In embodiments, the ratio of the amount of the $RAS^{MULTI}$ inhibitor to the amount of the TEAD inhibitor is synergistic in killing or inhibiting the tumor.

In embodiments, the mean synergy (delta score) is 5.0 or above. In embodiments, the mean synergy (delta score) is one of 6.0, 7.0, 8.0, 9.0, or 10.0 or above. In embodiments, the mean synergy (delta score) is 12 or above. In embodiments, the mean synergy (delta score) is 13 or above. In embodiments, the mean synergy (delta score) is 14 or above. In embodiments, the mean synergy (delta score) is 15 or above. In embodiments, the mean synergy (delta score) is 20 or above.

In embodiments, the $RAS^{MULTI}$ inhibitor-resistant tumor has a Myc has a copy number ratio of 1.5 or greater. In embodiments, the $RAS^{MULTI}$ inhibitor-resistant tumor has a Myc has a copy number ratio of 2.0 or greater. In embodiments, the $RAS^{MULTI}$ inhibitor-resistant tumor has a Jun has a copy number ratio of 1.5 or greater. In embodiments, the $RAS^{MULTI}$ inhibitor-resistant tumor has a Jun has a copy number ratio of 2.0 or greater. In embodiments, the $RAS^{MULTI}$ inhibitor-resistant tumor further has a Pik3c2 has a copy number ratio of 1.5 or greater. In embodiments, the $RAS^{MULTI}$ inhibitor-resistant tumor further has a Pik3c2b has a copy number ratio of 2.0 or greater. In embodiments, the $RAS^{MULTI}$ inhibitor-resistant tumor further has a Pik3ca has a copy number ratio of 2.0 or greater. In embodiments, the $RAS^{MULTI}$ inhibitor-resistant tumor further has a Pik3ca has a copy number ratio of 5.0 or greater. Ratios can be measured relative to any desired control, including non-cancerous cells of the same tissue in which the tumor is present, non-cancerous cells of the same subject, cells initially obtained from the tumor prior to any $RAS^{MULTI}$ inhibitor treatment, predefined standard numbers for comparable tumors or comparable subjects etc.

In preferred embodiments the Myc is a human Myc. Human Myc gene is known in the art. Exemplary Myc embodiments include HGNC: 7553, NCBI Gene: 4609, Ensembl: ENSG00000136997, OMIM®: 190080, and UniProtKB or Swiss-Prot: P01106.

In embodiments, the Myc is human and is on chromosome 8. In embodiments, the ratio of the amount of the $RAS^{MULTI}$ inhibitor to the amount of the TEAD inhibitor is not antagonistic in killing or inhibiting the tumor.

In embodiments, the $RAS^{MULTI}$ inhibitor is a $RAS^{MULTI}$ (ON) inhibitor. In embodiments the $RAS^{MULTI}$ inhibitor is not a selective G12C or G12D inhibitor.

$RAS^{MULTI}$ inhibitors as used in the art are inhibitors that inhibit multiple RAS types including mutated and non-mutated forms, and which are not limited to only inhibiting a specific mutation of RAS (for example, as G12C- or G12D-specific RAS inhibitors are). A $RAS^{MULTI}$ (ON) inhibitor is a $RAS^{MULTI}$ inhibitor which inhibits GTP-bound forms of RAS. Mutation-agnostic RAS inhibitors are $RAS^{MULTI}$ inhibitors.

The present invention provides a method of resensitizing a RAS-related tumor to $RAS^{MULTI}$(ON) inhibitors by administering to the tumor a $RAS^{MULTI}$(ON) inhibitor in conjunction with a TEAD inhibitor. In embodiments, the method further comprises identifying or having identified the tumor as needing desensitizing to $RAS^{MULTI}$(ON) inhibitor treatment.

In embodiments, a $RAS^{MULTI}$(ON) inhibitor is an inhibitor of the active GTP-bound forms of KRAS, HRAS and/or NRAS, with affinity for both mutant and wild-type variants, i.e. not only for a specific mutant. In embodiments, a $RAS^{MULTI}$ (ON) inhibitor is an inhibitor of the active GTP-bound mutant and wild type forms of human KRAS.

In embodiments, the $RAS^{MULTI}$(ON) inhibitor is a small molecule. In embodiments, the TEAD inhibitor is a small molecule.

The compounds of the present invention include all hydrates, solvates, and complexes of the compounds used by this invention. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. The compounds described in the present invention are in racemic form or as individual enantiomers. The enantiomers can be separated using known techniques, such as those described in Pure and Applied Chemistry 69, 1469-1474, (1997) IUPAC. In cases in which compounds have unsaturated carbon-carbon double bonds, both the cis (Z) and trans (E) isomers are within the scope of this invention.

The compounds of the subject invention may have spontaneous tautomeric forms. In cases wherein compounds may exist in tautomeric forms, such as keto-enol tautomers, each tautomeric form is contemplated as being included within this invention whether existing in equilibrium or predominantly in one form.

In the compound structures depicted herein, hydrogen atoms are not shown for carbon atoms having less than four bonds to non-hydrogen atoms. However, it is understood that enough hydrogen atoms exist on said carbon atoms to satisfy the octet rule.

This invention also provides isotopic variants of the compounds disclosed herein, including wherein the isotopic atom is $^{2}H$ and/or wherein the isotopic atom $^{13}C$. Accordingly, in the compounds provided herein hydrogen can be enriched in the deuterium isotope. It is to be understood that the invention encompasses all such isotopic forms.

It is understood that the structures described in the embodiments of the methods hereinabove can be the same as the structures of the compounds described hereinabove.

It is understood that where a numerical range is recited herein, the present invention contemplates each integer between, and including, the upper and lower limits, unless otherwise stated.

Except where otherwise specified, if the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{3}C$, or $^{14}C$. Furthermore, any compounds containing $^{13}C$ or 14C may specifically have the structure of any of the compounds disclosed herein.

It will also be noted that any notation of a hydrogen in structures throughout this application, when used without further notation, are intended to represent all isotopes of hydrogen, such as $^{1}H$, $^{2}H$, or $^{3}H$. Furthermore, any compounds containing $^{2}H$ or $^{3}H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano, carbamoyl and aminocarbonyl and aminothiocarbonyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

The compounds of the present invention may also form salts with basic amino acids such a lysine, arginine, etc. and with basic sugars such as N-methylglucamine, 2-amino-2-deoxyglucose, etc. and any other physiologically non-toxic basic substance.

As used herein, "administering" an agent may be performed using any of the various methods or delivery systems well known to those skilled in the art. The administering can be performed, for example, orally, parenterally, intraperitoneally, intravenously, intraarterially, transdermally, sublingually, intramuscularly, rectally, transbuccally, intranasally, liposomally, via inhalation, vaginally, intraocularly, via local delivery, subcutaneously, intraadiposally, intraarticularly, intrathecally, into a cerebral ventricle, intraventricularly, intratumorally, into cerebral parenchyma or intraparenchymally.

The compounds used in the method of the present invention may be administered in various forms, including those detailed herein. The treatment with the compound may be a component of a combination therapy or an adjunct therapy. The combination therapy can be sequential therapy, where the patient is treated first with one drug and then the other, or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier as are slow-release vehicles.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antitumor agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or topically onto a site of disease or lesion, all using dosage forms well known to those of ordinary skill in the pharmaceutical arts.

The compounds used in the method of the present invention can be administered in admixture with suitable pharmaceutical diluents, extenders, excipients, or in carriers such as the novel programmable sustained-release multi-compartmental nanospheres (collectively referred to herein as a pharmaceutically acceptable carrier) suitably selected with respect to the intended form of administration and as consistent with conventional pharmaceutical practices. The unit will be in a form suitable for oral, nasal, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamellar vesicles, and multilamellar vesicles. Liposomes can be formed from a variety of phospholipids such as lecithin, sphingomyelin, proteolipids, protein-encapsulated vesicles or from cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropylmethacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials such as solutol and/or ethanol to make them compatible with the type of injection or delivery system chosen.

The compounds and compositions of the present invention can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by topical administration, injection or other methods, to the afflicted area, such as a wound, including ulcers of the skin, all using dosage forms well known to those of ordinary skill in the pharmaceutical arts.

Specific examples of pharmaceutically acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

The active ingredient can be administered orally in solid dosage forms, such as capsules, tablets, powders, and chewing gum; or in liquid dosage forms, such as elixirs, syrups, and suspensions, including, but not limited to, mouthwash and toothpaste. It can also be administered parentally, in sterile liquid dosage forms.

Solid dosage forms, such as capsules and tablets, may be enteric-coated to prevent release of the active ingredient compounds before they reach the small intestine. Materials that may be used as enteric coatings include, but are not limited to, sugars, fatty acids, proteinaceous substances such as gelatin, waxes, shellac, cellulose acetate phthalate (CAP), methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), and methyl methacrylate-methacrylic acid copolymers.

The compounds and compositions of the invention can be coated onto stents for temporary or permanent implantation into the cardiovascular system of a subject.

Variations on those general synthetic methods will be readily apparent to those of ordinary skill in the art and are deemed to be within the scope of the present invention.

Each embodiment disclosed herein is contemplated as being applicable to each of the other disclosed embodiments. Thus, all combinations of the various elements described herein are within the scope of the invention.

Results

As >90% of human pancreatic ductal adenocarcinoma (PDAC) cases are driven by activating mutations in KRAS, we assessed the therapeutic potential of a $RAS^{MULTI}$(ON) inhibitor using RMC-7977 in a comprehensive range of PDAC models, including human and murine cell lines, patient-derived organoids, human PDAC explants, subcutaneous and orthotopic cell-line or patient-derived xenografts, syngeneic allografts, and genetically engineered mouse models. We observed broad and pronounced anti-tumor activity across these models following direct RAS inhibition at exposures that were well-tolerated in vivo. Pharmacological analyses revealed divergent responses to RMC-7977 in tumor versus normal tissues. Treated tumors exhibited waves of apoptosis along with sustained proliferative arrest whereas normal tissues underwent only transient decreases in proliferation, with no evidence of apoptosis. In the autochthonous KPC model, RMC-7977 treatment resulted in a profound extension of survival followed by on-treatment relapse. Analysis of relapsed tumors identified Myc copy number gain as a prevalent candidate resistance mechanism, which could be overcome by combinatorial Tead inhibition. Together, these data establish a strong preclinical rationale for the use of broad-spectrum RAS inhibition in the setting of PDAC and identify a combination therapeutic regimen to overcome monotherapy resistance.

Activating mutations in the three isoforms of the RAS oncogene (HRAS, KRAS, and NRAS) are associated with approximately 20-30% of human cancers[1,2]. KRAS is the predominant isoform mutated in cancer, including in more than 90% of pancreatic ductal adenocarcinomas (PDAC), a leading cause of cancer mortality in the United States[3] and globally. Though RAS proteins were long regarded as "undruggable", recent advances have led to the development and approval of agents that target one specific RAS variant, $KRAS_{G12C}$[4,5]. This strategy has shown promising efficacy in $KRAS^{G12C}$-mutant tumors, including the small fraction (~1%) of PDAC cases harboring this allele[6-7]. However, resistance arises quickly in the majority of patients treated with KRASG12C inhibitors and various alterations that reactivate RAS signaling both directly and indirectly have been identified in patients who have progressed on these inhibitors[8-10]. The FDA-approved $KRAS^{G12C}$ inhibitors, as well as two recently-described inhibitors (one targeting $KRAS^{G12D}$ and one with broader KRAS mutant specificity), selectively target the inactive, GDP-bound state of mutant KRAS and are consequently vulnerable to mechanisms of resistance that increase levels of GTP-bound KRAS or wild type HRAS and NRAS, including activation of upstream RTKs[11-13]. Here we used the tool compound, RMC-7977, to evaluate the pharmacology and anti-tumor activity of ($RAS^{MULTI}$ (ON)) inhibitors in preclinical models of PDAC. This mechanistically-distinct class of tri-complex RAS inhibitors, which includes the investigational agent RMC-6236, exhibits selectivity for the active, GTP-bound forms of all RAS isoforms, mutant and WT. Holderfield et al.[14] describes the discovery of RMC-7977 along with evidence that this agent can overcome some forms of acquired resistance to inhibitors that target GDP-bound RAS isoforms. RMC-6236, is currently in early clinical evaluation in patients with advanced solid tumors harboring RAS mutations (NCT05379985).

The singular role of mutant KRAS in PDAC oncogenesis has inspired myriad strategies for therapeutic intervention. Efforts to target prenylation of RAS proteins, upstream receptors, and downstream signaling were stymied by functional redundancies and compensatory feedback mechanisms[1,9,10,15-16]. Combinatorial strategies targeting multiple pathway effectors or compensatory responses can drive greater activity, but generally at the cost of reduced tolerability. Studies of $Kras^{G12D}$ gene deletion in engineered mouse models demonstrated that mutant KRAS plays an essential role in the maintenance of PDAC[17-19]. This was recently bolstered by preclinical evidence showing tumor regressions in PDAC models following pharmacologic inhibition of $KRAS_{G12D}$ [11,12]. The development of RAS inhibitors with broader specificity has the potential to benefit the majority of PDAC patients while countering a wider range of resistance mechanisms. However, given the critical role of RAS proteins in normal tissue homeostasis[20,21], a prevailing question is whether broad inhibition of RAS activity in tumors can be implemented with a suitable therapeutic index[22].

Figures 7A, 7B, 7C, 7D, 7E, 7F, 7G:
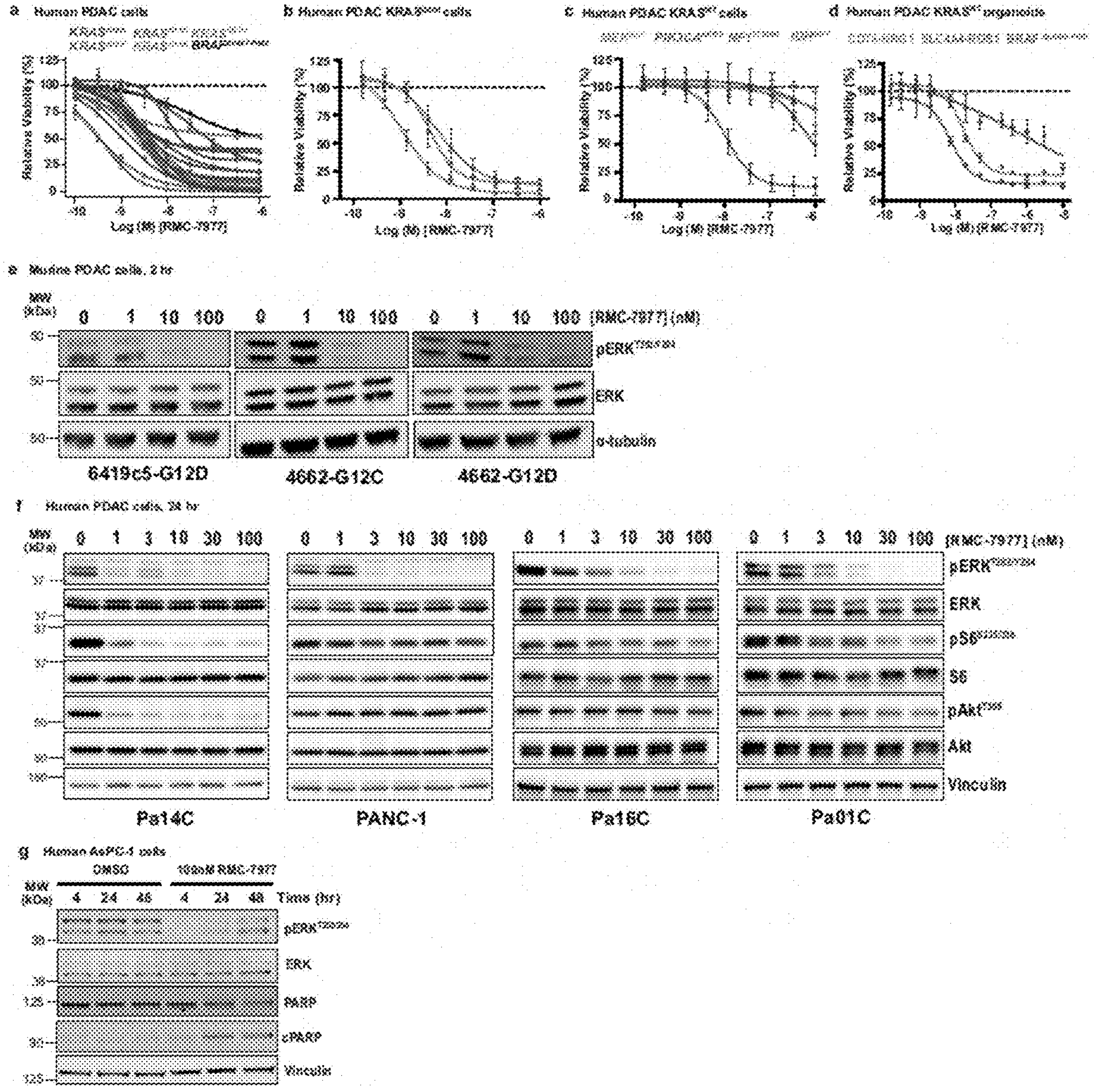
FIGS. 7A-7G: (a) Viability levels of human PDAC cell lines with KRASG12X (AsPC-1, HPAC, Pane 05.04, PANC-1, Pane 10.05, PL45, SU.86.86, SW-1990, KP-4, HPAF-II, Capan-1, Capan-2, CFPAC-1, Pane 03.27, HuP-T4, MIA PaCa-2 and PSN-1), KRASQ61H (Hs 766T), and BRAFΔV487-P492 (BxPC-3) mutations treated with indicated concentrations of RMC-7977 for 5 days. Data points represent the mean of technical replicates normalized to DMSO control. Error bars indicate s.d. KRAS mutations are indicated by curve colors. (b,c) Viability levels of human PDAC cell lines with (b) KRASQ61H (Pa02C, T3M-4, UM147) mutation or (c) KRASWT (hF39, hF43, PaCaDD-137, PaCaDD-165) treated with DMSO or indicated concentrations of RMC-7977 for 5 days. Data points represent the mean of technical replicates normalized to DMSO control. Error bars indicate s.d. (d) Viability levels of human PDAC organoids with KRASWT (PF0124_T1, PF0202_T1, PF0344_T1) treated with DMSO or indicated concentrations of RMC-7977 for 6 days. Data points represent the mean of technical replicates normalized to DMSO control. Error bars indicate s.d. (e) Representative Western Blot images for three murine PDAC cell lines treated with DMSO or range of RMC-7977 concentrations (1-100 nM) for 2 hours. Protein levels of phospho-ERKT202/204 and total ERK were analyzed. Alpha-(α)-tubulin was used as loading control. (f) Representative Western Blot images for human PDAC cell lines treated with DMSO or range of RMC-7977 concentrations (1-100 nM) for 24 hours. Protein levels of phospho-ERKT202/204, total ERK, phospho-pS6S235/236 total S6, phospho-AktT308 and total Akt were analyzed. Vinculin was used as loading control. (g) Representative Western Blot images for AsPC-1 cell line treated with DMSO or RMC-7977 (100 nM) for indicated timepoints. Protein levels of phospho-ERKT202/204, total ERK, total PARP and cleaved PARP were analyzed. Vinculin was used as loading control.

Brief Summary of the RMC-7977 Exhibits Broad Anti-Cancer Activity in PDAC Models KRAS mutations in PDAC occur principally at codon 12 (KRASG12X) with infrequent occurrence of mutations at codons 61 (6-7%) and 13 (1%)[23,24]. Consistent with the finding that cell lines with KRASG12X mutations are particularly sensitive to RMC-7977[14], we found that human PDAC cell lines were among the most sensitive in a large scale screen of 796 human tumor cell lines using the PRISM platform (FIG. 1*a*). In concentration-response cell viability assays, RMC-7977 exhibited low nanomolar potency in most human and murine PDAC cell lines, and in Matrigel-embedded human PDAC organoids (FIG. 1*b-d*). Two human cell lines showed lower sensitivity in vitro, one harboring KRASQ61H and one with KRASWT, the latter harboring a BRAFClassII mutation predicted to be independent of RAS-GTP inhibition (FIG. 1*b*). Analysis of three additional KRASQ61H PDAC lines found low nanomolar potency for each (FIG. 7*b*) and an examination of KRASWT cell lines and organoids indicated a wider range of sensitivity that likely reflects the nature of their respective driving mutations (FIG. 7*c,d*). Western blot analyses of human and murine PDAC cell lines demonstrated reduced phosphorylation of the RAS-RAF effector proteins ERK1/2 (pERK), indicating effective inhibition of the RAS/MAPK pathway at concentrations consistent with observed GI50 values (FIGS. 1*e* and 7*d*). In human cell lines, we detected more variable inhibition of PI3K effector signaling as monitored by phosphorylation of AKT (pAKT) and S6 (pS6S235/S236), indicating some heterogeneity in the signaling responses across different lines and consistent with additional inputs (beyond direct RAS interactions) driving PI3K signaling in some contexts (FIG. 1*e* and FIG. 7*e*). Inhibition of pERK was generally durable over 48 hours in human cell lines and associated with induction of the apoptotic marker cleaved PARP (c-PARP) at later timepoints (FIG. 1*f* and FIG. 7*f*).

Multiple studies have demonstrated that various stromal cells resident in PDAC tissues can modulate the sensitivity of malignant cells to therapy[25]. To assess the potency of RMC-7977 in the context of an intact, all-human microenvironment, we employed an ex vivo human PDAC explant model[26], comprising cultured intact slices of freshly resected human PDAC tissue from patients at New York Presbyterian Hospital/Columbia University Irving Medical Center. Immunohistochemistry (IHC) performed on PDAC explants treated for 24 hours with RMC-7977 showed a concentration-dependent decrease in pERK expression with an accompanying increase in the apoptosis marker cleaved caspase 3 (CC3), with maximal changes at 100 nM, the highest concentration tested (FIG. 1*g*-*i*). Of note, one of the four explant models was found to be KRASWT and was also sensitive to RMC-7977 (FIG. 1*g*, circles). Together these data are consistent with the pharmacodynamic responses observed in isolated cell lines and 3D organoid systems and imply that the consequences of direct RAS inhibition observed in vitro are recapitulated in a complex PDAC tumor milieu. In summary, RMC-7977 consistently and potently inhibited RAS pathway signaling across KRAS-dependent PDAC cell lines (including KRASWT in some contexts), patient-derived organoids, and human tumor explants, resulting in growth attenuation and/or induction of apoptosis.

Figure 2A:
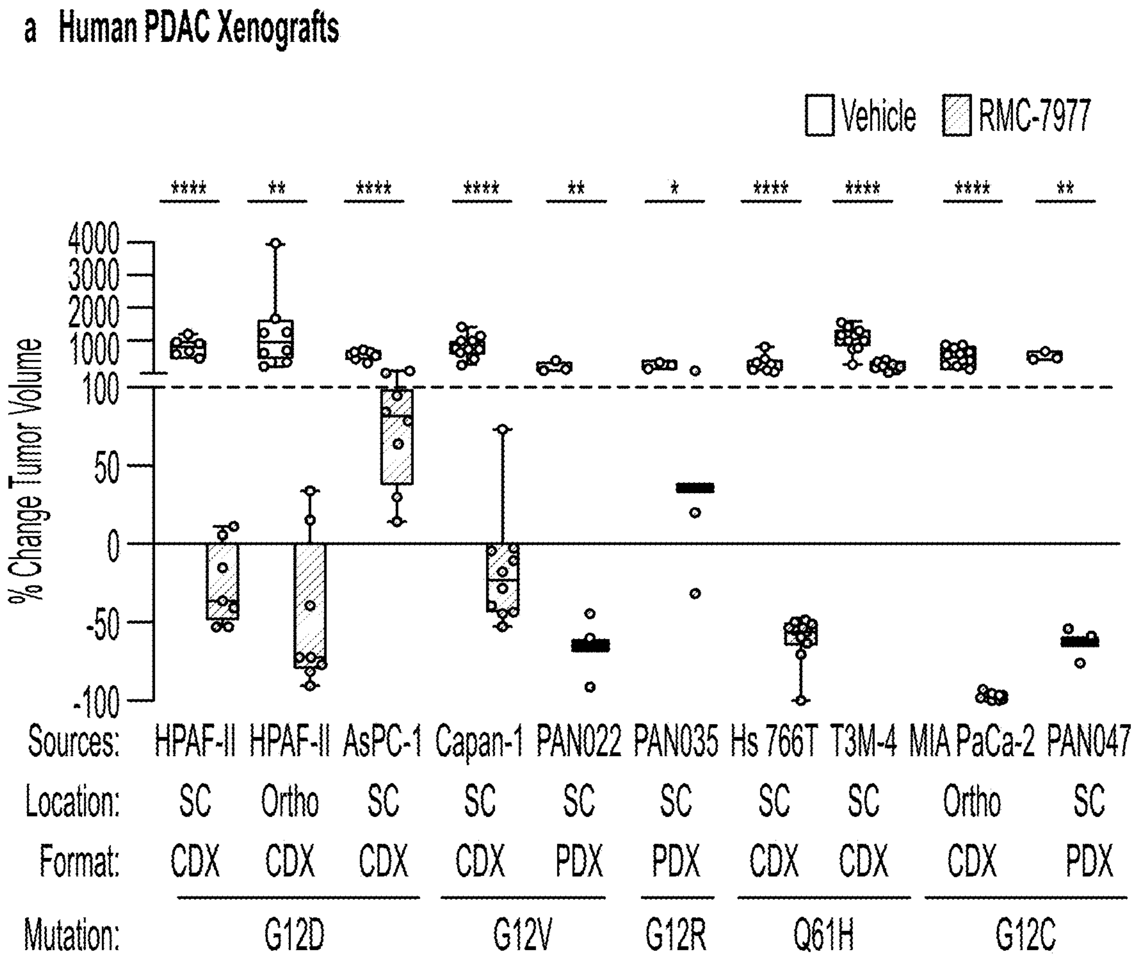
FIGS. 2A-2G: RMC-7977 exhibits anti-tumor activity in xenograft and allograft models of PDAC. (a-e) Human PDAC xenograft models implanted either subcutaneously (SC) or orthotopically (Ortho) into immunodeficient mice. Tumor-bearing mice were treated with Vehicle or RMC-7977 (10 mg/kg, po, q.d.; n=3-10) for 21-28 days. (a) Boxplot showing percent change in tumor volumes at endpoint compared with baseline at Day 0 in Vehicle and RMC-7977 treatment arms. Each symbol represents one mouse. Source and format of each cell line, KRAS mutation, and tumor locations are indicated in the graph. Study arms were compared by Student's unpaired t-test (*, $p<0.05$; , $p<0.01$; **, $p<0.0001$). (b) Representative bioluminescence images showing signal in HPAF-II orthotropic xenograft tumors at Day 0 and at Day 21 for Vehicle and RMC-7977 treatment arms. (c,d) Representative tumor growth curves for HPAF-II (c) orthotopic and (d) subcutaneous xenograft models treated with Vehicle or RMC-7977 (n=8/group), shown as percent tumor volume change from baseline over the course of treatment. Vehicle and RMC-7977 groups were compared by 2-way repeated measures ANOVA on the last measurement day of the vehicle group (*, p<0.05; **p<0.0001). Error bars indicate ±s.e.m. (e) Tolerability of RMC-7977 as assessed by percent animal body weight change from baseline over the course of treatment. Error bars indicate ±s.e.m. (f, g) KPCY-derived PDAC cell line (6499c4) was transplanted either subcutaneously or orthotopically into syngeneic mice. Tumor-bearing mice were treated with Vehicle or RMC-7977 (10 mg/kg, po, q.d.; n=9-10/group). (f) Boxplot showing changes in subcutaneous and orthotopic tumor volumes at Day 14, compared with baseline at Day 0, in Vehicle and RMC-7977 treatment arms. Groups compared by Student's unpaired t-test (*, p<0.001; ****, p<0.0001). Tumor locations as indicated in the graph. (g) Representative IHC images of Vehicle and RMC-7977-treated KPCY allograft tumors stained for phospho-ERKT202/204 and CC3. Scale bars=100 m.
Figure 2B:
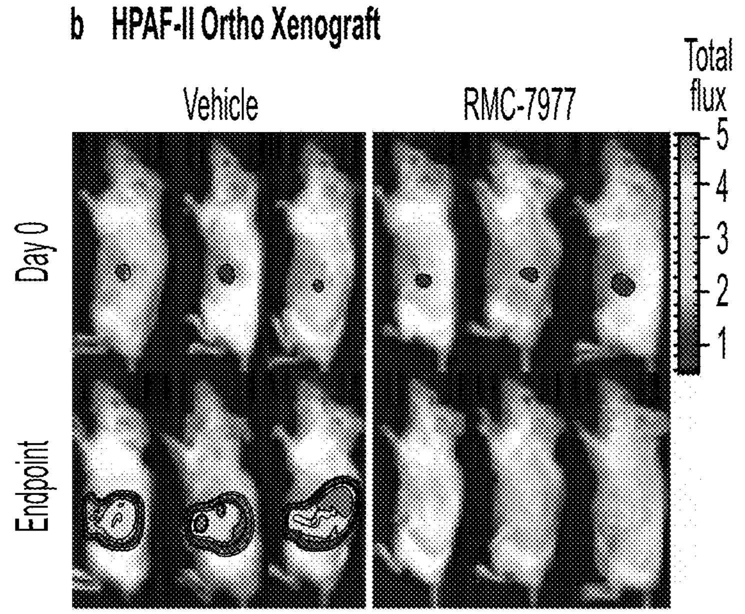
Figure 2C:
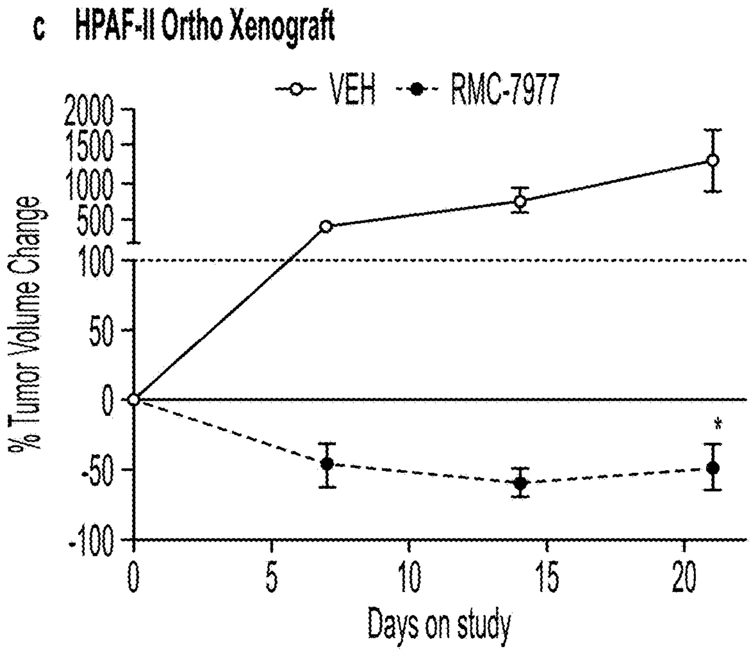
Figure 2D:
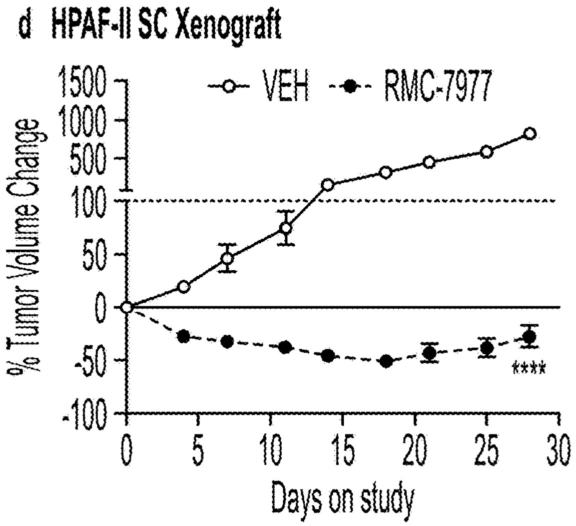
Figure 2E:
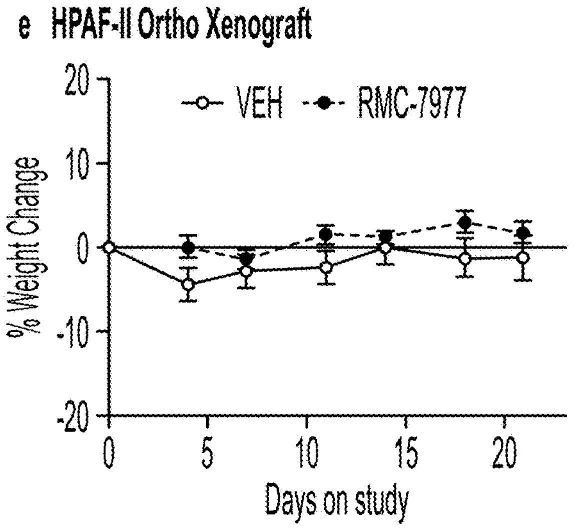

Having established the potency of RMC-7977 in cell culture models, we next evaluated the activity of RMC-7977 in vivo. We began with a panel of seven human PDAC cell line-derived xenografts (CDXs) and three patient-derived xenograft (PDX) derived from human PDAC fragments, implanted either subcutaneously (SC) or orthotopically in the pancreas (Ortho) of immune-deficient mice. RMC-7977 was administered at a daily dose of 10 mg/kg over the course of 21-28 days and resulted in significant anti-tumor activity in all 10 models. Tumor regressions were observed in 7/10 models and ranged from 30% to 98% relative to baseline volume (FIG. 2*a*-*d*, FIG. 8*a*-*i*). Interestingly, the KRASQ61H mutant HS-766T line, which showed lower sensitivity in vitro in FIG. 1*b*, was among the most responsive in CDX setting (FIG. 2*a*). Importantly, RMC-7977 was well tolerated in all 10 models, with treated animals generally exhibiting stable body weight over time (FIG. 2*e*, FIG. 8*j*-*r*).

Figure 2F:
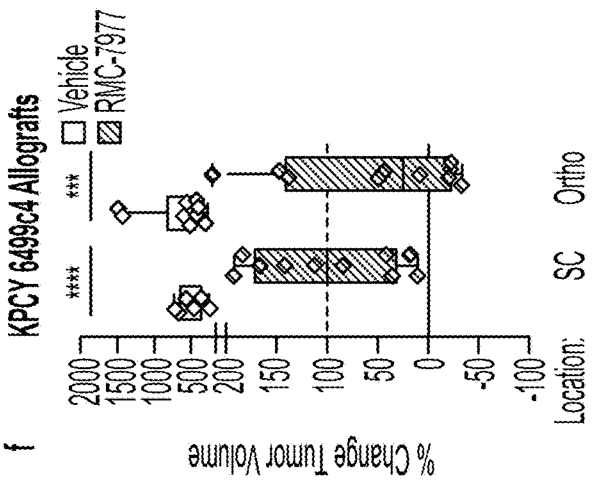
Figure 2G:
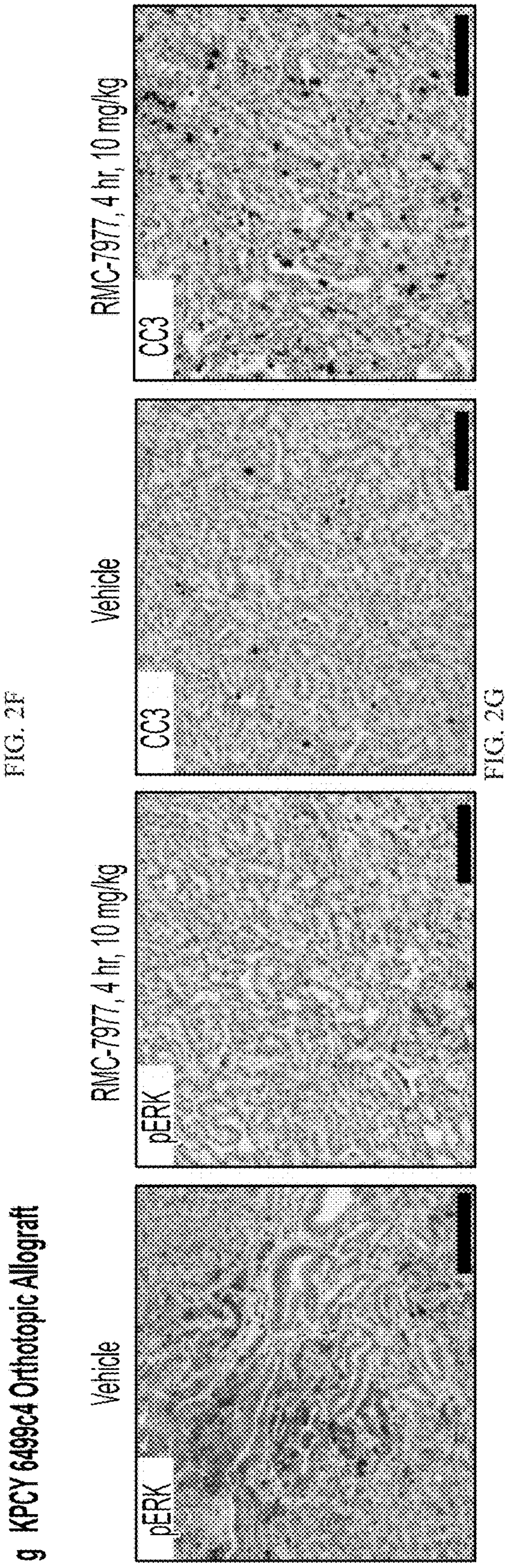
Figure 8A:
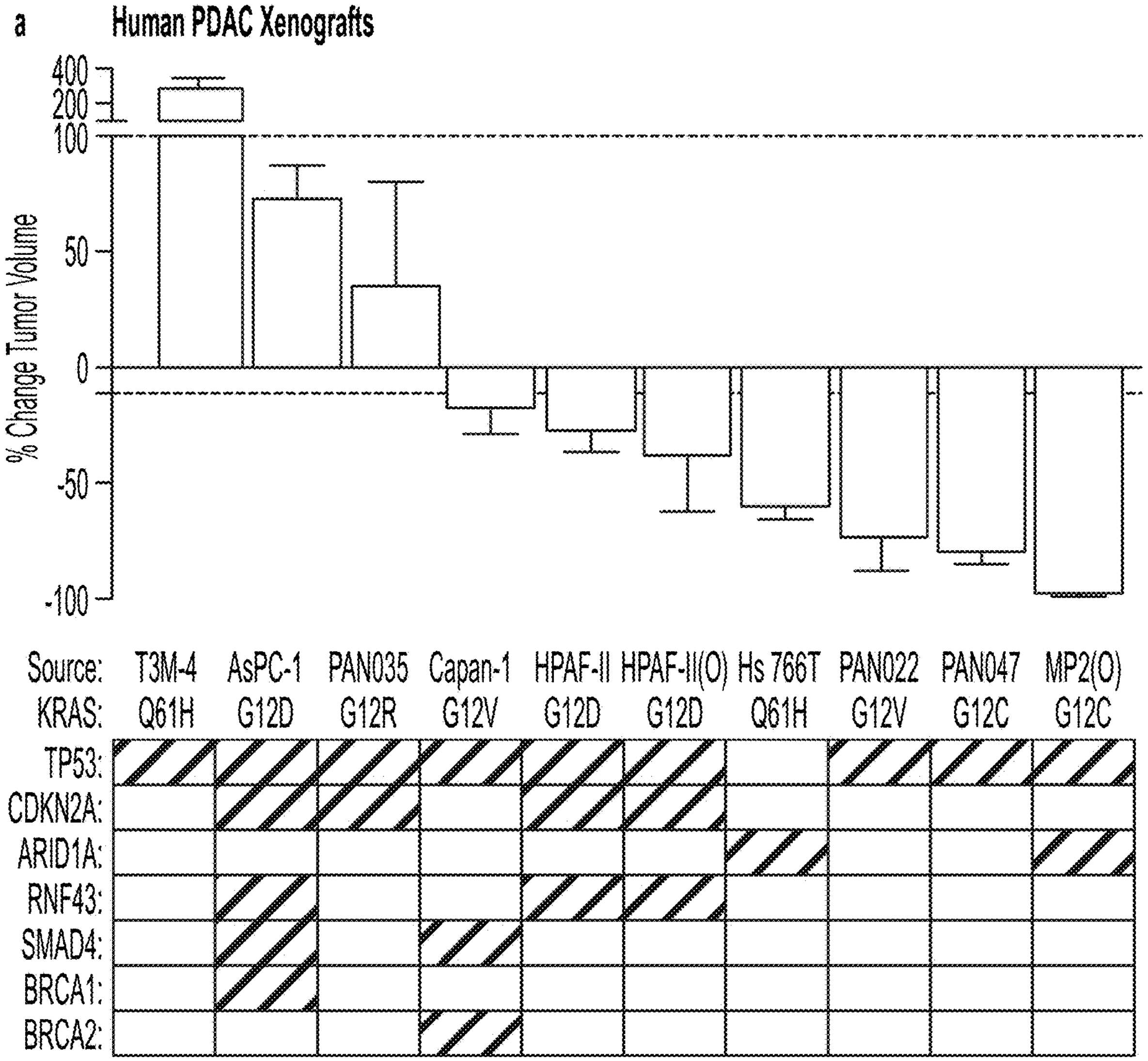
FIGS. 8A-8T: Human PDAC xenograft models from FIG. 2. (a) Waterfall plot showing tumor volume change from baseline in RMC-7977 treated tumors. Error bars indicate±s.e.m. Table shows selected genotypes for the xenograft panel with the row above indicating the KRAS mutation. Present co-mutations in each model shown as dark gray squares in the table. (b-i) Tumor growth curves for indicated xenograft models from (a), shown as percent tumor volume change from baseline over the course of treatment. Vehicle and RMC-7977 groups were compared by 2-way repeated measures ANOVA on the last measurement day of the vehicle group (*, p<0.05; , p<0.01; *, p<0.001; **, p<0.0001). Error bars indicate±s.e.m. (j-r) Tolerability of RMC-7977 as assessed by percent animal body weight change from baseline over the course of treatment, for indicated xenograft models from (a). Error bars indicate±s.e.m. (s, t) Kaplan-Meier survival analysis comparing RMC-7977 and Vehicle treatment arms in(s) subcutaneous and (t) orthotopic KPCYc4 allograft models (*, p<0.001; ****, p<0.0001)
Figure 8D:
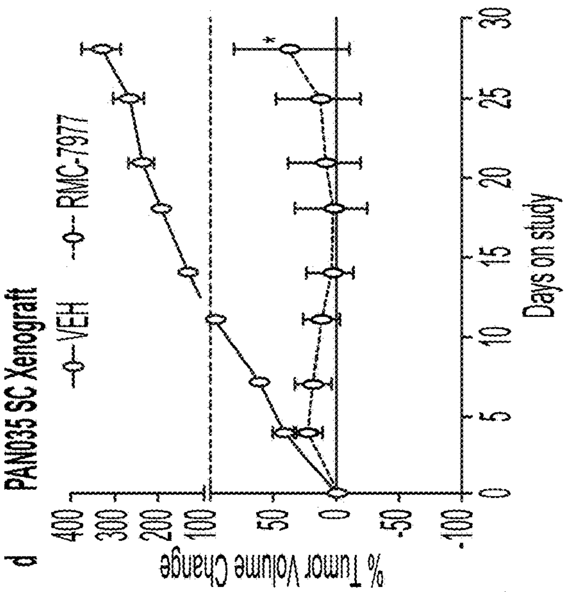
Figure 8C:
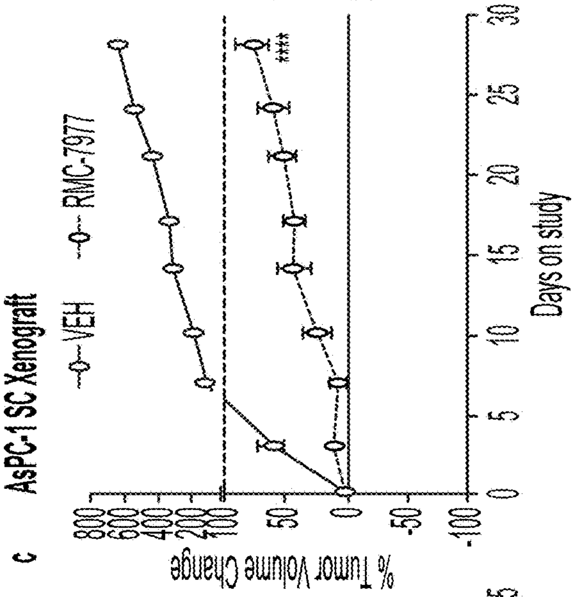
Figure 8B:
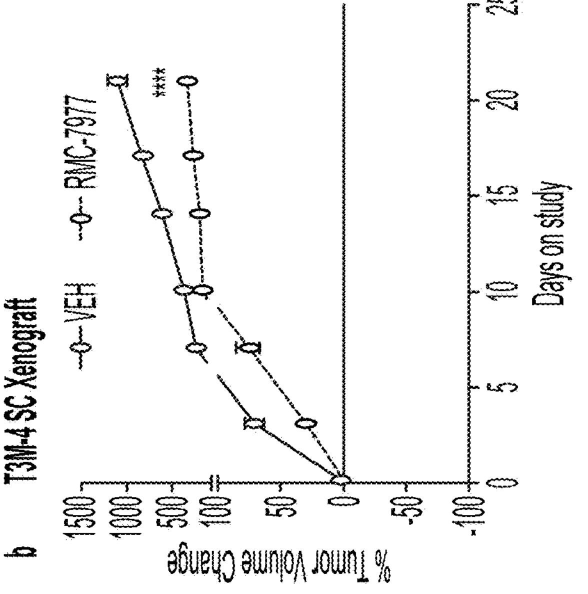
Figure 8G:
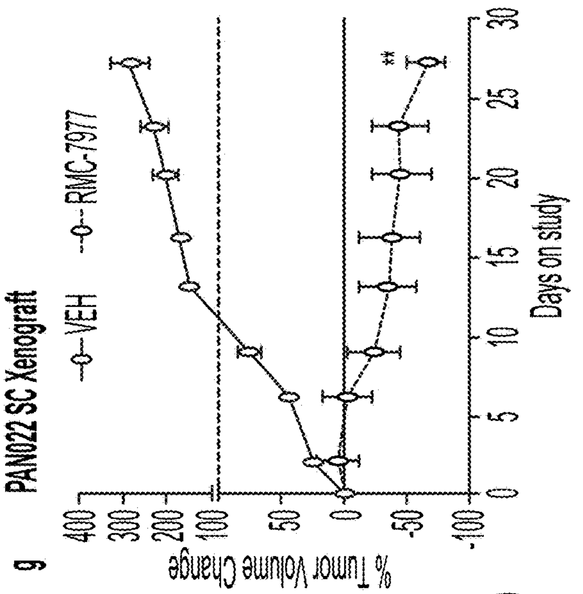
Figure 8F:
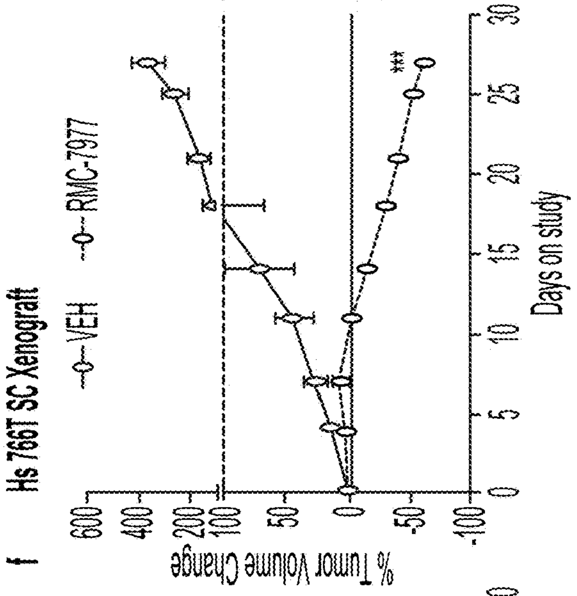
Figure 8E:
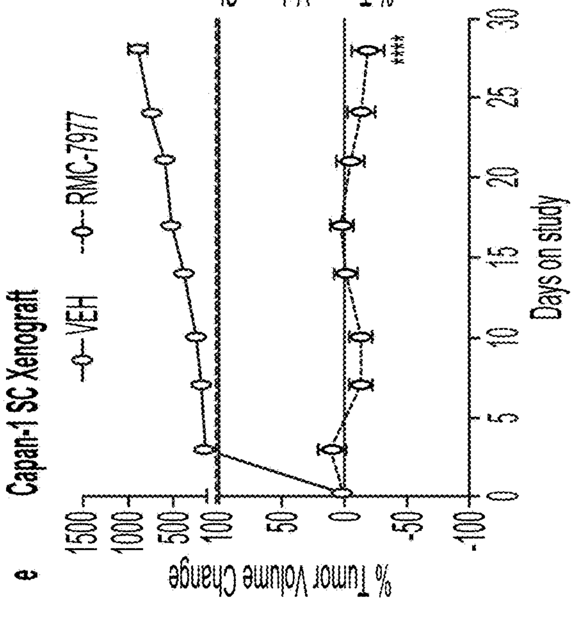
Figure 8J:
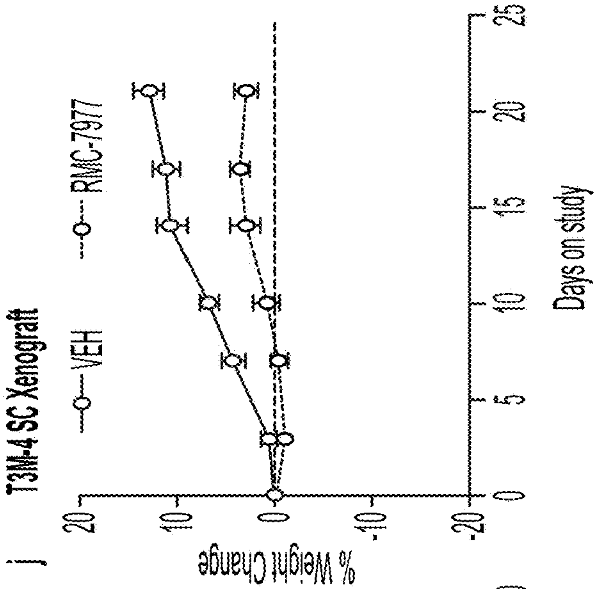
Figure 8I:
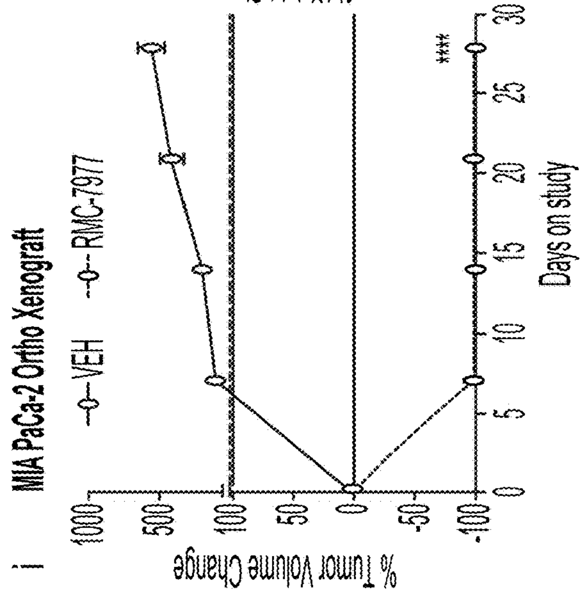
Figure 8H:
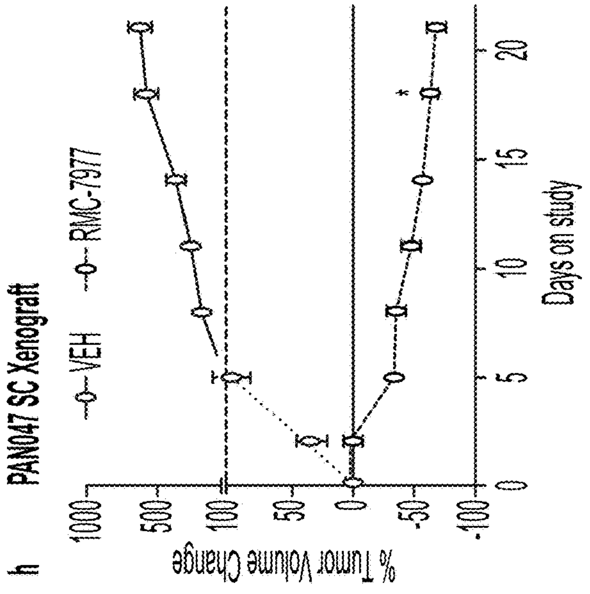
Figure 8K:
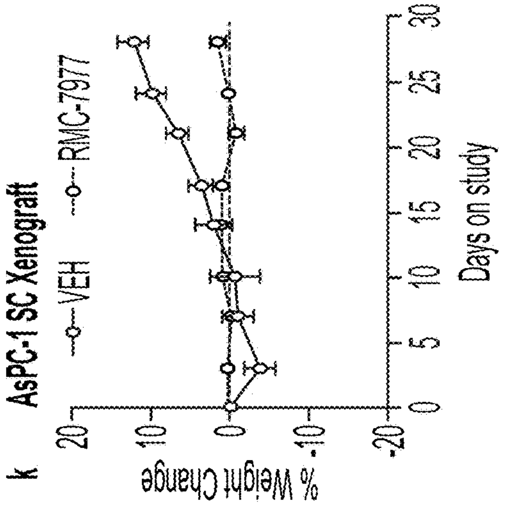
Figure 8L:
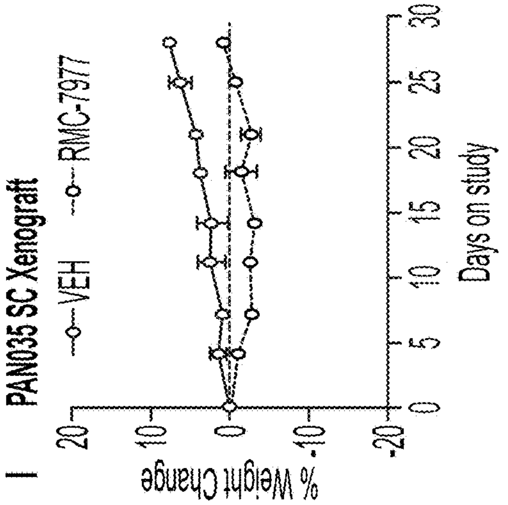
Figure 8M:
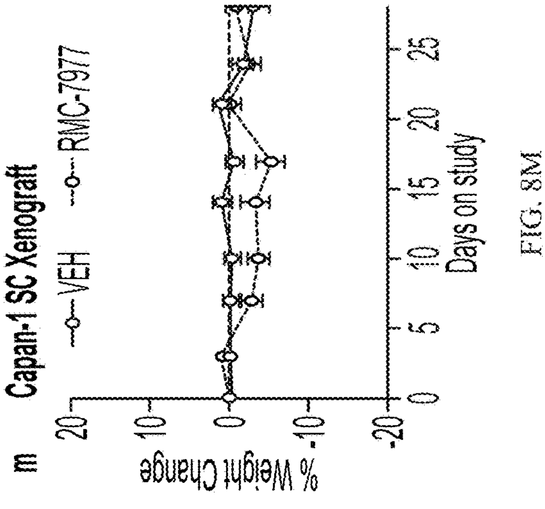
Figure 8N:
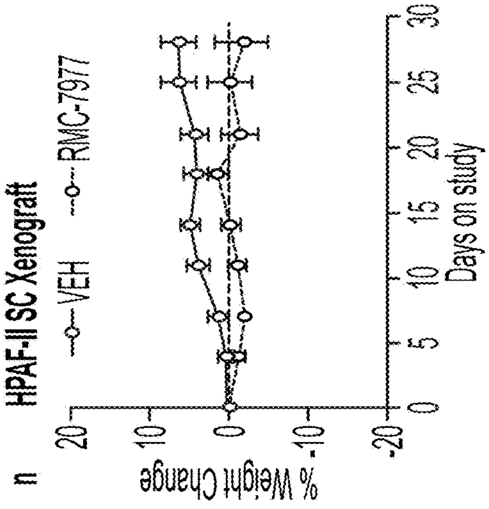
Figure 8O:
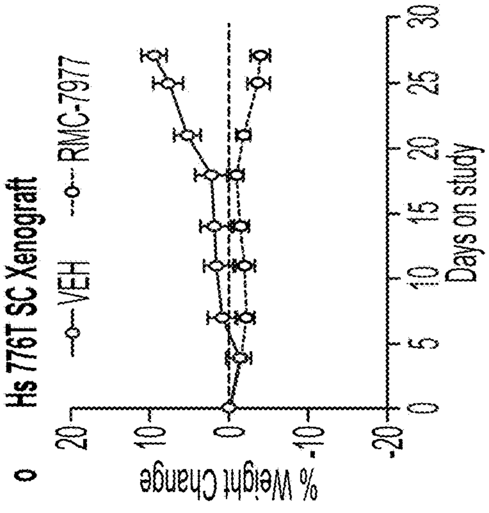
Figure 8P:
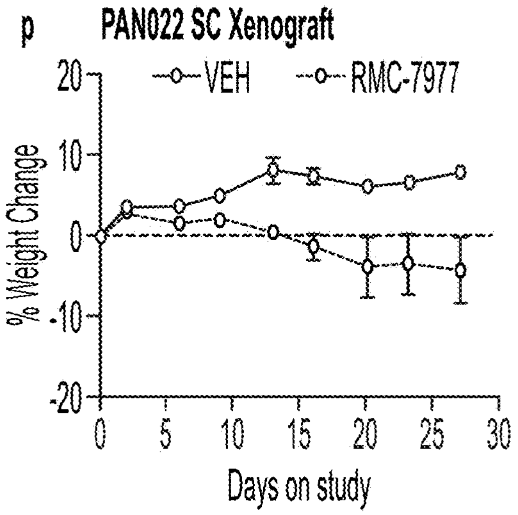
Figure 8Q:
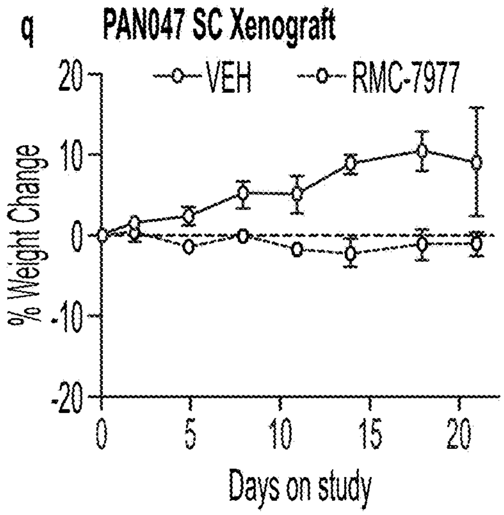
Figure 8R:
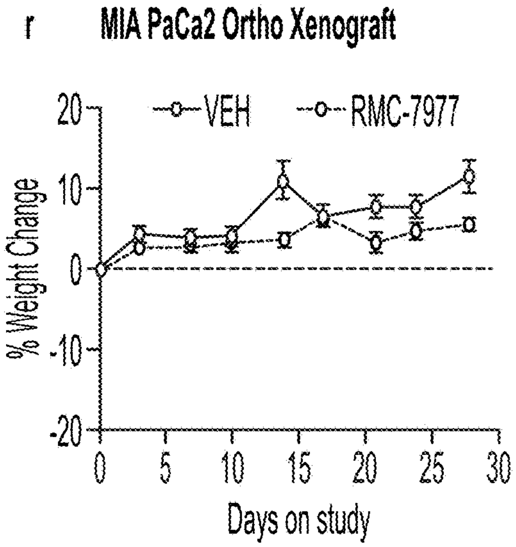
Figure 8S:
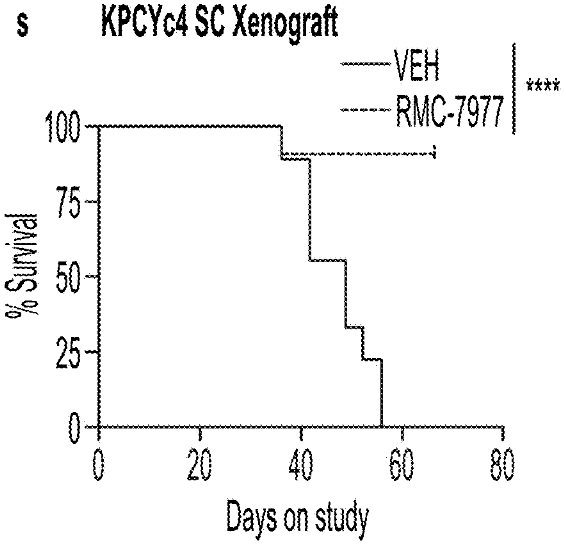
Figure 8T:
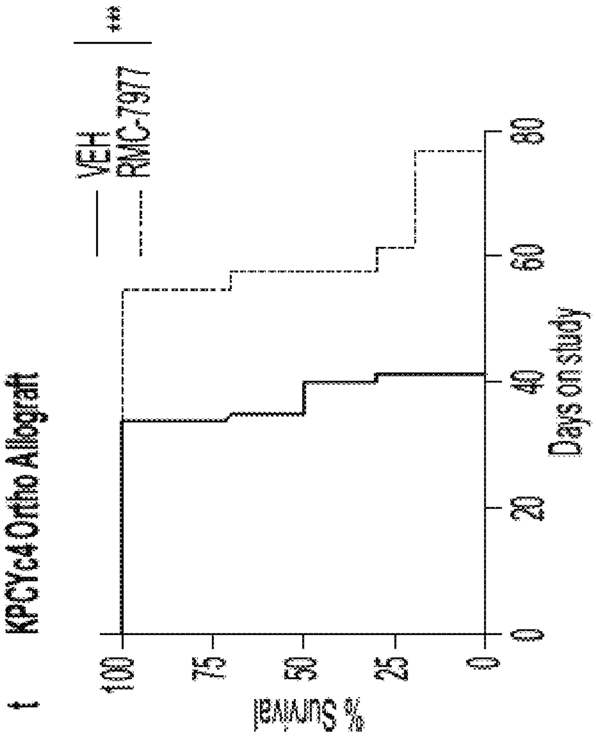

To test if the anti-tumor activity of RMC-7977 was affected by an intact immune system, we by used cell-line derived allografts (CDAs) in immunocompetent C57Bl/6 mice implanted either subcutaneously or orthotopically with a PDAC cell line from the KrasLSL.G12D/+; p53R172H/+; Pdx1-Cretg/+; Rosa26LSL.YFP/+(KPCY) mouse model, on a matched genetic background. In this setting, RMC-7977 still diminished tumor growth and extended overall survival, though without inducing significant regressions (FIGS. 2*f* and 8*s*,*t*). Pharmacodynamic analyses of the orthotopic CDA model showed reduced pERK levels and increased apoptosis in the tumors four hours after treatment, followed by recovery of pathway activity at 24 hours (FIG. 2*g*). Quantitative analysis of RMC-7977 levels in matched tumor tissue samples found that the restoration of RAS/MAPK activity in these tissues was consistent with the observed tumor half-life of 3.5 hours in this model. Taken together, these results demonstrate anti-tumor activity by RMC-7977 across a range of implanted PDAC models.

The Pharmacology of RAS Addiction

To understand the mechanistic basis of the broad anti-tumor effects described above, we carried out a detailed and quantitative analysis of the pharmacological profile of RMC-7977 in the setting of PDAC. We first examined the association of drug concentration and RAS pathway inhibition in a representative human CDX model of PDAC (Capan-1; KRASG12V). We assessed the response of tumor cells to treatment with a single dose of 10, 25, or 50 mg/kg RMC-7977 by measuring expression of human DUSP6, a RAS/MAPK pathway transcriptional target, in tumor tissues by qRT-PCR. DUSP6 levels were effectively inhibited for 24-48 hours post-dose and pathway inhibition was tightly associated with concentrations of RMC-7977 in tumors (FIG. 3*a*,*b*; EC50=142 nM in Capan-1 CDX tumors), indicating that the local drug concentration is a critical determinant of biochemical activity. We also observed somewhat prolonged RMC-7977 exposure in Capan-1 xenograft tumors, with a ~3-fold increase in overall exposure (AUC0-48) compared to that in blood.

Figures 3A, 3B, 3C, 3D, 3E, 3F:
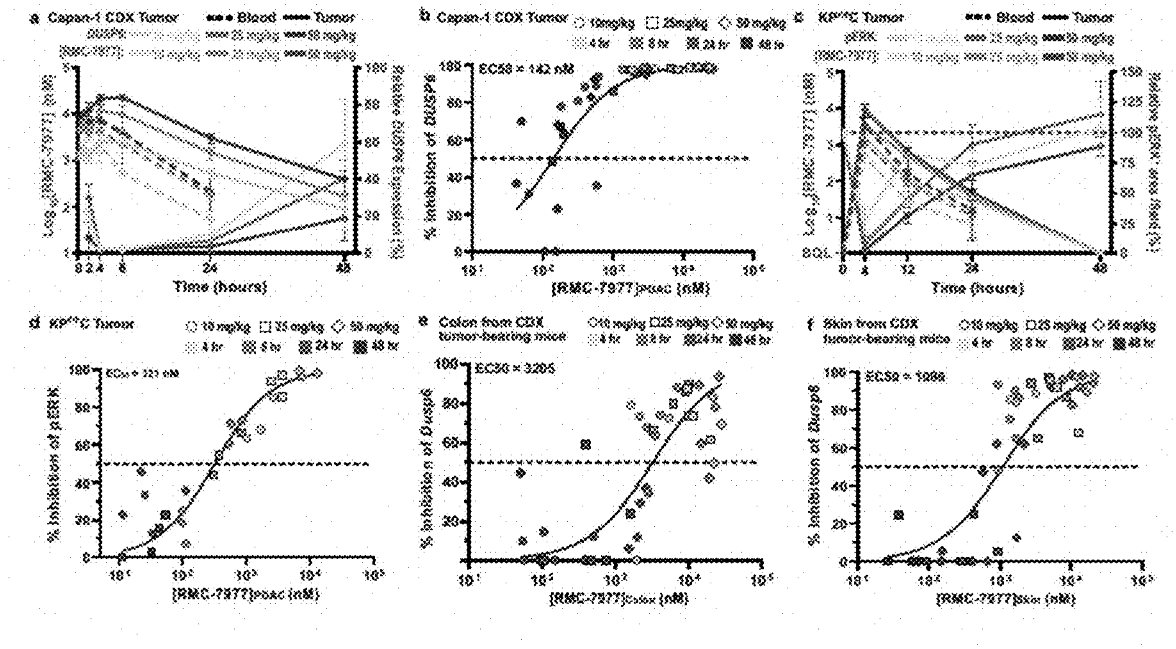
FIGS. 3A-3F: Pharmacology of RAS addiction. (a, b) Capan-1 subcutaneous xenograft tumors were treated with Vehicle or RMC-7977 at 10 mg/kg, 25 mg/kg and 50 mg/kg. Tissues were harvested at indicated timepoints (n=3-6/time-point/dose). (a) PK/PD in the Capan-1 xenograft model. Pharmacokinetic profile shown as RMC-7977 concentration in tumors (solid black lines) and blood (dashed black lines) over time. Pharmacodynamic response shown as relative change in DUSP6 mRNA expression (solid light gray lines). Shades of gray represent three tested doses. Values plotted as mean±s.d. (b) PKPD relationship between RMC-7977 concentration and inhibition of DUSP6 expression in tumors. (c, d) Tumor-bearing KPF/FC mice were treated with RMC-7977 at 10 mg/kg, 25 mg/kg and 50 mg/kg. Tissues were harvested at indicated timepoints (n=3/timepoint/dose). (c) PK/PD in the tumors isolated from KPF/FC mice. Pharmacokinetic response shown as RMC-7977 concentration in tumors (solid black lines) and blood (dashed black lines) over time. Pharmacodynamic response shown as relative change in pERK positive IHC staining in tumors (solid red light gray lines) over time. Shades of gray represent three tested doses. Values plotted as mean±s.d. (d) PKPD relationship between RMC-7977 concentration and pERK inhibition in tumors. (e, f) PKPD relationship between RMC-7977 concentration and inhibition of Dusp6 expression in normal (e) colons and (f) skin, isolated from CDX tumor-bearing mice. (b, d, e, f) A 3-parameter sigmoidal exposure response model was fitted to the data to derive EC50 values. Timepoints represented by shades of dark gray and doses represented by symbol shapes.
Figures 9A, 9B, 9C, 9D, 9E, 9F:
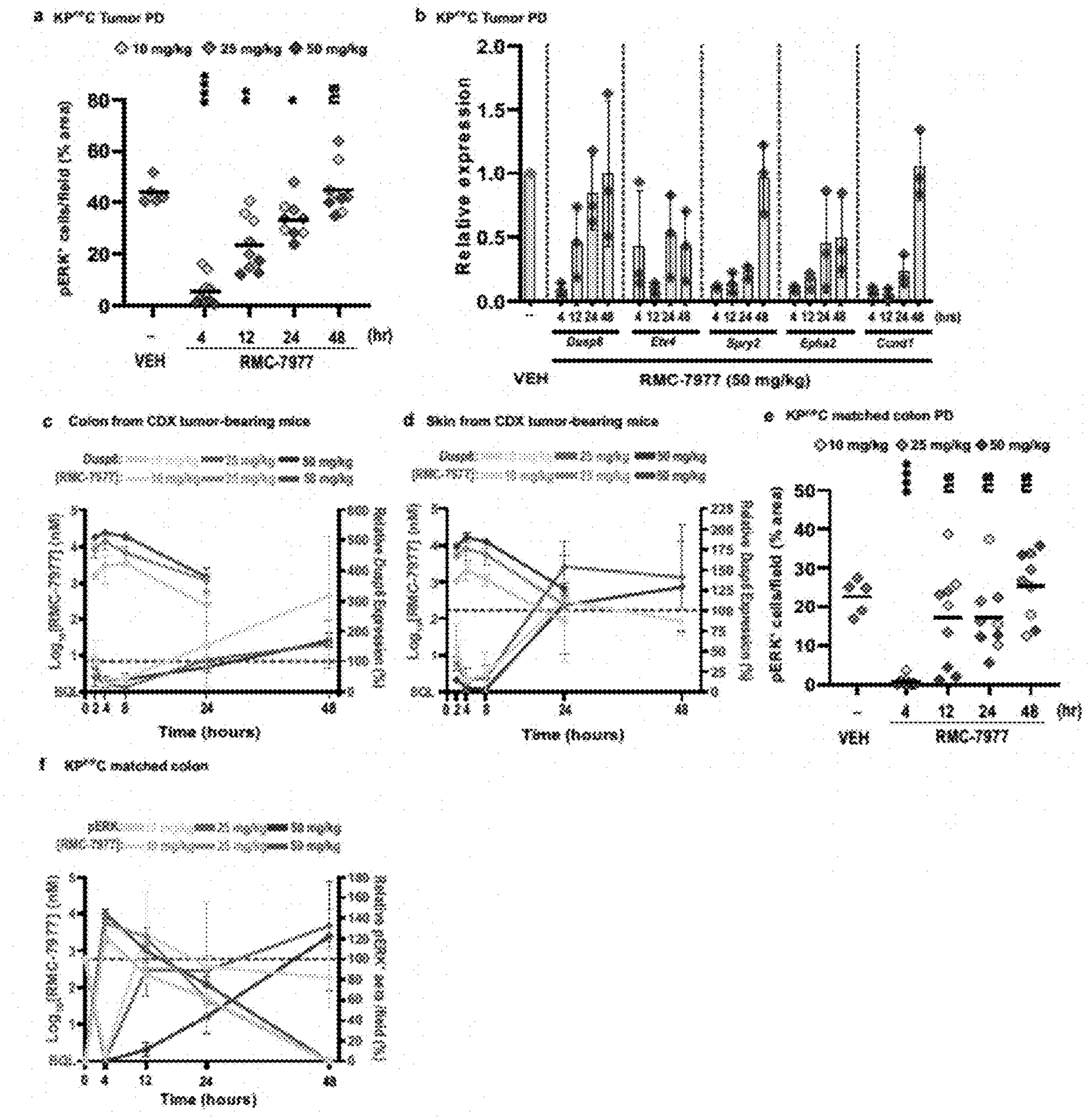
FIGS. 9A-9F: IHC analysis was ran on tissues collected from KPF/FC mice in FIG. 3. (a) Quantification of phospho-ERKT202/204 IHC staining of tumors isolated from Vehicle and RMC-7977 treated KPF/FC mice. (b) qRT-PCR analysis was ran on tumors collected from KPF/FC mice in FIG. 3 treated with Vehicle or RMC-7977 (50 mg/kg). Plot shows expression of five MAPK pathway signature genes at indicated timepoints. (c, d) PK/PD relationship in the colons and skin isolated from CDX tumor-bearing mice. Pharmacokinetic response shown as RMC-7977 concentration in (c) colon and (d) skin (solid gray lines) over time. Pharmacodynamic response shown as relative change in Dusp6 expression in colon or skin (red solid lines) over time. Shades of gray represent three tested doses. Error bars indicate s.d. (e) Quantification of phospho-ERKT202/204 IHC staining of colons isolated from Vehicle and RMC-7977-treated KPF/FC mice. (f) PK/PD relationship of RMC-7977 in the colons isolated from KPF/FC mice. Pharmacokinetic response shown as RMC-7977 concentration in colon (solid gray lines) over time. Pharmacodynamic response shown as relative change in pERK positive IHC staining in colon (red solid lines) over time. Shades of gray represent three tested doses. Error bars indicate s.d. (a, e) Analysis of IHC images based on 10-15 fields of view and plotted as average per tissue section. Shades of blue dark gray represent three tested doses. Results were compared by Student's unpaired t-test (*, p<0.05; , p<0.01; **, p<0.0001).

The delivery of drugs to autochthonous PDAC tumors can be impeded by their expansive desmoplastic stroma, which both suppresses tumor vascularity and impedes diffusion[27,28]. To assess whether the pharmacology of RMC-7977 permits effective targeting of RAS-GTP in the context of a native tumor microenvironment, we utilized KrasLSL.G12D/+; p53Flox/Flox; Pdx1-Cretg/+(KPF/FC) mice[29], a genetically engineered model that rapidly develops autochthonous KrasG12D mutant PDAC. We observed that pathway modulation in the KPF/FC model was somewhat less sensitive to RMC-7977, and exhibited earlier pathway recovery as compared to the Capan-1 CDX model, requiring higher doses (25 to 50 mg/kg) to achieve maximal and durable suppression of RAS/MAPK signaling as measured by decreases in DUSP6 mRNA or ERK phosphorylation (FIG. 3*a*,*c* and FIG. 9*a*). As anticipated, the expression of several MAPK pathway downstream target genes was also apparent in KPF/FC tumors (FIG. 9*b*). Examining the pharmacokinetic profile of RMC-7977 in KPF/FC mice, we found that exposure in the blood and PDAC tumors was lower than in CDX tumor-bearing BALB/c immune-deficient mice, comparable to that in the KPCY CDA model. This implies that strain- and model-specific variables could both contribute to the exposure and relative activity of RMC-7977 (FIG. 3*a*,*c*). We also observed a shorter half-life (t1/2) of RMC-7977 in KPF/FC tumors compared to CDX tumors and concordantly faster recovery of pERK levels (FIG. 3*c*,*d*). Importantly, the tight relationship between RMC-7977 concentration and pathway suppression observed in CDX models was maintained in this autochthonous model (FIG. 3*d*, EC50=321 nM). Moreover, in all model systems tested, concentrations of RMC-7977 were higher in tumor tissues than in blood (Kp >1), indicating the pharmacology of RMC-7977 can overcome they biophysical constraints to drug delivery imposed by the desmoplastic tumor microenvironment. Based on this and the reproducible tumor concentration/response (PK/PD) relationship across models, we predicted that daily or alternate day dosing schedules would yield an effective and metronomic pattern of RAS/MAPK pathway suppression in pancreatic tumors.

Pharmacologically, we have shown that RMC-7977 broadly inhibits RAS-MAPK activity in a wide range of preclinical models of PDAC at tolerable dose levels. This raises the question of how normal tissues pharmacodynamically respond to RMC-7977 treatment when compared to tumor tissue. To explore this question, we first examined the effects of RMC-7977 on murine Dusp6 mRNA levels (via qRT-PCR) in the normal colon and the skin, two proliferative tissue compartments known to rely on RAS signaling for self-renewal[30,31]. RMC-7977 demonstrated appreciably greater potency for RAS pathway modulation in tumor cells of the Capan-1 CDX model (EC50=142 nM, FIG. 3*b*) than in these normal tissues, exhibiting a ~22 fold and ~8 fold lower EC50 compared to colon and skin, respectively (FIG. 3*b*,*e*,*f* and FIG. 9*c*,*d*). We also examined pERK suppression via RMC-7977 in colon tissues from the KPF/FC cohort and found that RAS/MAPK activity was rapidly restored to baseline at the 10 and 25 mg/kg dose levels while pathway suppression was more prolonged in tumors at these doses (FIG. 3*c* and FIG. 9*e,f*). Together these data highlight a marked difference in the potency and kinetics of RMC-7977-mediated pathway modulation in normal tissues expressing RASWT compared to KRASG12X driven PDAC tumors[30].

Figures 4A, 4B, 4C, 4D, 4E, 4F:
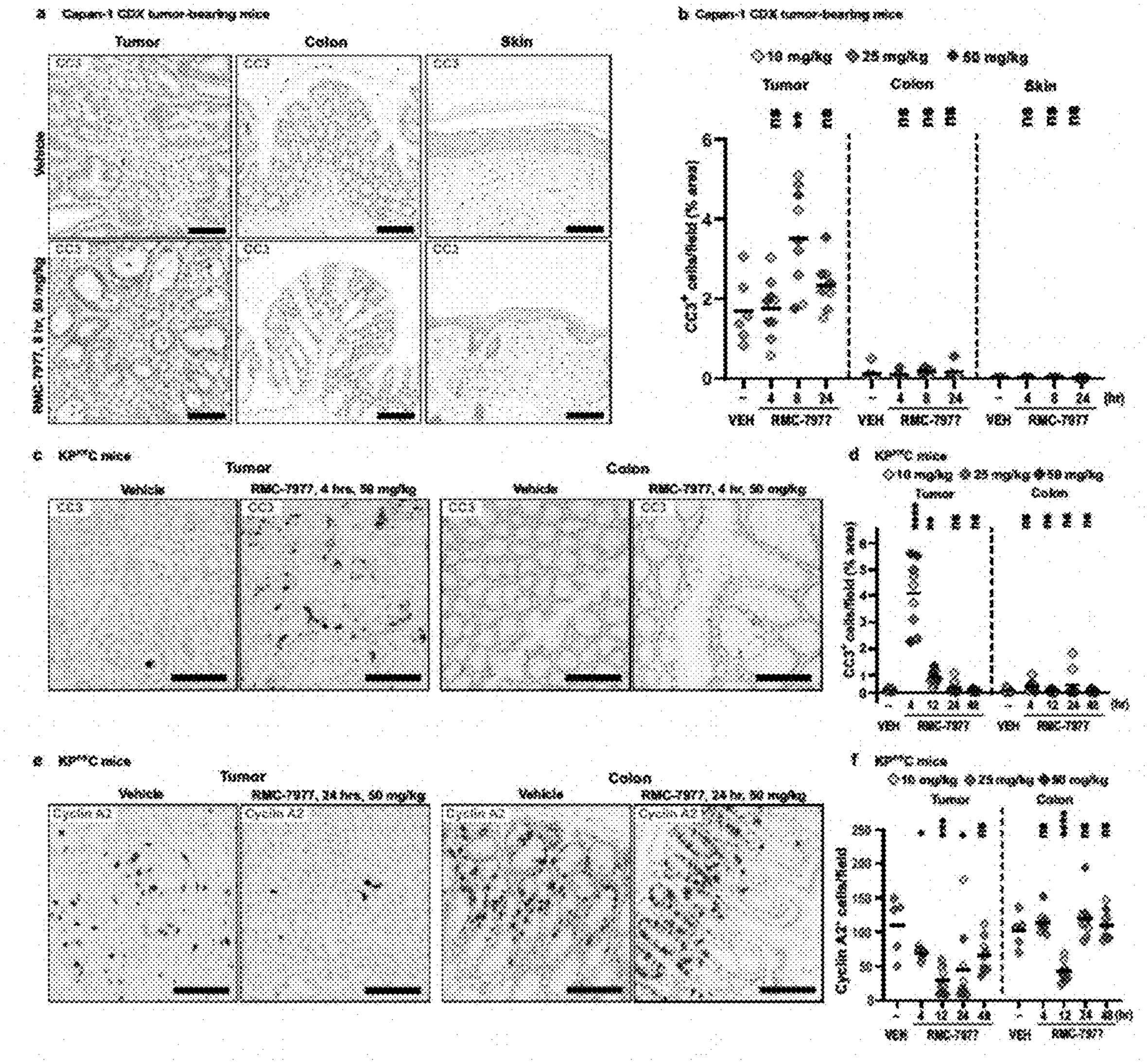
FIGS. 4A-4F: Inhibition of RAS induces pancreatic tumor-selective apoptosis. (a) Representative IHC images of tumors, colons, and skin from Capan-1 xenograft model collected at 8 hours post single dose of Vehicle or RMC-7977, stained for CC3. Scale bars=100 μm. (b) Quantification of CC3 staining in tumors, colon, and skin. (c) Representative IHC images of KPF/FC tumors and colons collected at 4 hours post single dose of Vehicle or RMC-7977, stained for CC3. Scale bars=50 μm. (d) Quantification of CC3 staining in tumors and colons. (e) Representative IHC images of KPF/FC tumors and colons collected at 24 hours post single dose of Vehicle or RMC-7977, stained for Cyclin A2. Scale bars=50 μm. (f) Quantification of Cyclin A2 staining in tumors and colons. (b, d, f) Analysis of IHC images based on 10-15 fields of view and plotted as average per tissue section. Shades of dark gray represent three tested doses. Results were compared by Student's unpaired t-test (*, p<0.05; , p<0.01; *, p<0.001; ****, p<0.0001

While RAS pathway inhibition by RMC-7977 was less potent and durable in normal tissues as compared to tumors, we wished to understand how RAS inhibition would impact the physiology of both malignant and non-malignant cells. To address this, we examined the effects of RAS inhibition on cellular proliferation and apoptosis in both tumor and normal tissues. In Capan-1 CDX tumors, we observed a notable increase in CC3+ apoptotic cells, peaking at 8 hours post-dose, relative to vehicle controls. By contrast, few apoptotic cells were observed in the colon or the skin from tumor-bearing animals at any timepoint (FIG. 4*a,b*). In KPF/FC tumors, we observed a sharp, ~4-fold spike in CC3+ apoptotic cells at four hours following a single dose of RMC-7977, that was not observed in the matched colon tissues from these mice (FIG. 4*c,d*). In both the KPF/FC and CDX models, the kinetics of apoptosis initiation in tumors closely mirrored the full inhibition of pERK. In stark contrast, apoptosis in normal tissues was negligible or absent across all doses and time points, even at the times when pERK was fully inhibited. From these KPF/FC mice, we observed only a transient decrease in proliferation at 12 hours, with Cyclin A2 levels fully restored by 24 hours (FIG. 4*e,f*). Thus, the overall proliferation of this self-renewing normal tissue was minimally impacted compared to the sustained anti-proliferative response observed in PDAC tissues. Together, these results demonstrate key differences in how RASWT normal tissues react and adapt to metronomic RAS inhibition with a broad-spectrum RAS inhibitor compared to tumors driven by mutant KRAS, providing a rational basis for the tumor-selectivity of RAS inhibition in PDAC.

Figure 5B:
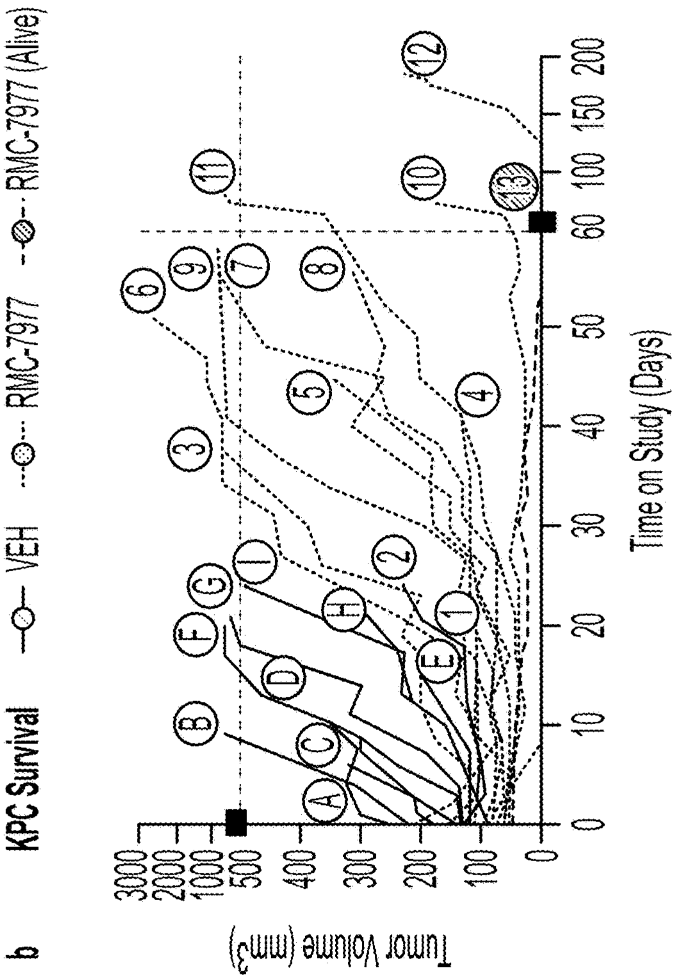
FIGS. 5A-5L: RMC-7977 inhibits tumor growth and extends survival in autochthonous models of PDAC. (a) KPC mice treated with Vehicle (n=9) or RMC-7977 (50 mg/kg, po, q.o.d., n=13) until endpoint criteria were met. (a) Kaplan-Meier survival analysis comparing RMC-7977 to Vehicle, and historical data from Gemcitabine and Vehicle treatment arms (****, p<0.0001). (b) Tumor growth rates calculated from longitudinal tumor volumes. (c) Waterfall plot showing best response for each tumor relative to initial volume. (b,c) Letters represent individual Vehicle treated animals and numbers represent RMC-7977 treated animals. (d) Schematic of KPCY mice (on C57Bl/6 background) treatment with Vehicle (n=6) or RMC-7977 (25 mg/kg, po, q.d.; n=8) for 15 days. (e) Tumor growth curves for mice in experiment as depicted in panel (d). Each line represents one mouse and each symbol represents ultrasound scan. (f) Waterfall plot showing percent change in tumor volume compared to baseline of KPCY after 15 days of treatment. (g) RMC-7977 tolerability as assessed by animal body weight change over the course of treatment. (h) Schematic of KPC mice (on 129S4/SvJae background) treatment with Vehicle (n=6) or RMC-7977 (50 mg/kg, po, q.o.d.; n=8) for 1 week. Tissues collected at 4 hours (n=4) or 24 hours (n=4) post last dose. (i) Tumor growth curves for mice in experiment as depicted in panel (h). Each line represents one mouse and each symbol represents ultrasound scan. (j) Waterfall plot showing percent change in tumor volume compared to baseline after 1 week of treatment. (k) RMC-7977 tolerability assessed by animal body weight change from baseline over the course of treatment. (1) IHC analysis of KPC tumors treated with Vehicle or RMC-7977 for indicated time, with tissues collected either at 4 or 24 hours post last dose. Tumors stained for phospho-ERKT202/204, pS6S235/236, pS6S240/244, CC3 and Cyclin A2. Quantification of IHC images was based on 10-15 fields of view (light shade), averaged per tumor (dark shade) and means were compared by Student's unpaired t-test (*, p<0.05; , p<0.001, *, p<0.001; ****, p<0.0001). Error bars indicate s.d.
Figure 5A:
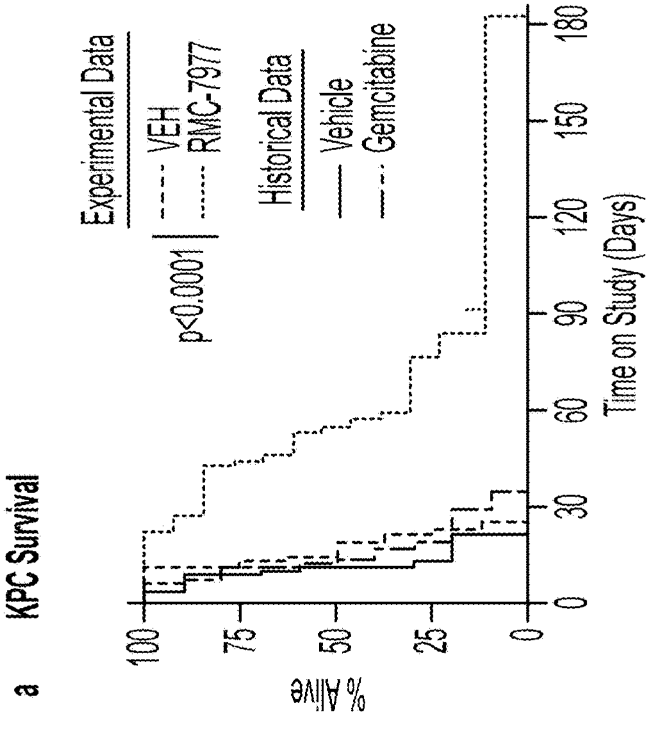
Figure 5C:
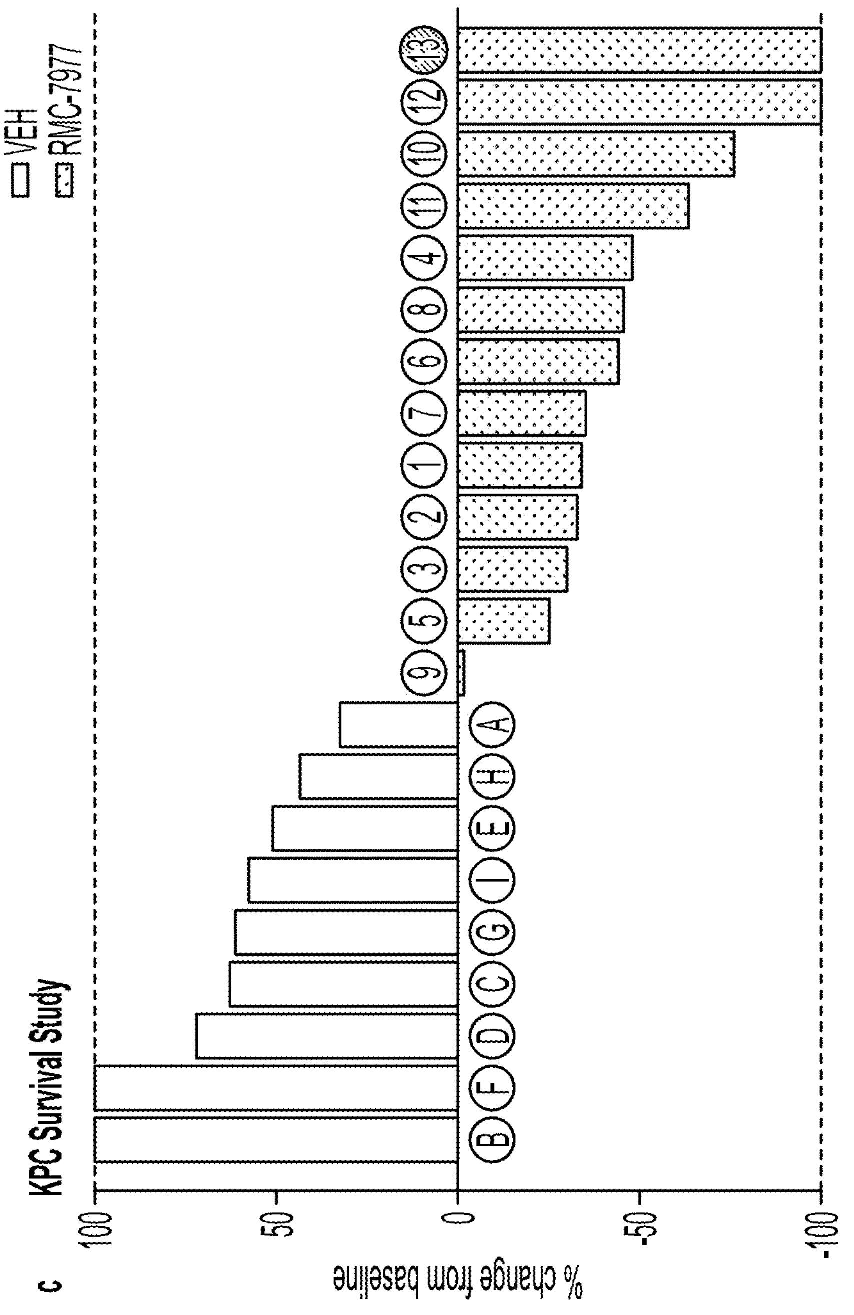
Figure 5D:
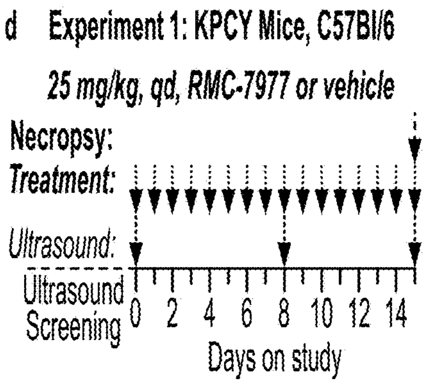
Figures 10A, 10B:
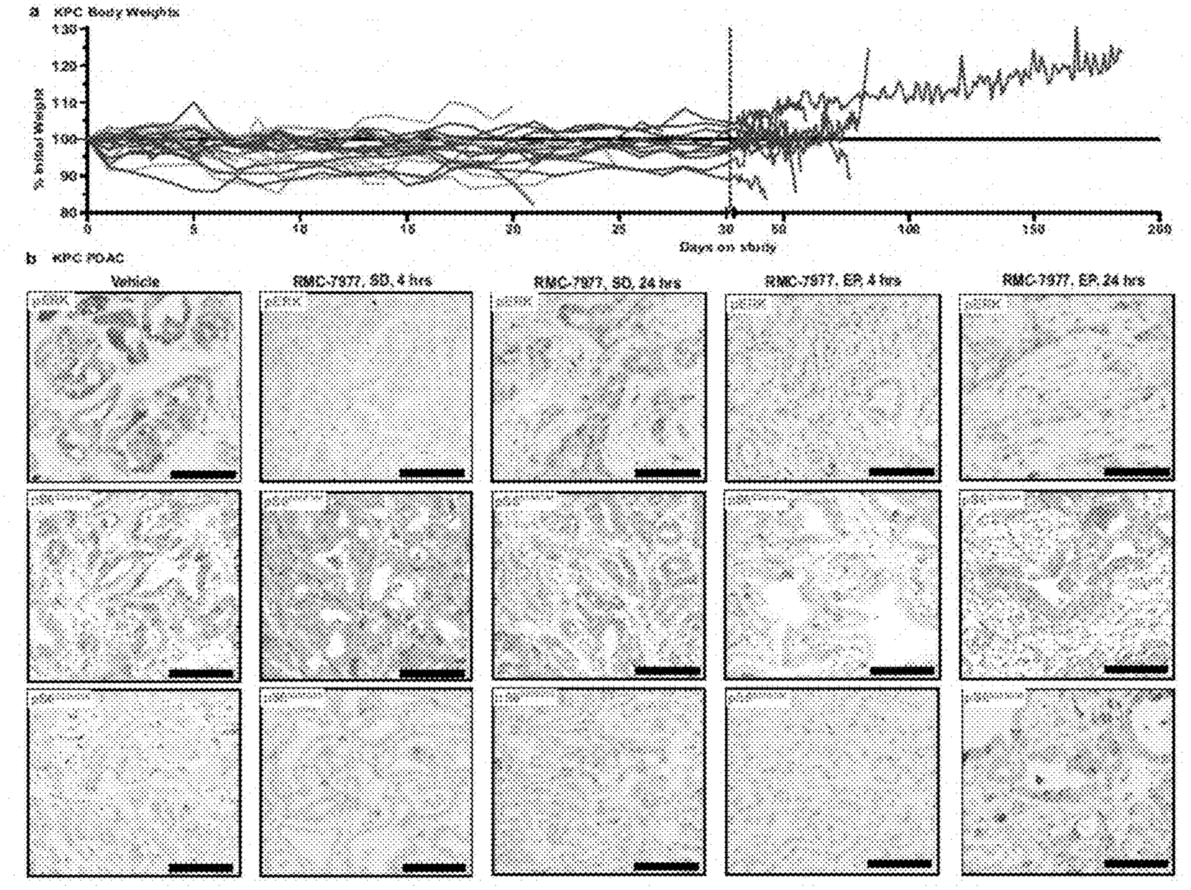
FIGS. 10A-10B: (a) KPC mice treated with Vehicle (n=9) or RMC-7977 (50 mg/kg, po, q.o.d., n=13) until endpoint criteria were met. Tolerability of RMC-7977 in KPC mice as assessed by percent animal body weight change from baseline over the course of treatment. (b) KPC mice treated with Vehicle or RMC-7977 for indicated time, with tissues collected either at 4 or 24 hours post last dose. Representative IHC images of KPC tumors collected at indicated timepoints post single dose of Vehicle or RMC-7977, or at treatment endpoint. Tumors were stained as labeled. Scale bars=100 m.

Preclinical Efficacy and Tolerability of RMC-7977 in Autochthonous Models of PDAC To evaluate the anti-tumor activity of RMC-7977 in clinically predictive models of human PDAC, we first performed an interventional survival study in tumor-bearing KrasLSL.G12D/+; p53LSL.R172H/+; Pdx1-Cretg/+(KPC) mice. Kaplan-Meier analysis of overall survival showed a 3.5-fold increase in median survival in the RMC-7977 treated cohort as compared to controls (FIG. 5*a*), exceeding the most effective therapy reported in the KPC model[32]. By comparison, cytotoxic chemotherapies, such as gemcitabine, and monotherapies in general do not significantly alter survival in this model[27]. Longitudinal, high-resolution 3D-ultrasound imaging[33] revealed that animals treated with 50 mg/kg RMC-7977, q.o.d. exhibited tumor stabilizations or regressions. By contrast, tumors in vehicle-treated mice uniformly exhibited progressive growth (FIG. 5*b,c*). The body weights of KPC mice treated with RMC-7977 were similar to those of control KPC mice (FIG. 10*a*).

Figure 5E:
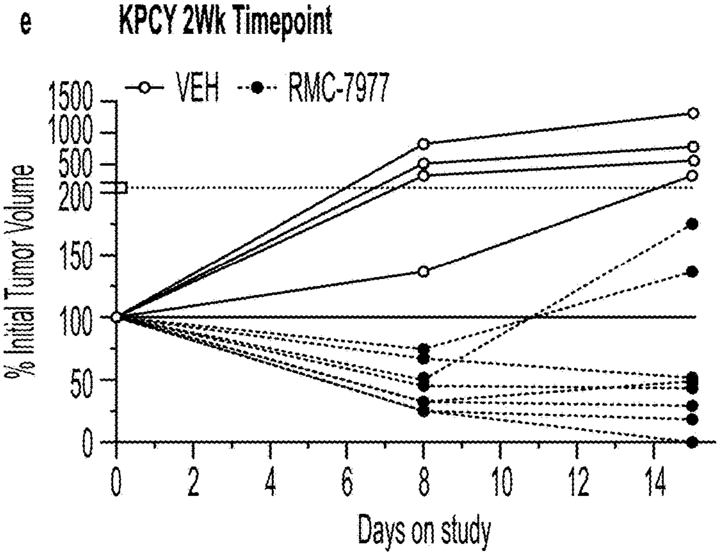
Figure 5F:
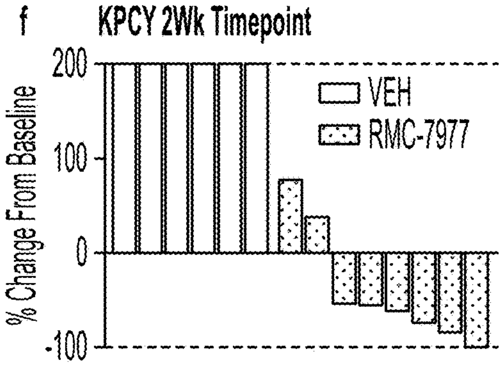
Figure 5G:
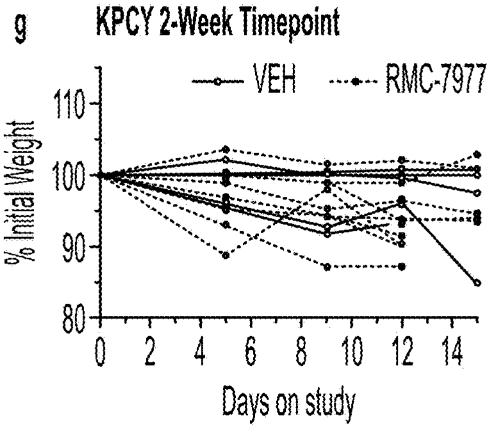
Figure 5H:
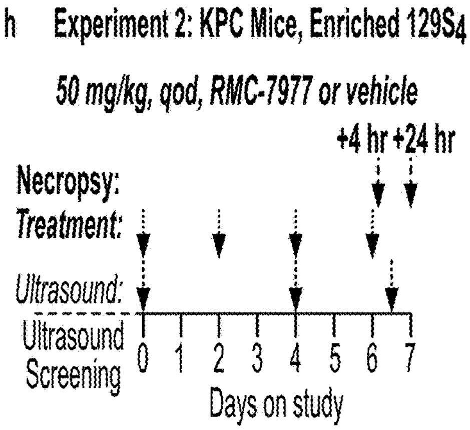
Figure 5I:
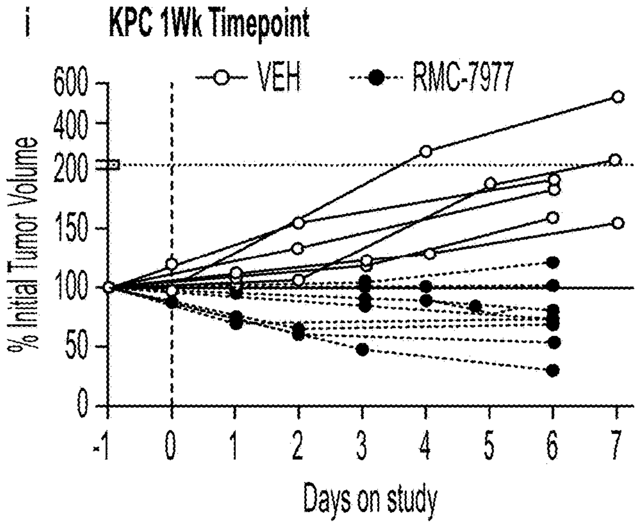
Figure 5J:
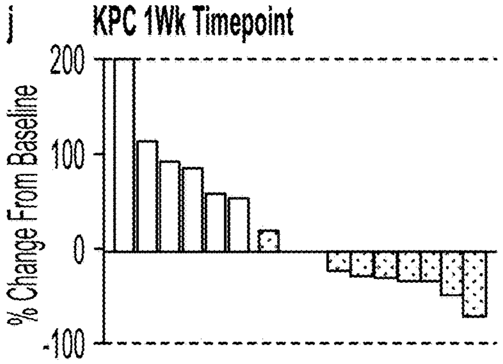
Figure 5K:
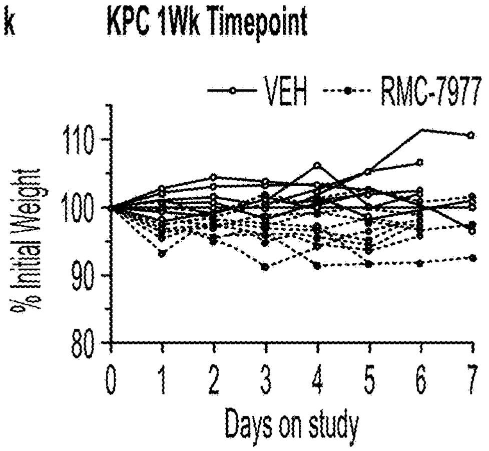

Next we carried out short-term intervention studies at multiple timepoints in two variants of the KPC model. Performed independently at separate institutions, the first study treated a YFP-lineage traced version of the KPC model (KPCY), on a pure C57Bl/6 background, with daily 25 mg/kg RMC-7977, for two weeks (FIG. 5*d-g*). The second study treated KPC mice, on a background enriched for 129S4/SvJae, with 50 mg/kg RMC-7977 q.o.d., for one week (FIG. 5*h-k*). In both experiments, RMC-7977 treatment induced regressions in most tumors, with little impact on animal weight (FIG. 5*e-g,i*-k).

To characterize the pharmacodynamic responses of KPC tumors and normal tissues to RMC-7977 mediated active-RAS inhibition, we performed IHC and qRT-PCR analyses on samples from additional KPC animals treated with a single dose (SD) of RMC-7977 or vehicle, from treated animals in the 1-week (1 wk) KPC study, and on endpoint (EP) tumor samples collected from animals that relapsed on treatment (resistant) in the KPC survival study. Within each group of animals, mice were euthanized either 4- or 24-hours after dosing, in order to capture the dynamic changes associated with metronomic pathway inhibition.

Figure 5L:
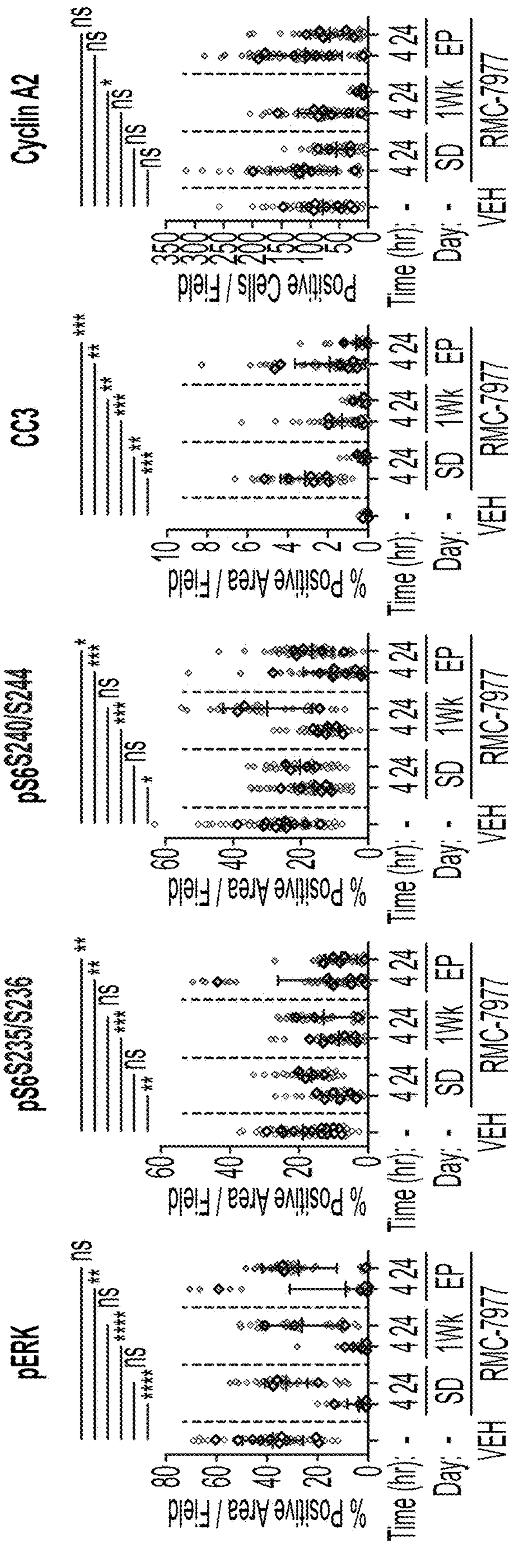
Figure 11A:
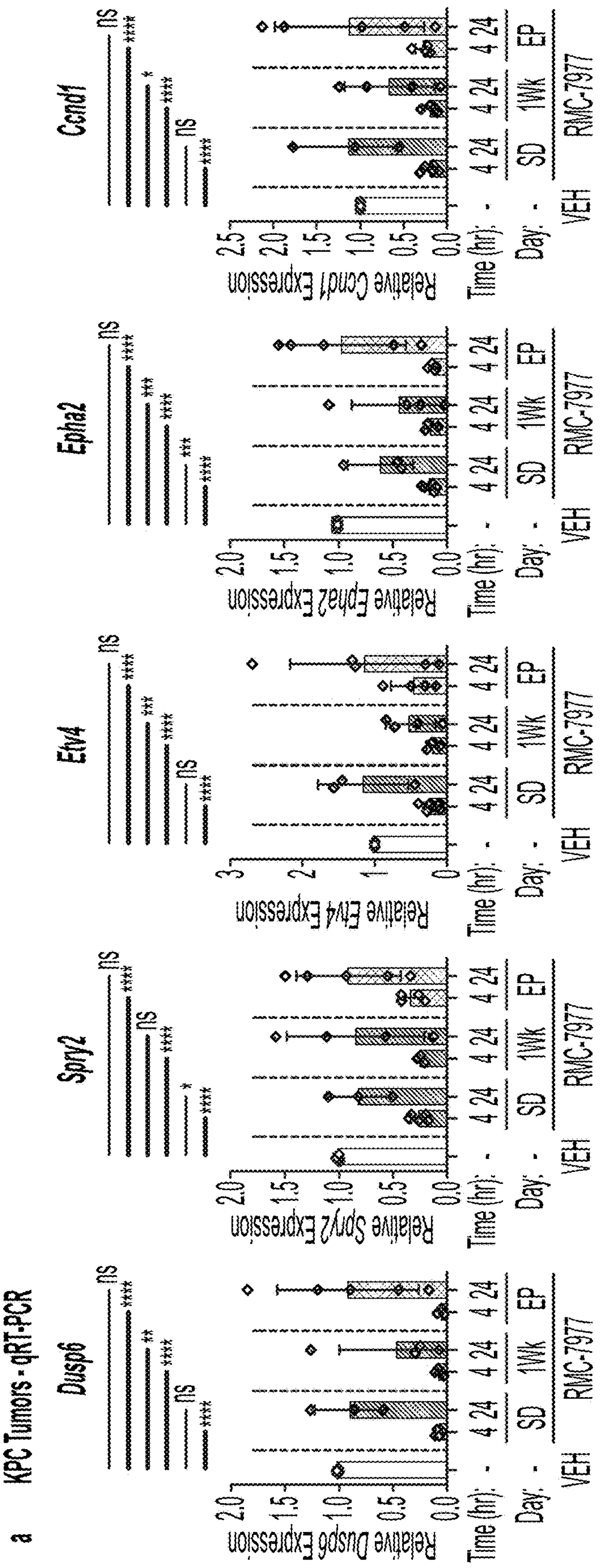
FIGS. 11A-11E: IHC analysis of KPC tumors (from FIG. 5) treated with Vehicle or RMC-7977 for indicated time, with tissues collected either at 4 or 24 hours post last dose. (a) qRT-PCR analysis showing expression of five MAPK pathway signature genes in KPC tumors at indicated timepoints post last dose. (b) Representative IHC images of KPC colon and skin collected at endpoint and stained for CC3. Scale bars=100 μm. (c) Quantification of CC3 staining in colon, and skin. (d) Representative IHC images of KPC colon and skin collected at endpoint and stained for Cyclin A2. Scale bars=100 μm. (e) Quantification of Cyclin A2 staining in colon and skin. Quantification of IHC images was based on 10-15 fields of view (light shade), averaged per tissue section (dark shade) and means were compared by Student's unpaired t-test (*, p<0.05). Error bars indicate s.d.
Figure 11B:
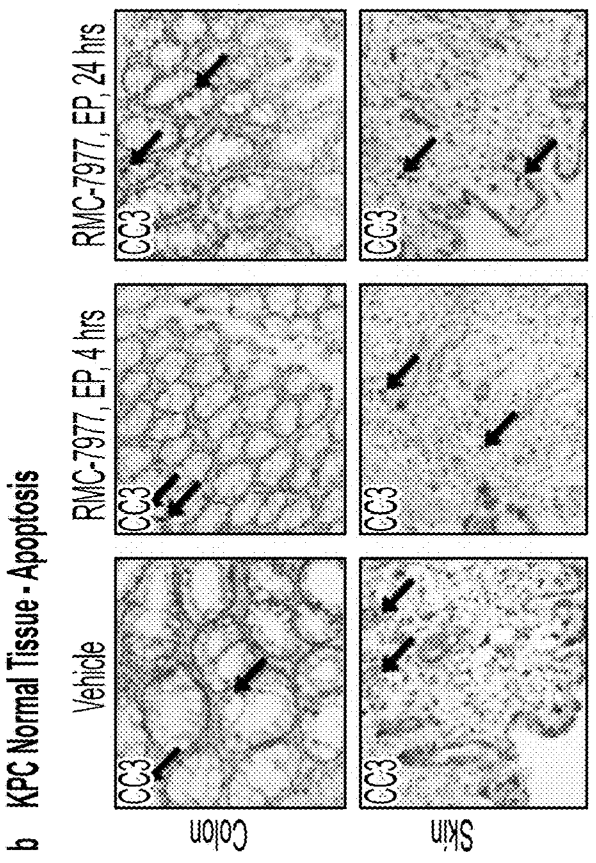
Figure 11C:
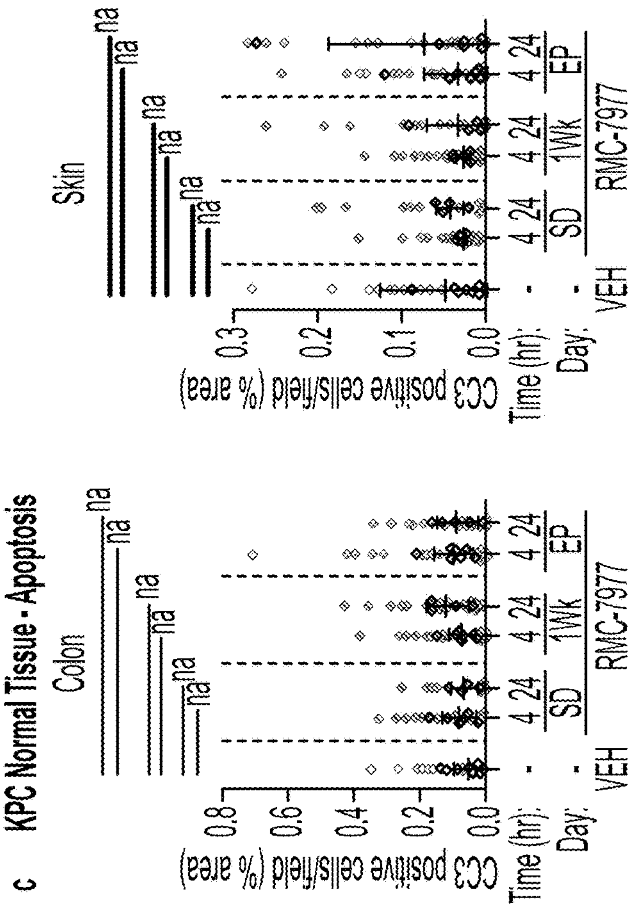
Figure 11D:
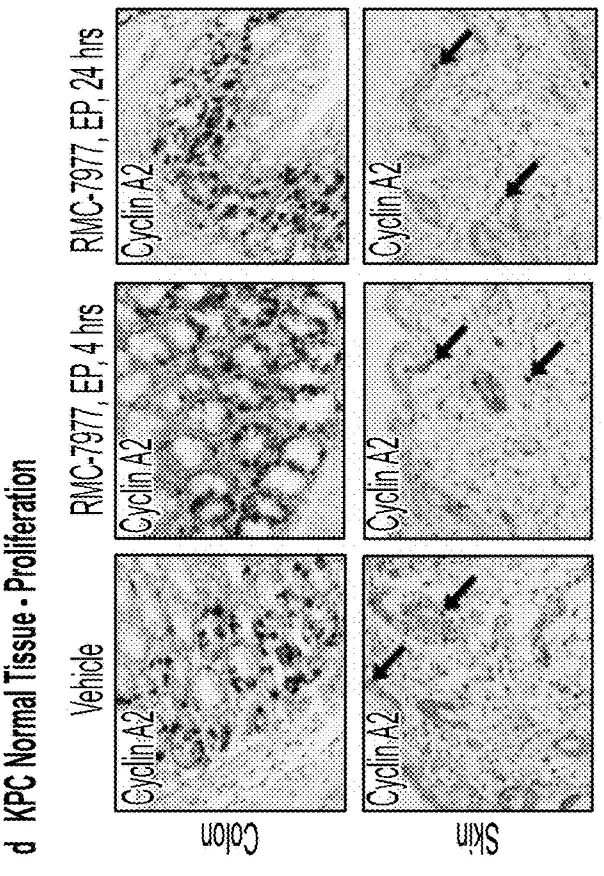
Figure 11E:
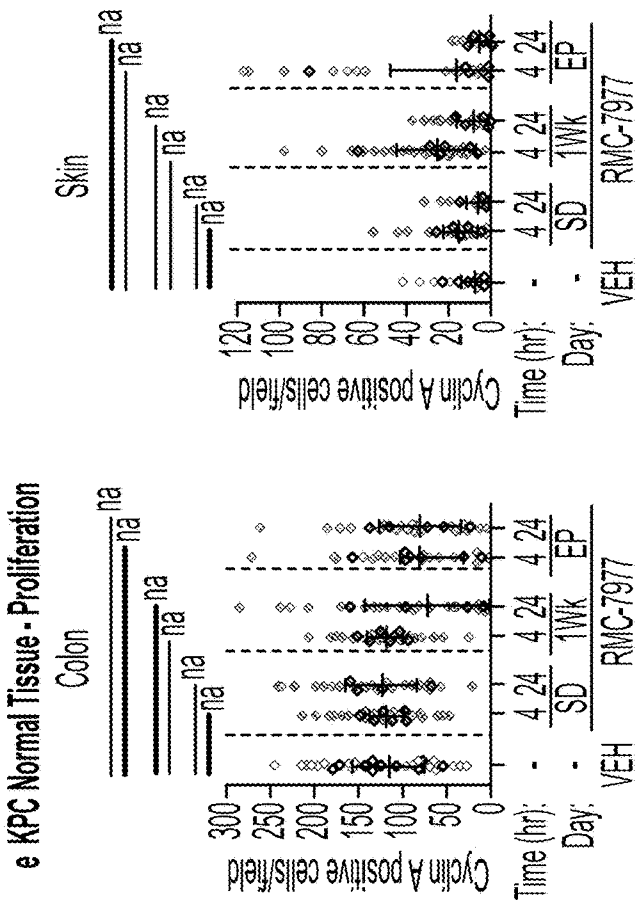

Quantification of pERK IHC staining on SD tumor samples showed that the effects of a single dose of RMC-7977 in KPC tumors were consistent with our earlier observations in the KPF/FC model, reflecting near-complete inhibition of Ras/Mapk signaling 4 hours after treatment followed by restoration by 24 hours (FIG. 5*l*). A similar pattern was also observed for phospho-S6RP, at both the S235/S236 and S240/S244 sites (FIG. 10*b*). Importantly, the metronomic pattern of pathway inhibition was also apparent in the 1 Wk and EP samples, demonstrating a persistent and cyclical pharmacodynamic response to RMC-7977 treatment over time. These data were supported by parallel analyses of the same tumors using qRT-PCR, showing that five MAPK pathway target genes were similarly regulated at the transcriptional level (FIG. 11*a*).

Next we examined the cellular responses of KPC tumors at each timepoint. The wave of apoptosis that was observed in KPF/FC mice 4 hours after a single dose of RMC-7977 (FIG. 4*d*) was also observed in KPC mice in SD, 1 Wk, and EP samples collected 4 hours after treatment (FIG. 5*l*), suggesting that each successive dose of RMC-7977 induces an additional wave of apoptosis. KPC tumors also showed a trend towards reduced proliferation following a single dose of RMC-7977, which was pronounced and significant after a week of treatment. However, in contrast to the persistent induction of apoptosis, proliferation was no longer deeply suppressed at 24 hours post-dosing in response to RAS inhibition in EP tumors (FIG. 5*l*, CyclinA2; see Mechanisms of Resistance, below).

Finally, to assess the impacts of long-term treatment on normal tissues, we performed IHC on colon and skin samples from the SD, 1 Wk, and EP KPC mice. Effects of RMC-7977 on apoptosis (CC3) and proliferation (Cyclin A2) were absent or negligible at all timepoints in both tissues (FIG. 11*b-e*). More broadly, in a blinded histopathological review of H&E-stained liver, intestines, lungs, kidneys, and skin in all KPC mice from the study, the only treatment-associated histopathological feature detected was a modest increase in apoptosis in the proximal intestines of half the treated animals, albeit this was not associated with diarrhea or weight loss. Taken together, our preclinical findings have significant and positive implications for the translation of multi-specific RAS-GTP inhibition in patients with pancreatic ductal adenocarcinoma and potentially other types of RAS-addicted cancers.

Mechanisms of Resistance to RAS-GTP Inhibition

Emerging preclinical and clinical data demonstrate a diverse range of potential mechanisms through which tumors may acquire resistance to mutation-selective RAS inhibitors. In the majority of cases, tumors overcome mutation-selective RAS inhibition through reactivation of RAS/MAPK signaling, either through the emergence or outgrowth of clones harboring second-site RAS mutations, through amplification of pathway members, or through compensatory signaling mechanisms[8,9,34,35]. To assess the potential mechanisms of resistance to a multi-specific RAS-GTP inhibitor, we analyzed the EP KPC pancreatic tumors that relapsed following initial responses in the survival study, developing resistance while on continuous RMC-7977 treatment. Of 7 evaluable EP KPC tumors (e.g. those that were collected 4 hours post final dose, when RAS signaling is suppressed in naive tumors), 6 tumors (86%) continued to show full inhibition of pERK expression (FIG. 5*l*), thereby excluding several classes of mechanisms that reactivate RAS/MAPK signaling. The same 6 tumors also exhibited continued inhibition of pS6S235/5236 and pS6S240/5244, excluding mechanisms that primarily impact the PI3K/mTOR arm of RAS signaling (FIG. 5*l*). Of interest, the one EP tumor refractory to pERK modulation due to apparently reactivated Ras pathway signaling (Tumor 12 in FIG. 5*b*) survived over half a year on treatment, longer than any other animal in the study.

Figure 6A:
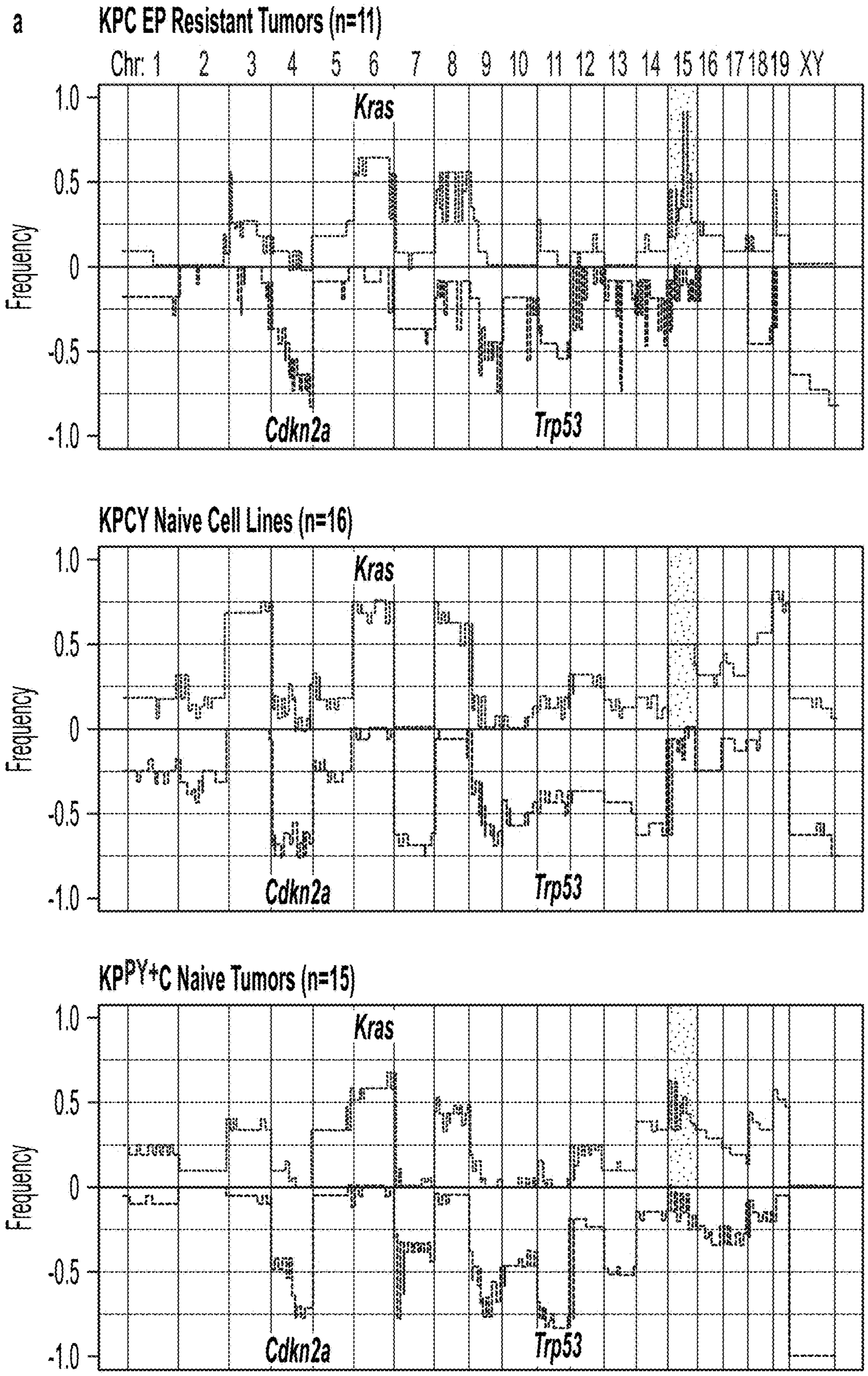
FIGS. 6A-6F: Resistance to RMC-7977 predominantly arises independent of MAPK activity. (a) CNV analysis of: DNA isolated from epithelial cells of RMC-7977 resistant KPC tumors; KPF/+C naive tumors and KPCY tumor-derived cell lines. Highlighted region marks chromosome 15, which includes the Myc locus for mice. (b) CNV plots showing region of Chromosome 15 in RMC-7977 resistant KPC tumors. Vertical light gray lines mark Myc locus. Horizontal hashed line indicates threshold to be called as a gain. Letters indicate tumor identity from FIG. 5. (c-g) Cell lines derived from RMC-7977 resistant or naive KPC tumors. (c) Cell lines treated with DMSO or indicated concentrations of RMC-7977 for 3-5 days. (d) Mass-spectrometry based proteomic analysis comparing the effects of RMC-7977 and DMSO treatment in resistant K18509R (MYCGain) and naive K8484 (MYCStable). Differential protein expression signatures within each line analyzed for enrichment of published functional gene sets (E2F, MYC, YAP/TAZ). Data points in (c) represent the mean of technical 3 replicates normalized to DMSO control. Error bars indicate s.d. RMC-7977 resistance and MYC status are indicated by curve colors. (e) Representative Western Blot images for two RMC-7977 resistant (K18745R and K18508R) and two naive (K8484 and K2293) cell lines treated with DMSO, RMC-7977 (100 nM), IAG933 (1 μM) or combination for 24 hours. Protein levels of phospho-ERKT202/204, total ERK, MYC, CYR61, Survivin, CDC20 and ECT2 were analyzed. Vinculin and β-tubulin were used as loading controls. (f) Cell lines as indicated in (e) treated with indicated concentrations of RMC-7977, IAG933 or DMSO, combinations. The dose-response matrices show combination synergy based on cell viability at different dose pairs. Shades of darker and lighter gray represent synergistic and antagonistic effects respectively.
Figure 6B:
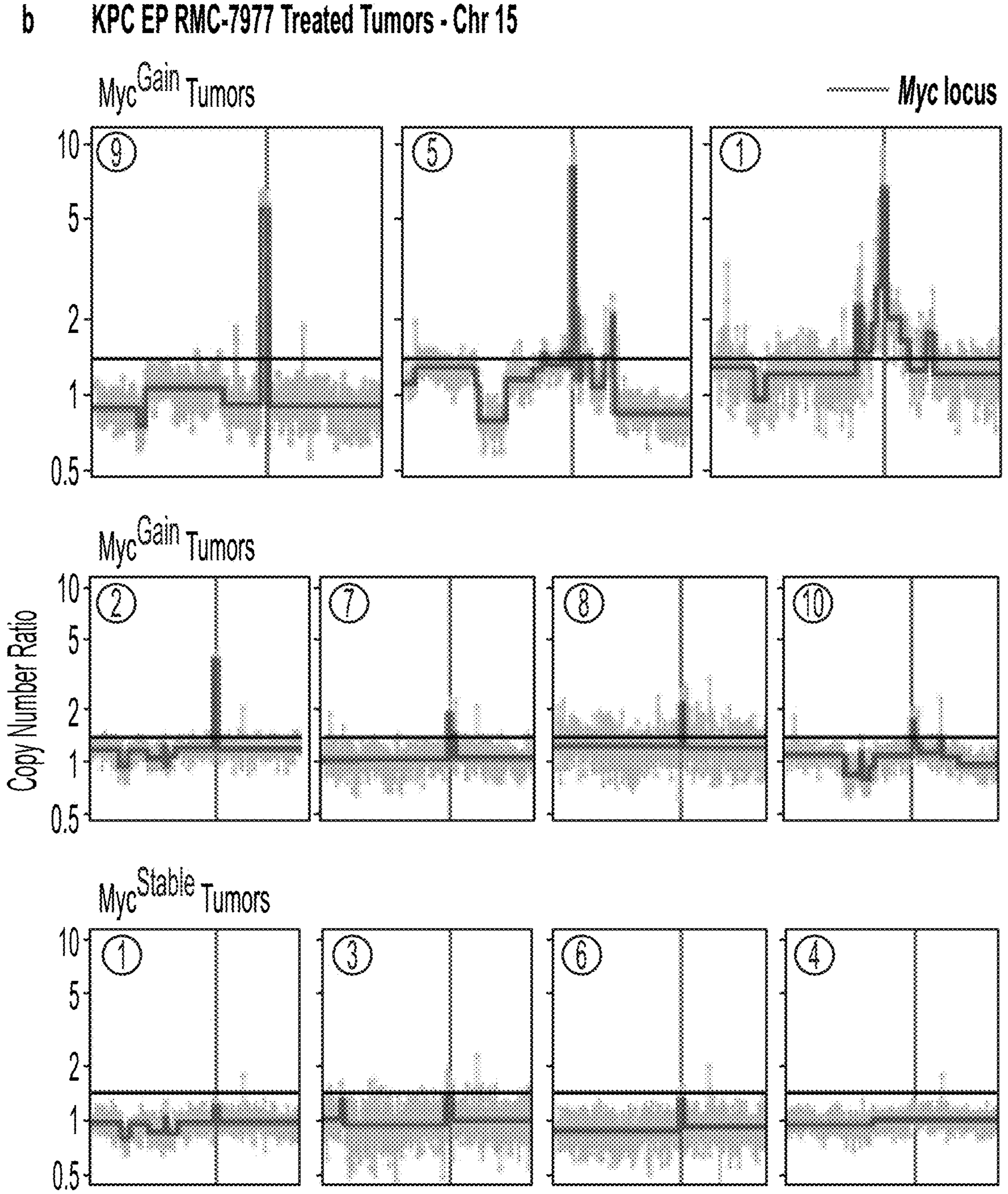
Figure 12A:
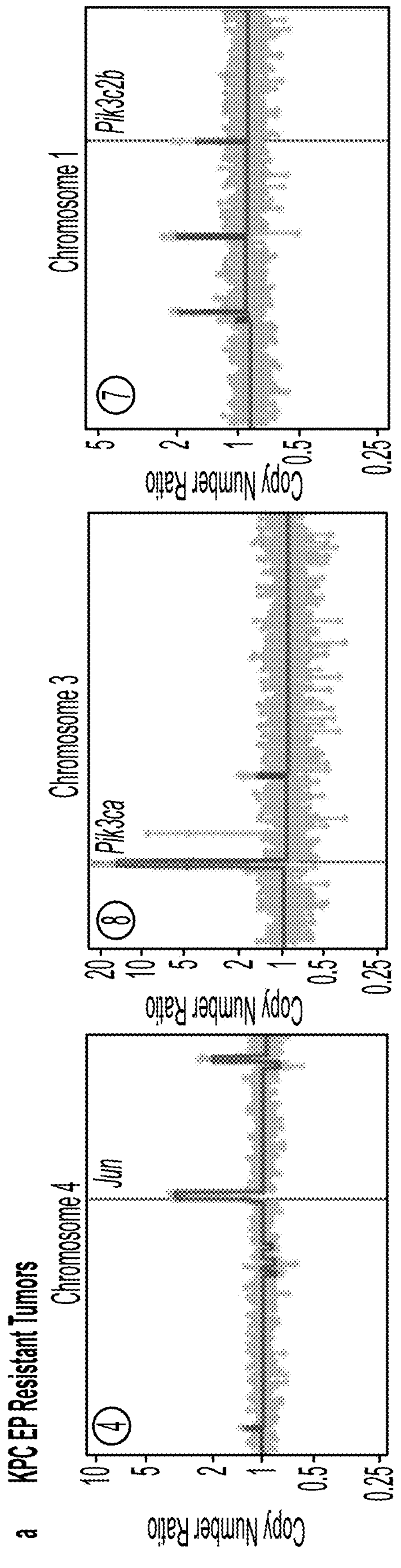
FIGS. 12A-12C: (a) CNV analysis of DNA isolated from epithelial cells of RMC-7977 resistant KPC tumors. Vertical light gray lines mark amplified regions of interest. Letters represent matched tumors from FIG. 5. (b) Targeted sequencing of known cancer-associated genes (mouse IMPACT testing) in RMC-7977 resistant KPC tumors and KPC Vehicle tumors. Vertical light gray lines mark Myc locus. Letters represent matched tumors from FIG. 5. (c) Cell lines derived from RMC-7977-resistant KPC tumors treated with DMSO, RMC-7977, IAG933 or combinations. The dose-response matrix shows combination synergy based on cell viability at different dose pairs. Shades of darker and lighter gray represent synergistic and antagonistic effects respectively.
Figure 12B:
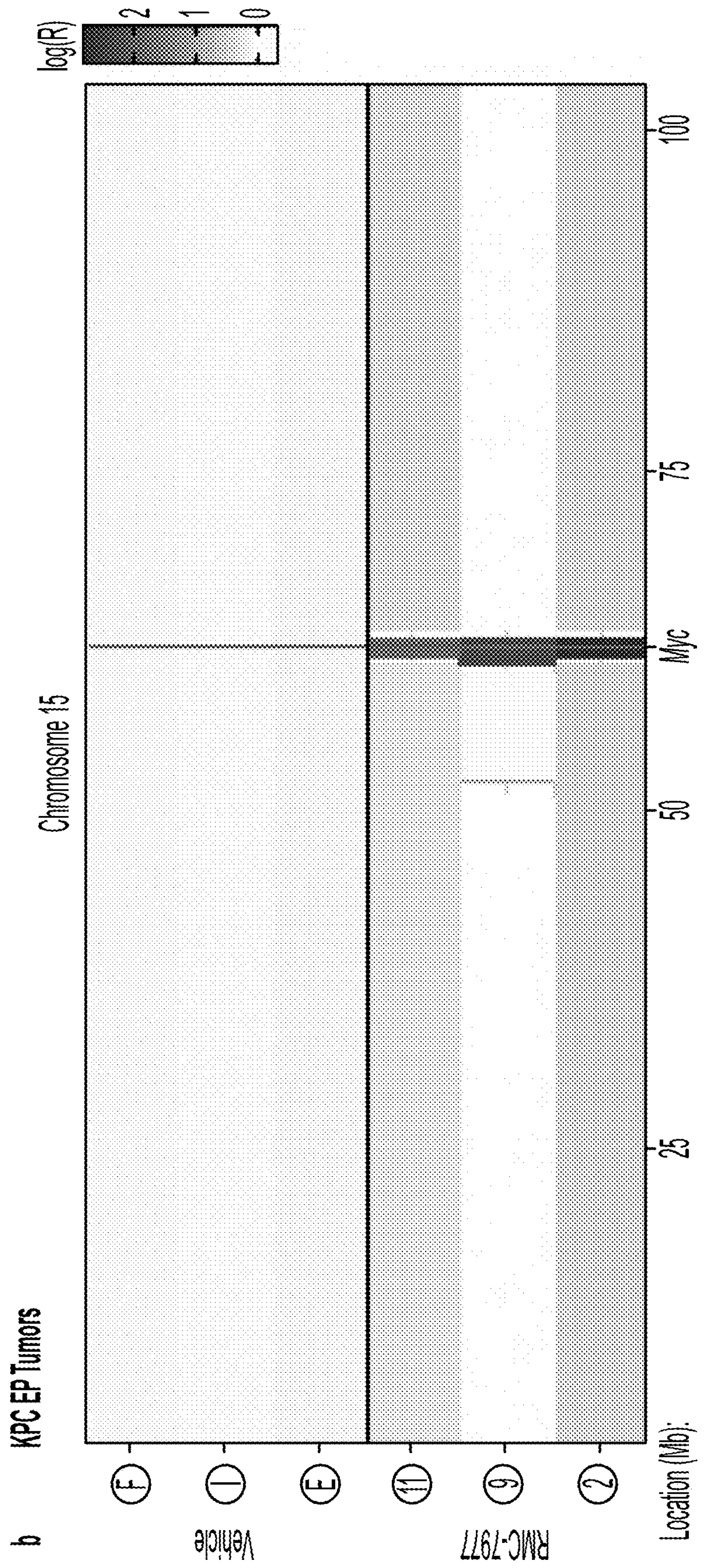

To examine a broader range of potential resistance mechanisms, we used laser capture microdissection to extract DNA from RMC-7977-treated EP tumors (all tumors available at the time of evaluation, Tumors 1-11 in FIG. 5*b*) and performed sparse genome copy number variation (CNV) analysis, comparing both to a set of 5 vehicle-treated EP tumors as well as to historical reference samples comprising primary 15 KPF/+C pancreatic tumors (KPC with a heterozygous conditional null allele)[36] and cell lines from 16 KPCY pancreatic tumors[37]. Overall, the global genomic profiles of RMC-7977 resistant KPC tumors closely reflected those of the reference samples (FIG. 6*a*). However, one prominent exception was apparent: 7 of the 11 (64%) RMC-7977 resistant tumors exhibited focal copy number gains in Myc, an oncogenic transcription factor that receives mitogenic signals from the Ras pathway (FIG. 6*b*). By comparison, only 3 of 36 (8%) control KPC/KPCY samples harbored gains at the Myc locus ($p=0.0003$, Fisher's Exact test). An additional RMC-7977 resistant tumor harbored a focal gain in Jun, a canonical member of the AP1 transcription factor complex that acts downstream of the RAS/MAPK pathway to drive proliferation (FIG. 12*a*); Jun amplifications have rarely been reported in any cancer. Finally, two RMC-7977 resistant KPC tumors harbored focal gains of Pi3k family members (Pik3ca in Tumor 8 and Pik3c2b in Tumor 7), in both cases co-occurring with Myc gains FIG. 12*a,b*). Targeted resequencing of the Myc locus in a subset of EP KPC tumors (3 vehicle- and 3 RMC-7977-treated) provided orthogonal validation of the presence of Myc amplifications in RMC-7977 treated EP tumors (FIG. 12*b*). Together, these data suggest that broad RAS-GTP inhibition with a tri-complex inhibitor like RMC-7977 forces KPC pancreatic tumors down a narrower evolutionary path to resistance as compared to mutation-specific RAS inhibitors (wherein the RAS pathway is frequently reactivated), with the most prominent mechanisms affecting transcription factors downstream of RAS/MAPK signaling.

Figure 6C:
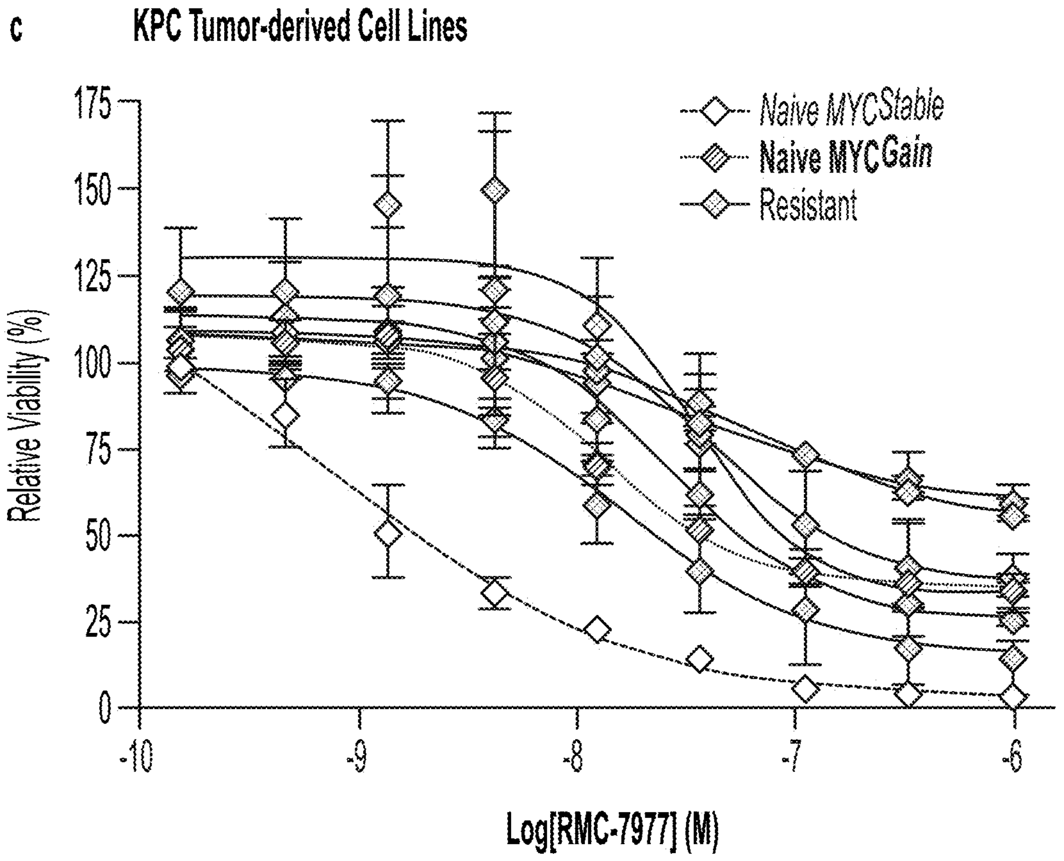

To further investigate the relevance of Myc amplifications, we established cell lines from 6 RMC-7977 resistant tumors, of which four were confirmed to harbor Myc gains. All six lines from resistant tumors were less sensitive to RMC-7977 than a control KPC cell line (K8484) derived from a treatment-naive KPC tumor and confirmed not to have a gain at the Myc locus (MycStable) (FIG. 6*c*). Another treatment-naive KPC cell line (K2293) was identified with spontaneous Myc gains (MycGain) and found to have correspondingly lower sensitivity to RMC-7977. We then used mass-spectrometry based proteomics to compare the effects of RMC-7977 vs. DMSO treatment in one MycGain resistant line (K18509R) and the naive MycStable line (K8484) (FIG. 6*d*) and queried the differential protein expression signatures within each line for enrichment of functional gene sets. While both lines showed loss of an experimental MAPK pathway gene expression signature (see Methods) upon RMC-7977 treatment, many more proteins were differentially expressed between upon RMC-7977 treatment in the MycStable than in the MycGain resistant lines (FIG. 6*d*, compare variance along vertical and horizontal axes.

Figure 6D:
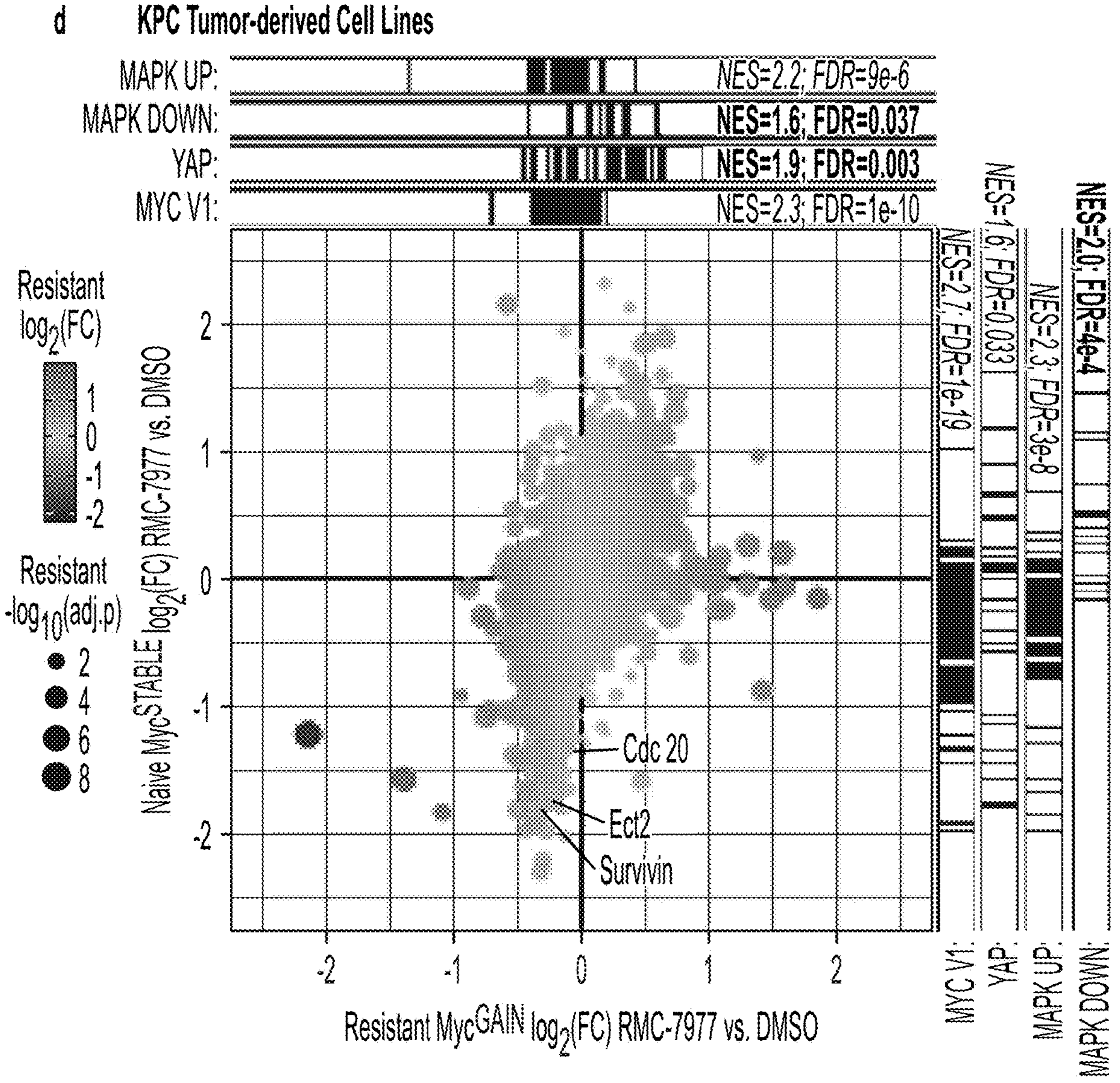
Figure 6E:
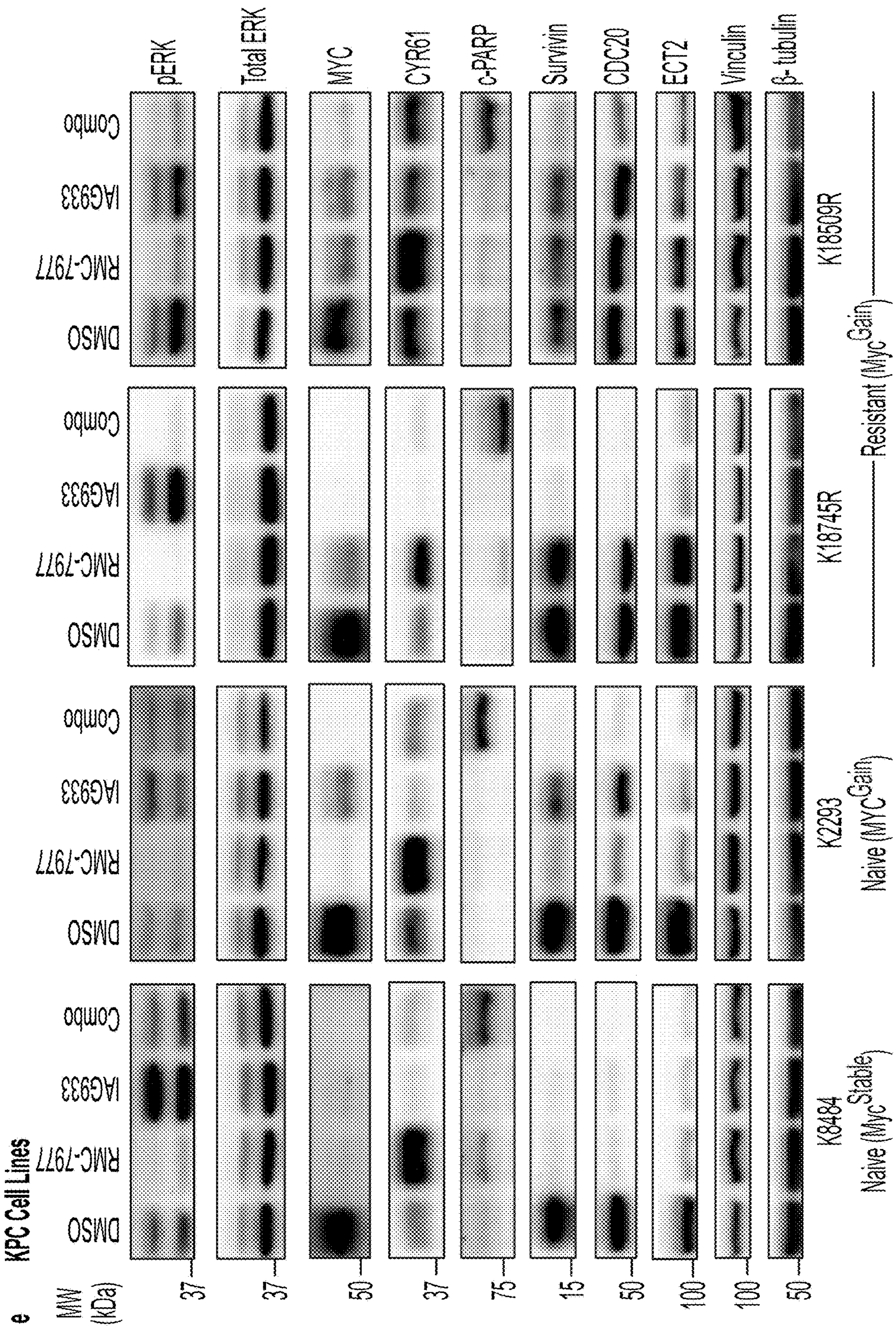
Figure 6F:
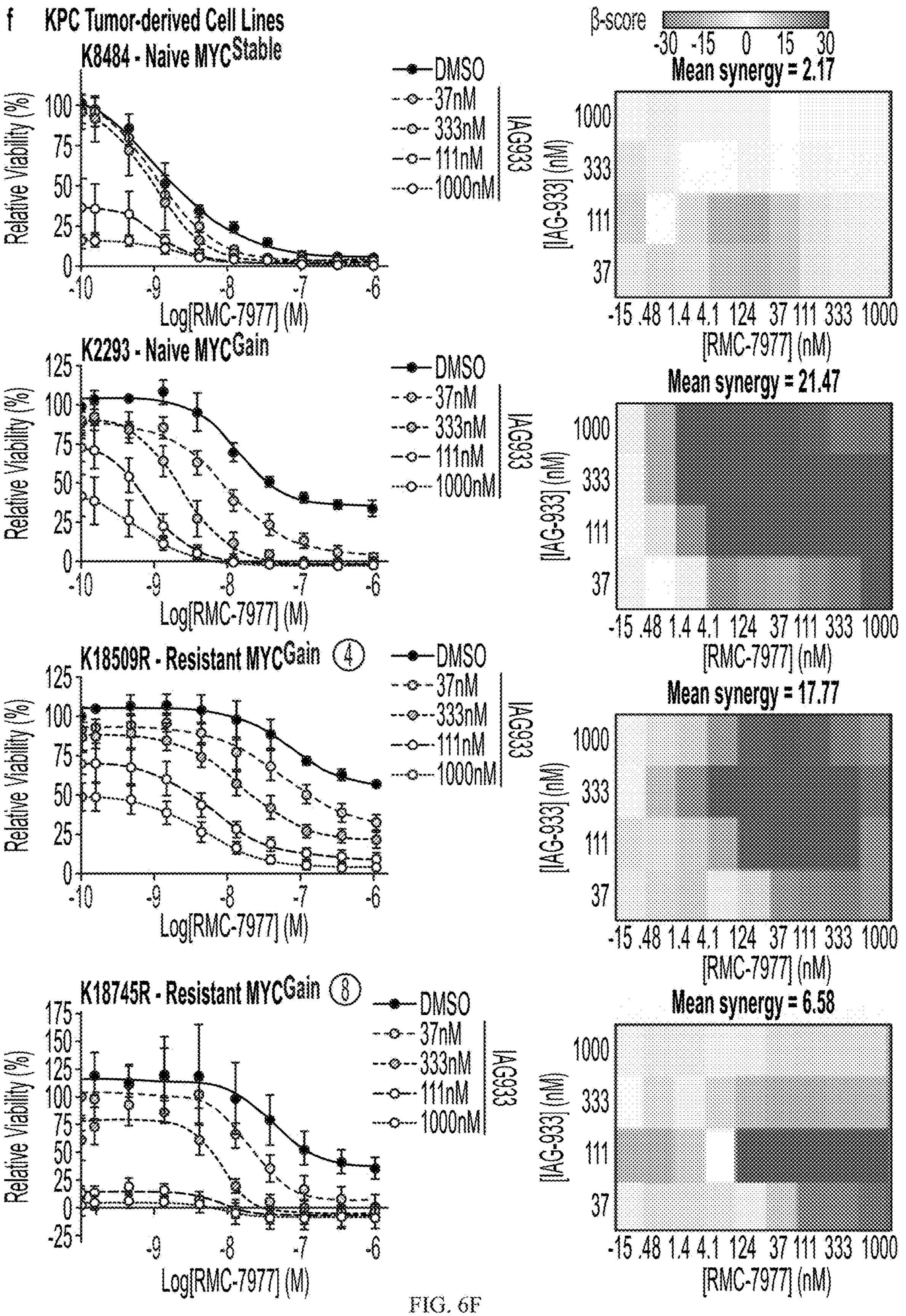
Figure 12C:
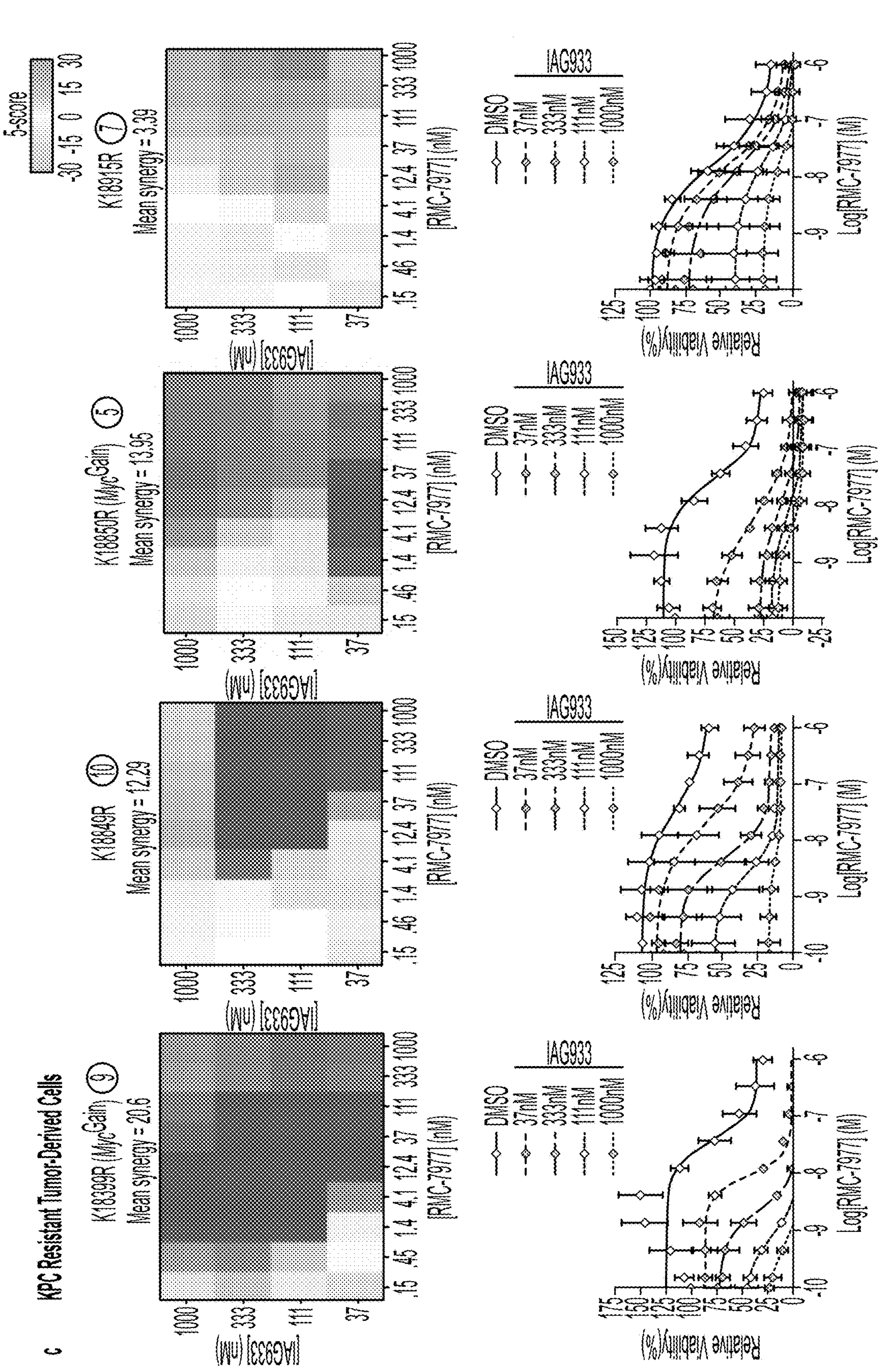

Among the gene sets that diverged between the two cell lines, a Yap/Taz response signature stood out as being reduced by RMC-7977 in the sensitive line but activated in the resistant line (FIG. 6*d*). This led us to hypothesize that the Yap/Taz pathway may be crucial for supporting Myc-driven resistance to RMC-7977. To pharmacologically test this, we examined the response of KPC-derived cell lines to the pan-TEAD inhibitor IAG9[33,38] either alone or in combination with RMC-7977. Western blot analysis found that Myc protein levels were fully inhibited in two RMC-7977 Naive lines, whereas Myc was incompletely reduced in two Resistant lines (FIG. 6*e*). However, the addition of IAG933 in combination with RMC-7977 fully inhibited Myc levels in the Resistant lines. Finally, dose-escalation experiments using RMC-7977 in combination with IAG933 found that these agents have synergistic effects on cell viability across all lines tested, suggesting a means to counteract resistance to $RAS^{MULTI}$(ON) inhibition (FIG. 6*f*, FIG. 12*c*).

The alluring possibilities of a mutation-agnostic RAS inhibitor as a therapeutic agent for RAS-addicted cancers have been inseparably entangled with the widely held assumption that targeting wild-type RAS in humans would prove intolerable. Indeed, there was little evidence available from mouse models to guide expectations for the effects of widespread inhibition of canonical RAS family members. Homozygous knockout of Kras produces an early (e3.5) embryonic lethal phenotype[21] and conditional deletion in hematopoietic lineages eventually compromises hematopoiesis[21]. However, neither of these experiments accurately model the inhibition of RAS in humans that could be achieved with a small molecule, broad-spectrum RAS inhibitor. Perhaps the closest parallel is the systemic inhibition of C-MYC (which serves as a conduit for RAS signaling in many cell types) through the inducible expression of the dominant negative protein Omomyc[39]. This approach showed that inhibition of physiological MYC activity reduced proliferation in most epithelial tissues, but that key epithelial functions were broadly maintained for extended periods of time. Systemic RAS inhibition may prove to be similar in nature, with tolerability enabled by the relatively low levels of active RAS-GTP (the target for RMC-7977) in normal tissues[40] and the somewhat reduced affinity of RMC-7977 for wild type RAS as compared to mutant variants[14]. This is consistent with prior work showing that normal cells can rapidly restore homeostasis following RAS pathway inhibition in contrast to RAS-addicted tumor cells[41]. By contrast, the distinct anti-proliferative, pro-apoptotic effects of RMC-7977 in mutant-KRAS harboring tumor cells relative to normal tissues are consistent with the concept of "oncogene addiction" and explain the remarkable extension of overall survival we observed in the highly chemoresistant KPC mouse model.

As more multi-specific RAS-GTP inhibitors such as RMC-6236 progress through clinical development, the critical questions of response duration and mechanisms of resistance will become central. PDAC is a remarkably plastic malignancy, capable of adapting to and overcoming extreme environments and aggressive interventions. However, aberrant RAS signaling is the fundamental pillar on which PDAC biology is built; the clinical experience with approved RASG12C inhibitors, particularly in NSCLC, indicates that restoration of mitogenic RAS signaling is a frequent and preferred resistance mechanism in tumors if given the opportunity. Our evidence suggests that targeting both mutant and wild-type RAS proteins makes the path to resistance steeper for pancreatic tumors, largely precluding some of the mechanisms that are commonly observed with mutation-selective RAS pathway inhibitors. Myc alterations common in patients whose tumors progress on treatment following broad-specificity RAS-GTP inhibition could benefit from the combined targeting of the RAS and YAP/TAZ/TEAD. Taken together, our findings have significant and positive implications for the translation of $RAS^{MULTI}$ (ON) inhibitors, as exemplified by RMC-6236 monotherapy, in patients with pancreatic ductal adenocarcinoma and other types of RAS-addicted cancers.

Material and Methods

RMC-7977 Formulation

For in vitro studies RMC-7977 was re-suspended in DMSO (Fisher Bioreagents, BP231-100) and used at 10 mM stock concentration. For use in the in vivo studies RMC-7977 was prepared using a formulation made of 10/20/10/60 (% v/v/v/v) DMSO/PEG 400/Solutol HS15/water. The same vehicle formulation was used for all control groups.

Cell Culture and Reagents

Patient-derived xenograft (PDX) human PDAC cell lines were provided by Dr. Anirban Maitra (MD Anderson Cancer Center): Pa01C, Pa02C, Pa14C, and Pa16C. hF39 and hF43 cell lines were provided by Dr. David Tuveson (Cold Spring Harbor Laboratory). The UM147 PDX cell line was obtained from University of Michigan (PMID: 17283135). PaCaDD-137 and PaCaDD-165 were obtained from the German Collection of Microorganisms and Cell Cultures GmbH (DSMZ, world wide web dsmz.de/). All remaining cell lines were obtained from the American Type Culture Collection (ATCC). Cell lines were grown in appropriate medium supplemented withl % penicillin/streptomycin and fetal bovine serum (FBS) at 15% for UM147 or 10% for all other cell lines and maintained at 37° C. in a humidified incubator at 5% $CO_2$, unless otherwise indicated. PaCaDD-137 and PaCaDD-165 were cultured in 80% mixture of DMEM and Defined Keratinocyte SFM (at 1:1 ratio) supplemented with Pen-Strep at 1% and FBS at 20%. Murine PDAC cell lines were derived from tumor-bearing KPCY (6419c5, 2838c342) or KPC (4662-G12D43) animals on a congenic C57BL/6 background. The 4662-G12C line was generated using CRISPR/Cas9 to replace the endogenous G12D mutation from 4662-G12D cells with the G12C mutation by lentiviral transduction. KRAS allele states were confirmed by genomic sequencing. RMC-7977-resistant murine cell lines were generated from KPC mice treated with RMC-7977 until endpoint. Cells were cultured in Dulbecco's modified Eagle medium (DMEM, high glucose without sodium pyruvate) supplemented with 10% heat-inactivated FBS and 1% penicillin/streptomycin. RMC-7977 at 10 nM was added to the resistant cell lines during maintenance.

PRISM Assay

Cell Lines

The PRISM cell set consisted of 796 cell lines representing more than 45 lineages, which largely overlapped with the Cancer Cell Line Encyclopedia (CCLE) (portals.broadinstitute.org/ccle). Cell lines were grown in RPMI without phenol red, supplemented with 10% or 20% FBS for adherent and suspended lines, respectively. Parental cell lines were stably infected with a unique 24-nucleotide DNA barcode via lentiviral transduction and blasticidin selection. After selection, barcoded cell lines were expanded and subjected to quality control (mycoplasma contamination test, a SNP test for confirming cell line identity, and barcode ID confirmation). Approved cell lines were then pooled (20-25 cell lines per pool) based on doubling time similarity and frozen in assay-ready vials.

PRISM Screening

RMC-7977 was added to 384-well plates at 8-point concentration with 3-fold dilutions in triplicate. These assay-ready plates were then seeded with the thawed cell line pools. Adherent cell pools were plated at 1250 cells per well, while suspension and mixed adherent/suspension pools were plated at 2000 cells per well. Treated cells were incubated for 5 days, then lysed. Lysate plates were collapsed together prior to barcode amplification and detection.

Barcode Amplification and Detection

Each cell line's unique barcode is located in the 3'UTR of the blasticidin resistance gene and therefore is expressed as mRNA. Total mRNA was captured using magnetic particles that recognize polyA sequences. Captured mRNA was reverse-transcribed into cDNA and then the sequence containing the unique PRISM barcode was amplified using PCR. Finally, Luminex beads that recognize the specific barcode sequences in the cell set were hybridized to the PCR products and detected using a Luminex scanner which reports signal as a median fluorescent intensity (MFI).

Data Processing

Each detection well contained 10 control barcodes in increasing abundances as spike-in controls. For each plate, we first create a reference profile by calculating the median of the log 2(MFI) values across negative control wells for each of these spiked-in barcodes.

For each well, a monotonic smooth p-spline was fit to map the spike in control levels to the reference profile. Next, we transform the log 2(MFI) for each cell barcode using the fitted spline to allow well-to-well comparisons by correcting for amplification and detection artifacts. Next, the separability between negative and positive control treatments was assessed. In particular, we calculated the error rate of the optimum simple threshold classifier between the control samples for each cell line and plate combination. Error rate is a measure of overlap of the two control sets and was defined as Error=(FP+FN)/n, where FP is false positives, FN is false negatives, and n is the total number of controls. A threshold was set between the distributions of positive and negative control log 2(MFI) values (with everything below the threshold said to be positive and above said to be negative) such that this value is minimized. Additionally, we also calculated the dynamic range of each cell line. Dynamic range was defined as $DR=\mu-–\mu+$, where $\mu+/–$ stood for the median of the normalized log MFI values in positive/negative control samples.

We filtered out cell lines with error rate above 0.05 or a dynamic range less than 1.74 from the downstream analysis. Additionally, any cell line that had less than 2 passing replicates was also omitted for the sake of reproducibility. Finally, we computed viability by normalizing with respect to the median negative control for each plate. Log-fold-change viabilities were computed as log-viability=log 2(x)–log 2(μ–), where log 2(x) is the corrected log 2(MFI) value in the treatment and log 2(μ–) is the median corrected log 2(MFI) in the negative control wells in the same plate.

Log-viability scores were corrected for batch effects coming from pools and culture conditions using the ComBat algorithm[44].

We fit a robust four-parameter logistic curve to the response of each cell line to the compound: f(x)=b+(a−b)/(1+es log(x/EC50)) with the following restrictions:

We require that the upper asymptote of the curve be between 0.99 and 1.01

We require that the lower asymptote of the curve be between 0 and 1.01

We do not enforce decreasing curves

We initialize the curve fitting algorithm to guess an upper asymptote of 1 and a lower asymptote of 0.5

When the standard curve fit fails, we report the robust fits provided by the dr4pl R-package and computed AUC values for each dose-response curve and IC50 values for curves that dropped below 50% viability.

VII. Finally, the replicates were collapsed to a treatment-level profile by computing the median log-viability score for each cell line.

Associations between inhibitor sensitivity Area Under the Curve (AUC) and mutations For every gene with non-silent mutations in at least four cell-lines, we compared the AUC values between cells with and without those mutations using a t-test. This analysis was carried out for: (i) the full dataset; (ii) excluding cell lines with non-silent KRAS mutations; and (iii) excluding cell lines that have either KRAS or NRAS non-silent mutations.

Bioinformatics Analyses

Gene mutation, gene expression, and lineage data were downloaded from the 22Q4 release of the DepMap Data Portal[45]. For tumor models with no publicly available data, we carried out whole exome sequencing to ascertain gene mutations and RNA sequencing to ascertain gene expression. DNA mutation calling was accomplished with TNSeq using the hg38 version of the human genome[46]. Functional annotation of the resulting mutation calls was accomplished with Variant Effect Predictor and further annotated with oncoKB47. Gene expression was quantified using salmon against the hg38 version of human transcriptome further processed using txlmport and edgeR to generate normalized counts[48-50].

Murine Cell Viability Assays

PDAC murine cell lines harboring KrasG12D or KrasG12C mutations were seeded at $2\times10^3$ in a 96-well plate. Cells were treated 24 hours later with DMSO or serial dilutions of RMC-7977. Cell viability was evaluated 72 hours later by measuring adenosine triphosphate (ATP) levels using the CellTiter-Glo® Luminescent Cell Viability Assay (Promega, G7572) according to the manufacturer's instructions. For experiments comparing naive and resistant cell lines, live cells were fluorescently labelled using Calcein AM (20-minute incubation at 500 nM, Thermo Fisher) and counted using the SpectraMax i3X multimode detection platform (Molecular Devices). Technical triplicates were run for each biological replicate and a total of 3-4 biological replicates was done for each cell line. Growth percentage was calculated by normalizing drug-treated values to DMSO control, which was set to 100%. Four-parameter drug response curves were generated from 3+ biological replicates in GraphPad Prism. Mean±s.d. was plotted for each tested dilution.

For synergy evaluation testing, RMC-7977 treatment naive and resistant cell lines, a similar protocol was used with the following change: 24 hours post cell line seeding—RMC-7977, IAG933 (Nantong Hi-future Biotechnology Co., Ltd, CAS: 2714434-21-4), or the combinations of these drugs as indicated were added to the cells using the D300e digital dispenser (Tecan).

Human Cell Line Proliferation Assay

19 PDAC cell lines were tested for sensitivity to RMC-7977 as part of a panel of human cancer cell lines of various histotypes screened at Crown Bioscience. These PDAC cell lines harbored KRASG12D, KRASG12V, KRASG12C, KRASQ61H, and BRAFV487_P492delinsA mutations. To measure inhibition of cell proliferation, cells were cultured in methylcellulose and treated in triplicates with serial dilutions of RMC-7977 (top concentration of 1 μM) or DMSO dispensed by a Tecan D300e digital dispenser (Tecan Trading AG). Cells were incubated for 120 hours prior to measurement of ATP levels using CellTiter-Glo. Technical triplicates were run for each biological replicate and a total of three biological replicates was done for each cell line. CTG assay readouts were plotted as a function of log molar [inhibitor] and a 4-parameter sigmoidal concentration response model was fitted to the data. Mean±s.d. was plotted for each tested dilution.

PDAC cell lines harboring KRASWT or KRASQ61H were plated at 500-4,000 cells/well in clear, flat-bottomed 96-well plates (Corning) and grown for 24 h prior to adding indicated concentration of RMC-7977 or DMSO using the D300e digital dispenser (Tecan). Following treatment, cells were incubated for additional 3-5 days after which live cells were fluorescently labelled using Calcein AM (20-minute incubation at 500 nM, Thermo Fisher) and counted using the SpectraMax i3X multimode detection platform (Molecular Devices). Experiments were day 0 normalized using an independent culture plate. Growth percentage was calculated by normalizing drug-treated values to DMSO control, which was set to 100%. Four-parameter sigmoidal concentration response models were fitted to the data from 3 or more biological replicates. Mean±s.d. was plotted for each tested dilution.

Western Blot Analysis

Cells were seeded at $7.5\times10^5$-$4\times10^6$ cells per well in 6-well plates or 100 mm dishes in growth medium. After overnight incubation, indicated compound (RMC-7977, IAG933 or DMSO (0.1% v/v)) were added and incubated for the indicated time points. Cells were washed twice with ice-cold PBS and lysed with NP-40 lysis buffer (Thermo Fisher Scientific, J60766), MSD Tris Lysis Buffer (MSD, R60TX-2), RIPA buffer (50 mM TRIS-HCl, pH 7.5, 150 mM NaCl, 1% NP-40, 0.5% sodium deoxycholate, 0.1% SDS) or a lysis buffer containing 1% Triton X-100, 20 mM Tris-HCl, 150 mM NaCl, and 1 mM EDTA. All lysis buffers were supplemented with protease and phosphatase inhibitors. Lysates were scraped and collected before centrifugation at 21,000×g for 10 minutes at 4° C. The protein-containing supernatants were quantified by BCA assay (Pierce, 23225) and equal quantities of protein were denatured with LDS and reducing agent at 95° C. Samples were resolved on 12% or 4-12% Bis-Tris polyacrylamide gels, then transferred to a nitrocellulose or PVDF membrane using the iBlot 2.0 system or wet transfer. Membranes were blocked in Intercept TBS buffer (LiCor, 927-60001) or 3-5% milk before probing with primary antibodies overnight at 4° C. Secondary antibodies were added as appropriate, and the membranes were imaged on a LiCor Odyssey imager. Alternatively, membranes were incubated with HRP-linked secondary antibodies and developed with Clarity or ClarityMax chemiluminescent substrates using a ChemiDoc XRS+ or ChemiDoc™ MP imager (Bio-Rad).

PDAC Organoid Preparation and Treatment Conditions

Origins and Genetic Profiling of Patient-Derived Organoids

Genetic profiling was performed on the patients' tissue biopsies using whole-genome sequencing or OncoPanel[43,51]. All patients consented to an Institutional Review Board (IRB)-approved protocol at Dana-Farber Cancer Institute permitting access to their clinical and genomic data.

Organoid Culture

Organoids were cultured at 37° C. in 5% $CO_2$. Cells were seeded in growth factor reduced Matrigel (Corning; Cat. #356231) domes and incubated with human organoid medium formulated as follows: Advanced DMEM/F12-based-conditioned medium, 1×B27 supplement, 10 mM HEPES, 2 mM GlutaMAX, 10 mM nicotinamide, 1.25 mM N-acetylcysteine, 50 ng/mL mEGF, 100 ng/mL hFGF10, 0.01 M hGastrin I, 500 nM A83-01, Noggin 100 ng/mL, 1×Wnt-3A conditioned 10% FBS DMEM (50% by volume) and 1×R-spondin Conditioned Basal Medium (10% by volume)[52,53]

Organoid Drug Treatment and Viability Assay

Organoids were dissociated using TrypLE Express (Thermo Fisher, Cat. #12604054) and cells were seeded into ultra-low attachment 384-well plates at $1\times10^3$ cells per well into 201 of culture media, consisting of 10% Matrigel and 90% human organoid medium. Organoids were treated 24 hours post seeding over a 12-point dose curve with RMC-7977 or with DMSO in a randomized fashion using a Tecan D300e Digital Dispenser. Cell viability was assessed 6 days post-treatment using a Cell-TiterGlo 3D Cell Viability assay (Promega, G9683), according to the manufacturer's instructions. Fluorescence was read using a FLUOstar Omega microplate reader. Technical triplicates were analyzed for each biological replicate and a total of three biological replicates were done for each cell line. CTG assay readouts were plotted as a function of log molar [inhibitor] and a 4-parameter sigmoidal concentration response model was fitted to the data. Mean±s.d. was plotted for each dilution.

Ex Vivo Human PDAC Explant Preparation and Treatment Conditions

Explant culture sponges and optimized culture media were prepared as previously described in Hasselluhn and Decker-Farrell et al.[54]. Human tissue samples were obtained from de-identified patients undergoing resection surgeries, primarily pancreaticoduodenectomy (Whipple) or distal pancreatectomy, at New York-Presbyterian/Columbia University Irving Medical Center. Upon receipt of a resected human PDAC fragment (n=4), each tissue sample was cut into 300 m slices using a Compresstome. Any tumor tissue remaining after sectioning was fixed in 4% paraformaldehyde (Santa Cruz Biotechnology, sc-281692) for 2 hours, at 4° C. as the Day 0 control. Sectioned slices were next placed between gelatin sponges pre-soaked in 750 µl of media containing either DMSO or varying concentrations of RMC-7977 (10-100 nM). Each well of a 24 well plate contained one explant slice placed between bottom sponge (1 $cm^3$) and a top sponge (2-3 mm thick). After 24 hours culture, explants were collected and fixed in 4% PFA for 2 hours. Fixed tissue was then transferred to 70% ethanol and paraffin embedded for long-term storage and further analysis.

In Vivo Xenograft Studies

Animal Studies

Studies were conducted at the following CROs: GenenDesign (Shanghai, China), Pharmaron (Beijing, China), and Wuxi AppTec (SuZhou, China). All CDX/PDX mouse studies and procedures related to animal handling, care and treatment were conducted in compliance with all applicable regulations and guidelines of the relevant Institutional Animal Care and Use Committee (IACUC). Female BALB/c nude mice and NOD SCID mice 6-8 weeks old from Beijing Vital River/VR Laboratory Animal Co., LTD, Beijing Ani-Keeper Biotech Co., Ltd., and Shanghai Sino-British SIPPR/BK Laboratory Animal Co., LTD were used for these studies.

Generation of Xenograft Models

In order to generate subcutaneous xenograft tumors each mouse was inoculated at the right flank with tumor cells ($2\times10^6$-$1\times10^7$) in 100-200 µl of media/PBS supplemented with Matrigel (1:1). Treatments were started when the average tumor volume reached 150-250 $mm^3$ (for tumor growth evaluation) and 400-600 $mm^3$ (for single dose pharmacokinetic/pharmacodynamic (PK/PD) study). Tumor diameter was measured in two dimensions using a digital caliper, and the tumor volume in $mm^3$ was calculated using the formula: Volume=((width)2×length)/2. Mice on studies were weighed and tumors were measured 2 times a week.

The human primary cancer xenograft models were generated using fresh tumor fragments obtained from hospitals with informed consent from the patients in accordance with protocols approved by the Hospital Institutional Ethical Committee (IEC). The tumor fragments were serial passaged in BABL/c nude mice and then cryopreserved for further use. For this study, recovered tumor fragments of about 15-30 $mm^3$ in size from each model were implanted into right flanks of BALB/c nude mice. Treatment started when average tumor volume reached 150-250 $mm^3$.

To generate orthotopic xenograft tumors, survival surgeries were carried out and $2\times10^6$ $5\times10^6$ luciferase-expressing tumor cells in 30-50 µL Media/Matrigel mixtures (1:1) were implanted directly into the mouse pancreas. Treatments were started when the tumors produced an average of $50\text{-}80\times10^7$ photon/second as measured by the in vivo imaging system (IVIS). All subsequent tumor measures were also conducted by IVIS. For routine monitoring, mice were injected intraperitoneally with 15 mg/mL (at 5 µL/g BW) of D-Luciferin (Perkin Elmer) and imaged, after which Living Image software (Perkin Elmer) was used to compute regions of interest (ROI) and tumor volumes.

RMC-7977 Treatment

Tumor-bearing animals were randomized and assigned into groups (n=3-10/group). Vehicle or RMC-7977 was administered via oral gavage daily at 10 mg/kg and animals were treated for 21-28 days. Studies were terminated early if tumor burden reached humane endpoint. Body weights were collected twice a week during the study. Means±s.e.m were plotted in the waterfall plots. For the single-dose pharmacokinetic/pharmacodynamic (PK/PD) study, mice were randomized and assigned into groups (n=3-6/dose/timepoint). A single dose of RMC-7977 was administered orally at 10 mg/kg, 25 mg/kg and 50 mg/kg. Tissues (including tumor, colon and skin) were harvested at indicated time points and either fixed in 10% formalin, embedded in Optimal Cutting Temperature (OCT; Sakura, 4583) solution or snap-frozen in LN2 for further analysis. Whole blood was transferred into K2EDTA Microtainer tubes (BD, 365974), incubated for 5 minutes and snap-frozen in LN2.

In Vivo Allograft Studies

Animal Studies

All murine allograft studies and procedures related to animal handling, care and treatment were conducted in compliance with all applicable regulations and guidelines of the Institutional Animal Care and Use Committee (IACUC). Female C57BL/6J (strain 000664) mice aged 6-8 weeks from the Jackson Laboratory (Bar Harbor, ME USA) were used for these studies.

Generation of Allograft Models

In order to generate subcutaneous (SC) allograft tumors, each mouse was inoculated in the right flank with $3\times10^5$ of KPCY 6499c4 tumor cells in 0.1 ml of Matrigel:PBS (1:1). Treatments were started when the average tumor size reached 140 $mm^3$. Tumor size was measured at two dimensions using a digital caliper, and the tumor volume in $mm^3$ was calculated using the formula: Volume=((width)2× length)/2. Mice on studies were weighed and tumors were measured 2 times a week.

To generate orthotopic allograft tumors, $5\times10^4$ KPCY 6499c4 tumor cells in 20 μL PBS/Matrigel mixtures (1:1) were implanted directly into the mouse pancreas through a laparoscopic incision. Treatments were started when the average tumor size reached −50 $mm^3$. Body weights were measured and tumor growth was monitored by ultrasound twice weekly.

RMC-7977 Treatment

Tumor-bearing animals were randomized, assigned into groups (n=9-10/group), and treated daily via oral gavage with Vehicle or RMC-7977 (10 mg/kg, q.d.). For SC KPCY study, survival endpoint was defined as: tumor volume reaching 2000 $mm^3$ or mice showing any clinical signs, including severe ulceration. For orthotopic KPCY study, survival endpoint was defined as (1) mice showing any clinical signs including hunching or fluid in the abdomen, or (2) tumor dimensions exceeding the imaging frame of the ultrasound. Body weights were measured twice a week during the study. Tissue was harvested either at 4 hours or 24 hours after last dose and preserved as previously described (See Xenograft studies section).

In Vivo GEMM Studies

Animal Breeding

All animal research experiments were approved by the Columbia University Irving Medical Center (CUIMC) Institutional Animal Care and Use Committee (IACUC). Mouse colonies were bred and maintained with standard mouse chow and water, ad libitum, under a standard 12 hr light/12 hr dark cycle. KPC (KrasLSL.G12D/+; p53LSL.R172H/+; Pdx1-Cre), KC (KrasLSL.G12D/+; Pdx1-Cre), PC (p53LSL.R172H/+; Pdx1-Cre) as well as KPf/fC (KrasLSL.G12D/+; p53flox/flox; Pdx1-Cre), KPf/f (KrasLSL.G12D/+; p53flox/flox) and Pf/fC (p53flox/flox; Pdx1-Cre) mice were generated in the Olive Laboratory at Columbia University, by crossing the described alleles. Mouse genotypes were determined using real time PCR with specific probes designed for each gene (Transnetyx; Cordova, TN). KrasLSL-G12D/+; p53LSL-R172H/+, Pdx1-Cre, Rosa26YFP/YFP (KPCY) were bred and maintained in pathogen-free facilities at the University of Pennsylvania.

Pharmacokinetic/Pharmacodynamic Study in KPF/FC

Tumor formation in KPF/FC (KrasLSL.G12D/+; p53flox/flox; Pdx1-Cre) mice was monitored by bi-weekly palpations until the detection of a mass, which was then confirmed by ultrasound. Tumor-bearing mice were randomized and assigned into groups (n=3/dose/timepoint). Single dose of RMC-7977 was administered orally at 10 mg/kg, 25 mg/kg and 50 mg/kg. The same vehicle formulation was used for the control group. Whole blood and tissue (tumors and colons) were harvested at indicated time points preserved as previously described (See Xenograft studies section).

Pharmacodynamic Study in KPC Mice

Tumor formation in KPC mice was monitored by bi-weekly palpation. Upon detection of a 4-7 mm diameter tumor by ultrasound, KPC mice were randomized and treated with Vehicle (n=6) or RMC-7977 (50 mg/kg; n=11). Treatments were performed every other day via oral gavage for 1 week. Animal health status and weight were checked daily and ultrasounds (Vevo 3100) were performed every third day to monitor tumor growth. Following two consecutive ultrasounds, RMC-7977-treated animals were sacrificed either 4 (n=7) or 24 hours (n=4) after last dose and Vehicle-treated animals were sacrificed between 4-24 hours post last dose. Tissue was harvested and preserved as previously described (See Xenograft studies section). Additional group of KPC mice was also treated with a single dose of RMC-7977 (n=10) or Vehicle (n=3) and tissues were harvested at 4 or 24 hours post dose as previously described.

Pharmacodynamic Study in KPCY Mice

KPCY mice were enrolled upon detection of a 15-100 $mm^3$ tumor measured via ultrasound. Animals were randomized into groups and treated with Vehicle (n=6) or RMC-7977 (25 mg/kg; n=8). Treatments were performed every day via oral gavage for 15 days and ultrasounds were performed on day 8 and 15. Animals were sacrificed after last dose and tissue was collected and preserved as previously described (See Xenograft studies section).

Survival Study in KPC Mice

For survival study, KPC mice with 4-7 mm diameter tumors (as measured by ultrasound) were enrolled and treated every other day with Vehicle (n=9) or RMC-7977 (50 mg/kg; n=13). Animal health status and weight were checked daily and ultrasounds were performed every third day to monitor tumor growth. The survival end point was determined by overall health criteria scoring, where end point is determined by a score of 5 or greater based on the following criteria:

Moribund—immediate euthanasia
Abdominal distention due to hemorrhagic ascites—5 pts
Mild difficulty beathing—5 pts
Hypothermia—5 pts
Abdominal distention due to chylous ascites—3 pts
Loss of over 20% enrollment body weight—3 pts
Failure of grasp test—3 pts Jaundice or pallor—3 pts
Weak grasp test—2 pts
Failure to interact with other mice—1 pt
Hunched—1 pt
Pilorection/failure to groom—1 pt Additional notes were made to better characterize the cause of death upon necropsy, including the presence of macro liver and/or lung metastases, jaundice, and tumor-mediated GI obstructions. Survival is denoted as Kaplan-Meier survival curves compared with a log-rank, Mantel-Cox test. Mice that reached endpoint criteria were sacrificed either at 4 or 24 hours after last dose in a manner consistent with IACUC standards and our own criteria scoring. Tissue was collected at time of necropsy for further analysis.

In Vivo Pharmacodynamic Analysis by qRT-PCR

RNA was extracted from at least 20 mg of indicated OCT or LN2 frozen tissue using an RNeasy Mini Kit (Qiagen, 74104) and a High Throughput Tissue grinder following the manufacturer's protocol. Reverse transcription was carried out using High-Capacity cDNA Reverse Transcription Kit (ABI, 4368814) according to the manufacturer's protocol. The cDNA product was used for qPCR analysis using TaqMan Gene Expression Master Mix (ABI, 4369016) or iTaq Universal SYBR Green Supermix (BioRad, 172-5125) depending on the primer. TaqMan primer probes specific to DUSP6 (human—Hs00737962_m1, murine—Mm00518185_m1, FAM-MGB) and 18S (human—Hs99999901_s1, murine—Mm03928990_g1, FAM-MGB, used as an internal control gene) were used to detect the levels from each sample in duplicates using a 10 μL final reaction volume in a 96 or 384-well plate. Standard primer sequences specific for 18S were used to detect the levels from each sample in duplicates or triplicates using a 10 μL final reaction volume in a 96-well plate. For qPCR, Ct value of MAPK signature genes and 18S were obtained for analysis. Generated Ct value were normalized to 18S, and then the mean relative mRNA expression levels of each sample were normalized to the average of the vehicle control group. Values were plotted as relative change in mRNA expression compared to Vehicle. Means±s.d. were shown. For primer sequences and more information.

Mouse Blood and Tissue Sample Bioanalysis

Whole blood, tumor, colon and skin tissue concentrations of RMC-7977 were determined using liquid chromatography-tandem mass spectrometry (LC-MS/MS) methods. Tissue samples were homogenized with a 5× or 10× volume of homogenization buffer (methanol/15 mM PBS (1:2; v:v) or 15 mM PBS with 10% methanol). An aliquot of whole blood or homogenized tissue (10 or 20 μL) was transferred to 96-well plates (or tubes) and quenched with a 20× volume of acetonitrile/methanol (1:1; v/v) with 0.1% formic acid containing a cocktail of internal standards (IS). After thorough mixing and centrifugation, the supernatant was directly analyzed on a Sciex 6500+ triple quadrupole mass spectrometer equipped with an ACQUITY or Shimadzu UPLC system. An ACQUITY UPLC BEH C18 or C4 1.7 m (2.1×50 mm) column was used with gradient elution for compound separation. RMC-7977 and IS (verapamil or terfenadine) were detected by positive electrospray ionization using multiple reaction monitoring (RMC-7977: m/z 865.4/706.4 or m/z 865.3/833.5; verapamil: m/z 455.2/164.9; terfenadine: m/z 472.3/436.4). The lower limit of quantification was 0.5 ng/mL or 2.0 ng/mL for blood, tumor, and other tissue. BA analysis on blood and tissue samples from xenograft models was run at Wuxi AppTec. BA analysis on blood and tissue samples from allograft models and GEMM was run at Revolution Medicines.

Immunohistochemistry (IHC)

All tissues were fixed for up to 24 hours using 10% neutral buffered formalin and then moved to 70% ethanol for long term storage. All stainings were performed on 4-μm tissue sections. Sections were deparaffinized using a Leica XL ST5010 autostainer, after which slides were subjected to heat-activated epitope retrieval. To block endogenous peroxidases, 20 min incubation in 3% H2O2 (Fisher Scientific) was performed. Slides were further blocked in serum for 1 hour, and primary antibodies were added for overnight incubation at 4° C. The next day, slides were washed and incubated with ImmPRESS HRP Horse Anti-Rabbit IgG Polymer Detection Kit (Vector Laboratories, MP-7401) for 30 min. Following incubation, ImmPACT DAB peroxidase (Vector Laboratories, SK-4100) was used to develop the stain and hematoxylin was used as nuclear counterstain. Stained slides were imaged at 40× magnification. Quantitative analyses of IHC images were performed using ImageJ.

To stain tissues collected from the Capan-1 xenograft model, a similar protocol was used with the following changes. Sections were stained using a Leica BOND automated staining system and primary antibodies were detected with the Leica BOND Polymer detection kit (3-P—PV6119). Stained slides were scanned and digitized with a 3DHistotech Pannoramic whole slide scanner at 20× magnification. Image analysis was performed using HALO software from Indica Labs.

To stain tissues collected from the KPCY allograft model, a Biocare IntelliPATH automation system was used, and primary antibodies were detected with the MACH4-HRP-polymer Detection System (Biocare, MRH534). Stained slides were scanned and digitized with a TissueScope LE (Huron Digital Pathology) whole slide scanner at 20× magnification. Image analysis was performed using HALO software from Indica Labs.

Dual Immunofluorescence (Co—IF)

Manual staining steps were as follows. Slides were backed at 60° C. for 20 minutes, dewaxed, followed by heat induced epitope retrieval using Biocare DIVA Decloaker pH=6.2 at 95° C. for 20 minutes. Sections were then blocked using BioCare Peroxidase block for 10 minutes at room temperature and incubated with primary antibodies (p-S6 or p-ERK) for 45 minutes at room temperature. After washing, slides were incubated with Biocare Mach4 Polymer-HRP for 30 minutes at room temperature before adding Opal 690 at 1:100 in Opal diluent buffer for 10 minutes at room temperature. After washing slides were treated with BioCare DIVA pH=6.2 elution buffer for 20 minutes at 95° C. and allowed to cool to room temperature for 20 minutes. After washing slides were incubated with CK19 for 45 minutes at 1:200 dilution at room temperature followed by incubation with Biocare Mach4 Polymer-HRP for 30 minutes. After washing slides were then incubated with Opal 480 at 1:100 in Opal diluent buffer for 10 minutes at room temperature. Nuclear DAPI stain was conducted for 10 minutes at room temperature before mounting the coverslips onto the slides using Prolong Gold anti-fade aqueous mounting medium.

Whole slide images were generated using a Huron scanner at 20× resolution.

Laser Capture Microdissection (LCM) of Malignant Cells from Tumor Tissue

In order to enrich for the malignant epithelial cells, LCM was performed as described previously[55-56]. Briefly, 8 μm cuts of OCT-embedded tissue blocks were transferred to PEN membrane glass slides and stained with cresyl violet acetate according to manufacturer's protocol. Laser capture microdissection was performed on a PALM MicroBeam microscope (Zeiss), collecting at least 1000 cells per sample. Genomic DNA was extracted and libraries were prepared using the QIAamp DNA Micro kit (Qiagen).

Sparse Whole Genome and Targeted Locus Sequencing

DNA from microdissected KPC tumor tissue was subject to whole genome amplification as described before[57]. TruSeq indexed Illumina sequencing libraries where then constructed from WGA DNA and subjected to sparse whole genome sequencing at a depth of roughly 3 million sequencing reads, enough to enable copy number ascertainment at a bin resolution of ~100 kb. Sequencing libraries were also processed for targeted sequencing of Myc locus at a coverage of ~100×. For sparse whole genome data processing, sequencing reads were mapped to mouse genome build mm9 while skipping the first 50 base pairs containing inline barcoding sequences as well as DOP-PCR quasi-degenerate sequence. Further processing involved indexing and sorting of uniquely mapped reads as well as removal of PCR duplicates. Uniquely mapped sequencing reads were counted in genomic bins/intervals that were computed using a previously developed algorithm while partitioning the genome into 20,000 bins of ~100 kilobases in length as described before[58]. Read counts were subsequently corrected for GC content using LOWESS smoothing algorithm, normalized and segmented using Circular Binary Segmentation (CBS)[59-60]. Given that LCM processing of tissue enriches for cancer cells but does not entirely remove contaminating stromal cells, copy number inference was done relative to the mean of the genome, and not on absolute copy number states. To call amplifications, we conditioned each event to satisfy two criteria: focality in length as well as a low ratio value of above 1.5 normalized depth. For targeted Myc locus sequencing data, processing was done for copy number as well as single nucleotide variant detection. For copy number, FASTQ files are mapped to the target genome using the BWA mapper ('bwa mem'). The BAM files are then processed using the seqDNAcopy library61 to first get pairwise counts for the target sample and control samples ('bam2counts') into bins of 100 bp. The data is then segmented using seqDNAcopy's seqsegment method.

For single nucleotide variant calling, the data processing pipeline for detecting variants in Illumina HiSeq data is as follows. First the FASTQ files are processed to remove any adapter sequences at the end of the reads using cutadapt (v1.6). The files are then mapped using the BWA mapper (bwa mem v0.7.12). After mapping the SAM files are sorted and read group tags are added using the PICARD tools. After sorting in coordinate order, the BAMs are processed with PICARD MarkDuplicates. The marked BAM files are then processed using the GATK toolkit (v 3.2) according to the best practices for tumor normal pairs. They are first realigned using ABRA (v 0.92) and then the base quality values are recalibrated with the BaseQRecalibrator. Somatic variants are then called in the processed BAMs using muTect (v1.1.7) for SNV and the Haplotype caller from GATK with a custom post-processing script to call somatic indels.

Proteomic Data Preparation and Analysis

Proteomic Sample Preparation

K8484 or K18905 cells were treated with either 10 nM RMC7977 or equivalent volume DMSO for 24 hours in triplicate. Lysates were prepared in 400-450 μL of lysis buffer (8 M urea, 50 mM $NH_4HCO_3$ (pH 7.5), 1× protease inhibitor cocktails (Roche) and 1× phosphatase inhibitor cocktails I and II (Sigma-Aldrich)). Lysates were sonicated six times on ice. Following sonication, samples were centrifuged for 10 min at 21,00× g at 4° C. to pellet molecular debris. Cell lysates (1 mg per sample) were reduced with 5 mM DTT for 45 min at 37° C., alkylated with 15 mM iodoacetamide for 30 min in the dark at room temperature, and protein was precipitated at a 1:10 ratio with cold methanol. Protein precipitates were recovered by centrifugation at 5,000 rpm at 4° C. for 45 min and reconstituted in 50 mM ammonium bicarbonate pH 8 to achieve a 0.5 mg/ml concentration. Samples were digested with LysC (Wako, 1:75 w/w) for 2 hours at 37° C., then digested with trypsin (Promega, 1:75 w/w) overnight at 37° C. Digested peptide samples were acidified and desalted using desalting spin columns (Thermo). Eluates were dried via vacuum centrifugation. Peptide concentration was determined using Quantitative Colorimetric Peptide Assay (Pierce).

Four pooled samples were created from the twelve experimental samples, and all were labeled with TMTpro 16plex reagents (Thermo Fisher). Each sample (200 μg) was reconstituted with 50 mM HEPES pH 8.5 and individually labeled with 500 μg of TMTpro reagent for 1 hour at room temperature. Labeling efficiency was evaluated by LC-MS/MS analysis of a pooled sample from 1 μl of each sample. After confirming >98% efficiency, samples were quenched with 50% hydroxylamine to a final concentration of 0.4%. Labeled peptide samples were combined (1:1) and desalted using Thermo desalting spin column followed by being dried via vacuum centrifugation. The dried TMT-labeled sample was fractionated offline using high pH reversed phase HPLC (Agilent 1260) using an Agilent ZORBAX 300Extend-C18 column (3.5-μm, 4.6×250 mm) with mobile phase A containing 4.5 mM ammonium formate (pH 10) in 2% (vol/vol) LC-MS grade acetonitrile, and mobile phase B containing 4.5 mM ammonium formate (pH 10) in 90% (vol/vol) LC-MS grade acetonitrile. The 96 resulting fractions were then concatenated in a non-continuous manner into 24 fractions and 5% of each were aliquoted, dried down via vacuum centrifugation and stored at −80° C. until further analysis.

LC/MS/MS Analysis

The proteome and phosphoproteome fractions were analyzed by LC/MS/MS using a Thermo Ultimate3000 nLC coupled to an Exploris480 mass spectrometer (Thermo Scientific). Samples were injected onto an Ion Opticks Aurora C18 column (75 m id×15 cm, 1.6 m particle size) and separated over a 70- or 100-min method. The gradient for separation consisted of 5-42% mobile phase B at a 250 nl/min flow rate, where mobile phase A was 0.1% formic acid in water and mobile phase B consisted of 0.1% formic acid in 80% ACN. The Exploris480 was operated in TurboTMTpro mode with a cycle time of 3s. Resolution for the precursor scan (m/z 375-1400) was set to 60,000 with a AGC target set to standard and a maximum injection time set to auto. MS2 scans (30,000 resolution) consisted of higher collision dissociate (HCD) set to 38; AGC target set to 300%; maximum injection time set to auto; isolation window of 0.7 Da; fixed first mass of 110 m/z.

Proteomics MS Search

All MS raw files were jointly searched using MaxQuant[62] (MQ) 2.4.3.0 Andromeda search engine[63] using the UniProt Mouse Reference Proteome[64] (21,864 sequences, accessed October 2023) and known contaminants included in MQ. The peptide length was set to 8-25 with a maximum mass of 4,600 Da. False Discovery Rate (FDR) for peptide identification was set at <0.01 with a minimum of one razor peptide. Peptide search was matched between runs with a match time window of 0.7 min. MS2 reporter ion for TMTpro-16plex (Thermo) was searched using manufacturers isotope correction factors with a reporter mass tolerance of 0.003 Da. Reporter ions were filtered by a minimum precursor intensity fraction (PIF) of 0.75. Oxidation and N-terminal acetylation were set as variable modifications, and carbamidomethyl was set as fixed modifications. Digestion was set to Trypsin/P with three maximum missed cleavages. Default orbitrap settings were used for spectrometer.

Proteomics Differential Expression and GSEA

Global proteomic differential expression analysis was performed in R (v4.3.1) using LIMMA (v3.56.2)[65]. Contaminants and reverse sequences were removed, and sample intensities were log 2 transformed and median normalized. Sample quality was assessed by total intensity distributions, principal component analysis, and sample correlation analyses. Proteins were median centered by the median of control samples (DMSO) before performing differential expression analysis. Missing data was not imputed. Gene set enrichment analysis was performed on differential expression analysis results using msigdbr (v7.5.1) and fgsea (v1.26.0).

Generation of Experimental MAPK Gene Expression Signature

Drug Perturbation Assays and PLATE-Seq Experiment

PLATE-Seq experiment was performed in collaboration with Columbia University's Genome Center. Panc-1 and AsPC-1 pancreatic cancer cells were cultured in 96-well tissue culture-treated plates at optimized density, in 100 μl of their optimal media. After 24 h of incubation, the plates were treated with following compounds: RAF inhibitors—Sorafenib, Dabrafenib, RAF709, PLX8394, GDC-0879; MEK inhibitors—Trametinib, Cobimetinib, Binimetinib, Selumetinib, Rafametinib; and ERK inhibitors—SCH772984, Ulixertinib, AZD0364, Ravoxertinib (all drugs were obtained from SelleckChem). Each compound was dosed at the concentration at which the cells were 80% viable after 48 h of treatment. After 24 h of treatment, the medium was replaced with 100 ml of FBS supplemented with 10% DMSO and the plates were frozen at −80° C. prior to PLATE-Seq. Detailed protocol for preparation of the automated PLATE-SEQ experiment was described by Bush et al.

Generation of GSEA Signature

The PLATE-Seq FASTQ files were pseudoaligned to the GRCh38 human transcriptome and gene expression was quantified using kallisto (version 0.44.0), tximport package (Soneson et al., 2015), and biomaRt package (Durinck et al., 2009). The gene expression was quantified as both raw counts (i.e. sequencing fragments per genomic locus) and transcripts per million (i.e. sequencing fragments per genomic locus normalized for transcript/gene length and sample sequencing depth). Single sample differential gene expression signatures were computed independently for each one of the two cell lines and then integrated in order to derive a consensus MAPK signature. The z-score method was used to generate differential gene expression signatures of each drug-treated sample with respect to the DMSO-treated samples.

REFERENCES

1 Punekar, S. R., Velcheti, V., Neel, B. G. & Wong, K. K. The current state of the art and future trends in RAS-targeted cancer therapies. Nat Rev Clin Oncol 19, 637-655 (2022). doi.org:10.1038/s41571-022-00671-9

2 Prior, I. A., Hood, F. E. & Hartley, J. L. The Frequency of Ras Mutations in Cancer. Cancer Res 80, 2969-2974 (2020). doi.org:10.1158/0008-5472.CAN-19-3682

3 Waters, A. M. & Der, C. J. KRAS: The Critical Driver and Therapeutic Target for Pancreatic Cancer. Cold Spring Harb Perspect Med 8 (2018). doi.org:10.1101/cshperspect.a031435

4 Janne, P. A. et al. Adagrasib in Non-Small-Cell Lung Cancer Harboring a KRAS(G12C) Mutation. N Engl J Med 387, 120-131 (2022). doi.org:10.1056/NEJMoa2204619

5 Skoulidis, F. et al. Sotorasib for Lung Cancers with KRAS p.G12C Mutation. N Engl J Med 384, 2371-2381 (2021). doi.org:10.1056/NEJMoa2103695

6 Strickler, J. H. et al. Sotorasib in KRAS p.G12C-Mutated Advanced Pancreatic Cancer. N Engl J Med 388, 33-43 (2023). doi.org:10.1056/NEJMoa2208470

7 Bekaii-Saab, T. S. et al. Adagrasib in Advanced Solid Tumors Harboring a KRAS(G12C) Mutation. J Clin Oncol, JC02300434 (2023). doi.org:10.1200/JCO.23.00434

8 Awad, M. M. et al. Acquired Resistance to KRAS(G12C) Inhibition in Cancer. N Engl J Med 384, 2382-2393 (2021). doi.org:10.1056/NEJMoa2105281

9 Tanaka, N. et al. Clinical Acquired Resistance to KRAS (G12C) Inhibition through a Novel KRAS Switch-II Pocket Mutation and Polyclonal Alterations Converging on RAS-MAPK Reactivation. Cancer Discov 11, 1913-1922 (2021). doi.org:10.1158/2159-8290.CD-21-0365

10 Zhao, Y. et al. Diverse alterations associated with resistance to KRAS(G12C) inhibition. Nature 599, 679-683 (2021). doi.org:10.1038/s41586-021-04065-2

11 Kemp, S. B. et al. Efficacy of a Small-Molecule Inhibitor of KrasG12D in Immunocompetent Models of Pancreatic Cancer. Cancer Discov 13, 298-311 (2023). oi.org:10.1158/2159-8290.CD-22-1066

12 Hallin, J. et al. Anti-tumor efficacy of a potent and selective non-covalent KRAS(G12D) inhibitor. Nat Med 28, 2171-2182 (2022). doi.org:10.1038/s41591-022-02007-7

13 Kim, D. et al. Pan-KRAS inhibitor disables oncogenic signalling and tumour growth. Nature 619, 160-166 (2023). doi.org:10.1038/s41586-023-06123-3

14 M, H. (In Preparation) (2023).

15 Cox, A. D., Fesik, S. W., Kimmelman, A. C., Luo, J. & Der, C. J. Drugging the undruggable RAS: Mission possible?Nat Rev Drug Discov 13, 828-851 (2014). doi.org:10.1038/nrd4389

16 Ryan, M. B. & Corcoran, R. B. Therapeutic strategies to target RAS-mutant cancers. Nat Rev Clin Oncol 15, 709-720 (2018). doi.org:10.1038/s41571-018-0105-0

17 Collins, M. A. et al. Oncogenic Kras is required for both the initiation and maintenance of pancreatic cancer in mice. J Clin Invest 122, 639-653 (2012). doi.org:10.1172/JCI59227

18 Collins, M. A. et al. Metastatic pancreatic cancer is dependent on oncogenic Kras in mice. PLoS One 7, e49707 (2012). doi.org:10.1371/journal.pone.0049707

19 Ying, H. et al. Oncogenic Kras maintains pancreatic tumors through regulation of anabolic glucose metabolism. Cell 149, 656-670 (2012). doi.org:10.1016/j.cell.2012.01.058

20 Johnson, L. et al. K-ras is an essential gene in the mouse with partial functional overlap with N-ras. Genes Dev 11, 2468-2481 (1997). doi.org:10.1101/gad.11.19.2468

21 Damnernsawad, A. et al. Kras is Required for Adult Hematopoiesis. Stem Cells 34, 1859-1871 (2016). doi.org:10.1002/stem.2355

22 Lietman, C. D., Johnson, M. L., McCormick, F. & Lindsay, C. R. More to the RAS Story: KRAS(G12C) Inhibition, Resistance Mechanisms, and Moving Beyond KRAS(G12C). Am Soc Clin Oncol Educ Book 42, 1-13 (2022). doi.org:10.1200/EDBK_351333

23 ACS Cancer Facts and Figures (2020).

24 Foundation Medicine Insights August (2020).

25 Hosein, A. N., Brekken, R. A. & Maitra, A. Pancreatic cancer stroma: an update on therapeutic targeting strategies. Nat Rev Gastroenterol Hepatol 17, 487-505 (2020). doi.org:10.1038/s41575-020-0300-1

26 Hasselluhn, M. C. et al. Tumor Explants Elucidate a Cascade of Paracrine SHH, WNT, and VEGF Signals Driving Pancreatic Cancer Angiosuppression. Cancer Discov (2023). doi.org:10.1158/2159-8290.CD-23-0240

27 Olive, K. P. et al. Inhibition of Hedgehog signaling enhances delivery of chemotherapy in a mouse model of pancreatic cancer. Science 324, 1457-1461 (2009).

28 Provenzano, P. P. et al. Enzymatic targeting of the stroma ablates physical barriers to treatment of pancreatic ductal adenocarcinoma. Cancer Cell 21, 418-429 (2012). doi.org:10.1016/j.ccr.2012.01.007

29 Bardeesy, N. et al. Both p16(Ink4a) and the p19(Arf)-p53 pathway constrain progression of pancreatic adenocarcinoma in the mouse. Proc Natl Acad Sci USA 103, 5947-5952 (2006).

30 Kotani, T. et al. Role of Ras in regulation of intestinal epithelial cell homeostasis and crosstalk with Wnt signaling. PLoS One 16, e0256774 (2021). doi.org:10.1371/journal.pone.0256774

31 Kaunitz, J. D. & Akiba, Y. Control of Intestinal Epithelial Proliferation and Differentiation: The Microbiome, Enteroendocrine L Cells, Telocytes, Enteric Nerves, and

41

GLP, Too. Dig Dis Sci 64, 2709-2716 (2019). doi.org: 10.1007/s10620-019-05778-1

32 Yang, J. et al. Dinaciclib prolongs survival in the LSL-Kras(G12D/+); LSL-Trp53(R172H/+); Pdx-1-Cre (KPC) transgenic murine models of pancreatic ductal adenocarcinoma. Am J Transl Res 12, 1031-1043 (2020).

33 Sastra, S. A. & Olive, K. P. Quantification of murine pancreatic tumors by high-resolution ultrasound. Methods Mol Biol 980, 249-266 (2013). doi.org:10.1007/978-1-62703-287-2_13

34 Xue, J. Y. et al. Rapid non-uniform adaptation to conformation-specific KRAS(G12C) inhibition. Nature 577, 421-425 (2020). doi.org:10.1038/s41586-019-1884-x 35 Solanki, H. S. et al. Cell Type-specific Adaptive Signaling Responses to KRAS(G12C) Inhibition. Clin Cancer Res 27, 2533-2548 (2021). doi.org:10.1158/1078-0432.CCR-20-3872

36 Baslan, T. et al. Ordered and deterministic cancer genome evolution after p53 loss. Nature 608, 795-802 (2022). doi.org:10.1038/s41586-022-05082-5

37 Maddipati, R. et al. MYC Levels Regulate Metastatic Heterogeneity in Pancreatic Adenocarcinoma. Cancer Discov 12, 542-561 (2022). doi.org:10.1158/2159-8290.CD-20-1826

38 Zhao, B., Pobbati, A. V., Rubin, B. P. & Stauffer, S. Leveraging Hot Spots of TEAD-Coregulator Interactions in the Design of Direct Small Molecule Protein-Protein Interaction Disruptors Targeting Hippo Pathway Signaling. Pharmaceuticals (Basel) 16 (2023). doi.org:10.3390/ph16040583

39 Soucek, L. et al. Inhibition of Myc family proteins eradicates KRas-driven lung cancer in mice. Genes Dev 27, 504-513 (2013). doi.org:10.1101/gad.205542.112

40 Raepple, D. et al. Determination of Ras-GTP and Ras-GDP in patients with acute myelogenous leukemia (AML), myeloproliferative syndrome (MPS), juvenile myelomonocytic leukemia (JMML), acute lymphocytic leukemia (ALL), and malignant lymphoma: assessment of mutational and indirect activation. Ann Hematol 88, 319-324 (2009). doi.org:10.1007/s00277-008-0593-6

41 Fernandes Neto, J. M. et al. Multiple low dose therapy as an effective strategy to treat EGFR inhibitor-resistant NSCLC tumours. Nat Commun 11, 3157 (2020). doi.org:10.1038/s41467-020-16952-9

42 Li, J. et al. Tumor Cell-Intrinsic Factors Underlie Heterogeneity of Immune Cell Infiltration and Response to Immunotherapy. Immunity 49, 178-193 e177 (2018). doi.org:10.1016/j.immuni.2018.06.006

43 Garcia, E. P. et al. Validation of OncoPanel: A Targeted Next-Generation Sequencing Assay for the Detection of Somatic Variants in Cancer. Arch Pathol Lab Med 141, 751758 (2017). doi.org:10.5858/arpa.2016-0527-OA 44 Johnson, W. E., Li, C. & Rabinovic, A. Adjusting batch effects in microarray expression data using empirical Bayes methods. Biostatistics 8, 118-127 (2007). doi.org:10.1093/biostatistics/kxj037

45 Ghandi, M. et al. Next-generation characterization of the Cancer Cell Line Encyclopedia. Nature 569, 503-508 (2019). doi.org:10.1038/s41586-019-1186-3

46 Freed, D. A., R.; Weber, J. A.; Edwards, J. S. The Sentieon Genomics Tools—A fast and accurate solution to variant calling from next-generation sequence data. bioRxiv (2017).

47 Chakravarty, D. et al. OncoKB: A Precision Oncology Knowledge Base. JCO Precis Oncol 2017 (2017). doi.org: 10.1200/PO.17.00011

42

48 Patro, R., Duggal, G., Love, M. I., Irizarry, R. A. & Kingsford, C. Salmon provides fast and bias-aware quantification of transcript expression. Nat Methods 14, 417-419 (2017). doi.org:10.1038/nmeth.4197

49 Robinson, M. D., McCarthy, D. J. & Smyth, G. K. edgeR: a Bioconductor package for differential expression analysis of digital gene expression data. Bioinformatics 26, 139140 (2010). doi.org:10.1093/bioinformatics/btp616

50 Soneson, C., Love, M. I. & Robinson, M. D. Differential analyses for RNA-seq: transcript-level estimates improve gene-level inferences. F1000Res 4, 1521 (2015). doi.org: 10.12688/f1000research.7563.2

51 Sholl, L. M. et al. Institutional implementation of clinical tumor profiling on an unselected cancer population. JCI Insight 1, e87062 (2016). doi.org:10.1172/jci.insight.87062

52 Boj, S. F. et al. Organoid models of human and mouse ductal pancreatic cancer. Cell 160, 324-338 (2015). doi.org:10.1016/j.cell.2014.12.021

53 Tiriac, H. et al. Organoid Profiling Identifies Common Responders to Chemotherapy in Pancreatic Cancer. Cancer Discov 8, 1112-1129 (2018). doi.org:10.1158/2159-8290.CD-18-0349

54 Hasselluhn, M. C. et al. "Tumor Explants Elucidate a Cascade of Paracrine SHH, WNT, and VEGF Signals Driving Pancreatic Cancer Angiosuppression". bioRxiv, 2023.2003.2002.529724 (2023). doi.org:10.1101/2023.03.02.529724

55 Maurer, C. et al. Experimental microdissection enables functional harmonisation of pancreatic cancer subtypes. Gut 68, 1034-1043 (2019). doi.org:10.1136/gutjnl-2018-317706

56 Maurer, H. C. & Olive, K. P. Laser Capture Microdissection on Frozen Sections for Extraction of High-Quality Nucleic Acids. Methods Mol Biol 1882, 253-259 (2019). doi.org:10.1007/978-1-4939-8879-2_23

57 Bartlett, D. A., Dileep, V., Baslan, T. & Gilbert, D. M. Mapping Replication Timing in Single Mammalian Cells. Curr Protoc 2, e334 (2022). doi.org:10.1002/cpz1.334

58 Baslan, T. et al. Optimizing sparse sequencing of single cells for highly multiplex copy number profiling. Genome Res 25, 714-724 (2015). doi.org:10.1101/gr.188060.114

59 Venkatraman, E. S. & Olshen, A. B. A faster circular binary segmentation algorithm for the analysis of array CGH data. Bioinformatics 23, 657-663 (2007). doi.org: 10.1093/bioinformatics/bt1646

60 Cleveland, W. S. Robust Locally Weighted Regression and Smoothing Scatterplots. 829836.

61 Seshan, V. E. Detecting copy number changes and structural rearrangements using DNA sequencing., Vol. 355-378 (2014).

62 Cox, J. & Mann, M. MaxQuant enables high peptide identification rates, individualized p.p.b.-range mass accuracies and proteome-wide protein quantification. Nat Biotechnol 26, 1367-1372 (2008). doi.org:10.1038/nbt.1511

63 Jurgen Cox*†, N. N., Annette Michalski†, Richard A. Scheltemat, Jesper V. Olsen$, and Matthias Mann*†‡. Andromeda: A Peptide Search Engine Integrated into the MaxQuant Environment. J. Proteome Res. 10, 1794-1805 (2011).

64 UniProt Consortium, T. UniProt: the universal protein knowledgebase. Nucleic Acids Res 46, 2699 (2018). doi.org:10.1093/nar/gky092

65 Ritchie, M. E. et al. limma powers differential expression analyses for RNA-sequencing and microarray studies. Nucleic Acids Res 43, e47 (2015). doi.org:10.1093/nar/gkv007

The invention claimed is:

1. A method of treating a tumor in a subject, which tumor is resistant to a RAS$^{MULTI}$ inhibitor therapy, comprising (i) identifying or having identified the tumor resistant to a RAS$^{MULTI}$ inhibitor therapy as having (a) a MYC copy number higher than a predetermined reference value and/or (b) a JUN copy number higher than a predetermined reference value; and (ii) administering to a tumor so-identified in (i) an amount of a RAS$^{MULTI}$ inhibitor and an amount of a small molecule TEAD inhibitor, effective to treat a tumor resistant to a RAS$^{MULTI}$ inhibitor therapy, wherein the RAS$^{MULTI}$ inhibitor comprises at least one of the following:

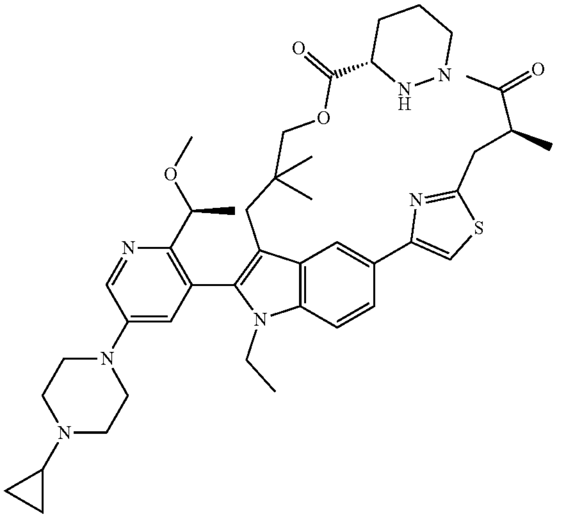

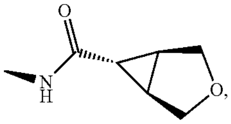

, or

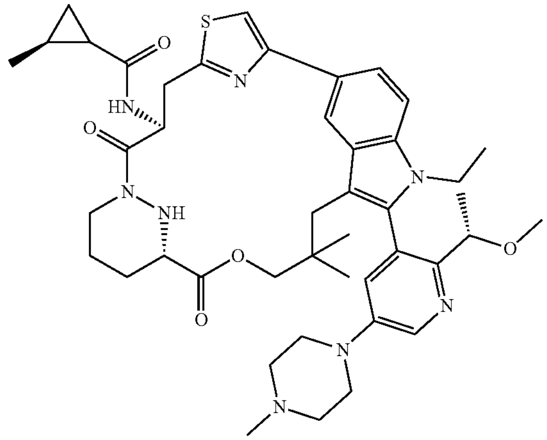

or (1S,2S)—N-((63S,4S,Z)-11-ethyl-12-(2-((S)-1-methoxyethyl)-5-(4-methylpiperazin-1-yl) pyridin-3-yl)-10,10-dimethyl-5,7-dioxo-61,62,63,64,65,66-hexahydro-11H-8-oxa-2(4,2)-thiazola-1(5,3)-indola-6(1,3)-pyridazinacycloundecaphane-4-yl)-2-methylcyclopropane-1-carboxamide.

2. The method of claim 1, wherein the tumor is identified as having a MYC copy number higher than a predetermined reference value.

3. The method of claim 1, wherein the RAS$^{MULTI}$ inhibitor is a small molecule mutation-agnostic RAS inhibitor or small molecule RAS$^{MULTI}$ inhibitor which binds to GTP-bound RAS.

4. The method of claim 1, wherein the tumor is identified as having a JUN copy number higher than a predetermined reference value.

5. The method of claim 1, wherein the MYC is c-MYC, l-MYC, or n-MYC.

6. The method of claim 1, wherein the tumor is a tumor of a pancreatic tissue.

7. The method of claim 1, wherein the tumor is a RAS-mutated cancer.

8. The method of claim 1, wherein the subject is not treated with a mutation-specific RAS inhibitor or a non-RAS$^{MULTI}$ inhibitor.

9. The method of claim 1, wherein the predetermined reference value is determined as an average MYC copy number relative to that of a normal diploid genome of the same tissue type as the tumor.

10. The method of claim 1, wherein the tumor is a pancreatic ductal adenocarcinoma (PDAC) and the predetermined reference value is an average MYC copy number in PDAC tumor cells not resistant to RAS$^{MULTI}$ inhibitor therapy.

11. The method of claim 1, wherein the small molecule TEAD inhibitor is at least one of the following: TEAD K-975; N-(1-((3-(trifluoromethyl) phenyl) amino)-2, 3-dihydro-1H-inden-5-yl) acrylamide: N-(1-(4-(trifluoromethyl) phenyl)-1H-indol-5-yl) acrylamide; N-(3-(methoxymethyl)-1-(4-(trifluoromethyl) phenyl)-1H-indol-5-yl) acrylamide; N-(3-methyl-1-(3-(trifluoromethyl) benzyl)-1H-indol-5-yl) acrylamide; N-(3-(((trans)-4-(trifluoromethyl) cyclohexyl) oxy)-2, 3-dihydro-1H-inden-5-yl) acrylamide; N-(3-((3, 4-difluorophenyl) amino)-2, 3-dihydro-1H-inden-5-yl) acrylamide; N-(3-(4-(trifluoromethyl) phenoxy)-2, 3-dihydro-1H-inden-5-yl) acrylamide, or is IAG933 having the structure:

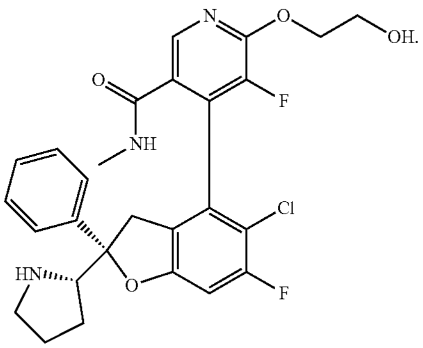 [SMILES: CNC(=O)c1cnc(OCCO)c(F)c1-c1c(Cl)c(F)cc2c1C[C@](c1ccccc1)([C@@H]1CCCN1)O2]

12. The method of claim 1, wherein the subject has previously been treated with a RAS$^{MULTI}$ inhibitor but not a TEAD inhibitor.

13. The method of claim 1, wherein the subject has not previously been treated with a RAS$^{MULTI}$ inhibitor and/or has not previously been treated with a KRAS G12C inhibitor.

14. A method of treating a tumor identified as having an elevated MYC copy number in a subject comprising administering to the tumor an amount of a $RAS^{MULTI}$ inhibitor and an amount of a small molecule TEAD inhibitor, effective to treat a tumor having an elevated MYC copy number wherein the $RAS^{MULTI}$ inhibitor comprises at least one of the following:

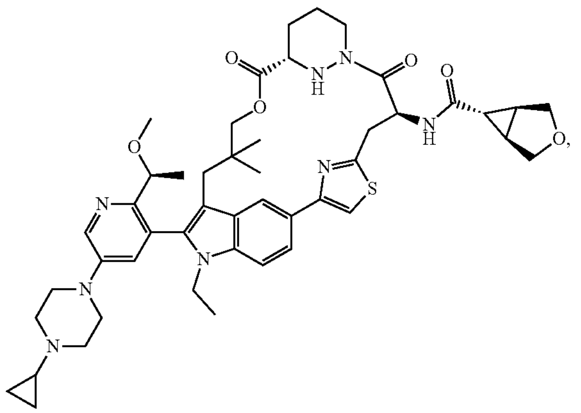

or

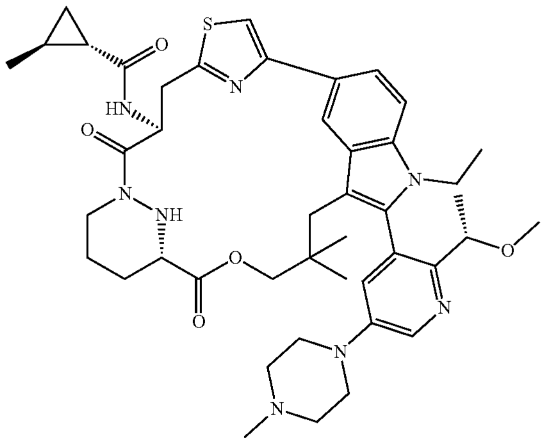

or (1S,2S)—N-((63S,4S, Z)-11-ethyl-12-(2-((S)-1-methoxyethyl)-5-(4-methylpiperazin-1-yl) pyridin-3-yl)-10, 10-dimethyl-5,7-dioxo-61,62,63,64,65,66-hexahydro-11H-8-oxa-2 (4, 2)-thiazola-1 (5, 3)-indola-6(1,3)-pyridazinacycloundecaphane-4-yl)-2-methylcyclopropane-1-carboxamide.

15. The method of claim 1, wherein the $RAS^{MULTI}$ inhibitor comprises:

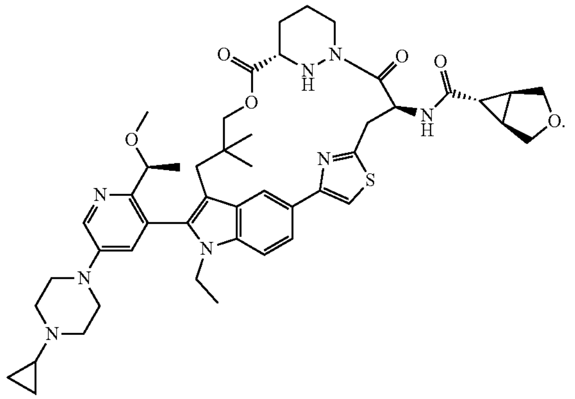 [SMILES: CCn1c(-c2cc(N3CCN(C4CC4)CC3)cnc2[C@H](C)OC)c2c3cc(ccc31)-c1csc(n1)C[C@H](NC(=O)[C@H]1[C@@H]3COC[C@@H]31)C(=O)N1CCC[C@H](N1)C(=O)OCC(C)(C)C2]

16. The method of claim 14, wherein the $RAS^{MULTI}$ inhibitor comprises:

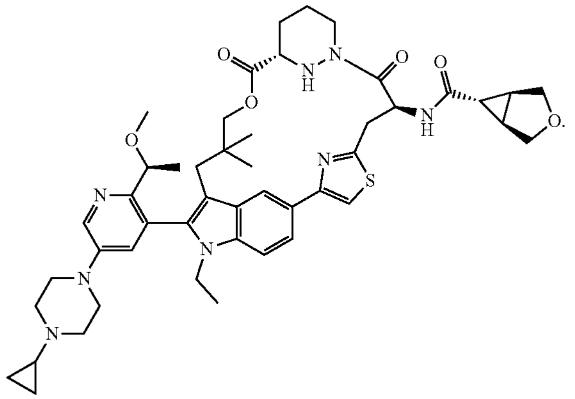 [SMILES: CCn1c(-c2cc(N3CCN(C4CC4)CC3)cnc2[C@H](C)OC)c2c3cc(ccc31)-c1csc(n1)C[C@H](NC(=O)[C@H]1[C@@H]3COC[C@@H]31)C(=O)N1CCC[C@H](N1)C(=O)OCC(C)(C)C2]

* * * * *